United States Patent
Shaul et al.

(10) Patent No.: US 11,873,322 B2
(45) Date of Patent: Jan. 16, 2024

(54) SYSTEMS AND METHODS FOR INCREASING EFFICIENCY OF GENOME EDITING

(71) Applicant: Yeda Research and Development Co. Ltd., Rehovot (IL)

(72) Inventors: Yosef Shaul, Rehovot (IL); Nina Reuven, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 566 days.

(21) Appl. No.: 17/254,932

(22) PCT Filed: Jun. 25, 2019

(86) PCT No.: PCT/IL2019/050707
§ 371 (c)(1),
(2) Date: Dec. 22, 2020

(87) PCT Pub. No.: WO2020/003311
PCT Pub. Date: Jan. 2, 2020

(65) Prior Publication Data
US 2021/0115092 A1 Apr. 22, 2021

Related U.S. Application Data

(60) Provisional application No. 62/712,260, filed on Jul. 31, 2018, provisional application No. 62/689,268, filed on Jun. 25, 2018.

(51) Int. Cl.
| | | |
|---|---|---|
| *C07K 14/005* | (2006.01) | |
| *A61K 31/7088* | (2006.01) | |
| *A61K 38/46* | (2006.01) | |
| *C12N 7/00* | (2006.01) | |
| *C12N 9/22* | (2006.01) | |
| *C12N 15/11* | (2006.01) | |
| *C12N 15/90* | (2006.01) | |

(52) U.S. Cl.
CPC ........ *C07K 14/005* (2013.01); *A61K 31/7088* (2013.01); *A61K 38/465* (2013.01); *C12N 7/00* (2013.01); *C12N 9/22* (2013.01); *C12N 15/11* (2013.01); *C12N 15/907* (2013.01); *C07K 2319/00* (2013.01); *C12N 2310/20* (2017.05); *C12N 2710/00022* (2013.01); *C12N 2710/00033* (2013.01); *C12N 2800/80* (2013.01)

(58) Field of Classification Search
None
See application file for complete search history.

(56) References Cited

U.S. PATENT DOCUMENTS 7,135,324 B2 11/2006 Weller
10,314,297 B2 * 6/2019 Shen .................... C12N 15/102
2004/0141994 A1 7/2004 Weller et al.
2017/0191078 A1 7/2017 Zhang et al.
2017/0268022 A1 9/2017 Liu et al.

FOREIGN PATENT DOCUMENTS

| WO | WO 2012/118717 | 9/2012 |
|---|---|---|
| WO | WO 2016/025759 | 2/2016 |
| WO | WO 2016/054326 | 4/2016 |
| WO | WO 2017/142923 | 8/2017 |
| WO | WO 2020/003311 | 1/2020 |

OTHER PUBLICATIONS

International Preliminary Report on Patentability dated Jan. 7, 2021 From the International Bureau of WIPO Re. Application No. PCT/IL2019/050707. (9 Pages).
International Search Report and the Written Opinion dated Sep. 23, 2019 From the International Searching Authority Re. Application No. PCT/IL2019/050707. (15 Pages).
Balasubramanian et al. "Physical Interaction Between the Herpes Simplex Virus Type 1 Exonuclease, UL12, and the DNA Double-Strand Break-Sensing MRN Complex", Journal of Virology, 84(24): 12504-12514, Dec. 2010.
Charpentier et al. "CtIP Fusion to Cas9 Enhances Transgene Integration by Homology-dependent Repair", Nature Communications, 9(1): 1133, pp. 1-11, Mar. 19, 2018.
Chu et al. "Increasing the Efficiency of Homology-directed Repair for CRISPR-Cas9-induced Precise Gene Editing in Mammalian Cells", Nature Biotechnology, 33(5): 543-548, May 2015.
Gutschner et al. "Post-translational Regulation of Cas9 during G1 Enhances Homology-Directed Repair", Cell Reports, 14(6): 1555-1566, Feb. 16, 2016.
Maruyama et al. "Increasing the Efficiency of Precise Genome Editing with CRISPR-Cas9 by Inhibition of Nonhomologous End Joining", Nature Biotechnology, 33(5): 538-542, May 2015.
Schumacher et al. "The HSV-1 Exonuclease, UL12, Stimulates Recombination by a Single Strand Annealing Mechanism", PLoS Pathogens, 8(8): e1002862, pp. 1-10, Aug. 9, 2012.
Song et al. "RS-1 Enhances CRISPR/Cas9- and TALEN-mediated Knock-in Efficiency", Nature communications, 7: 10548, pp. 1-7, Jan. 28, 2016.
Syed et al. The MRE11-RAD50-NBS1 Complex Conducts the Orchestration of Damage Signaling and Outcomes to Stress in DNA Replication and Repair, Annual Review of Biochemistry, 87: 35.1-35.32, Apr. 25, 2018.

* cited by examiner

Primary Examiner — Suzanne M Noakes
Assistant Examiner — Jae W Lee

(57) ABSTRACT

A recombinant system for improving genome editing via homologous recombination is disclosed. The system comprising a first nucleic acid sequence encoding a DNA editing agent having a double strand DNA cutting activity and a second nucleic acid sequence encoding a polypeptide capable of increasing homologous recombination in a target cell.

Figure 4A:
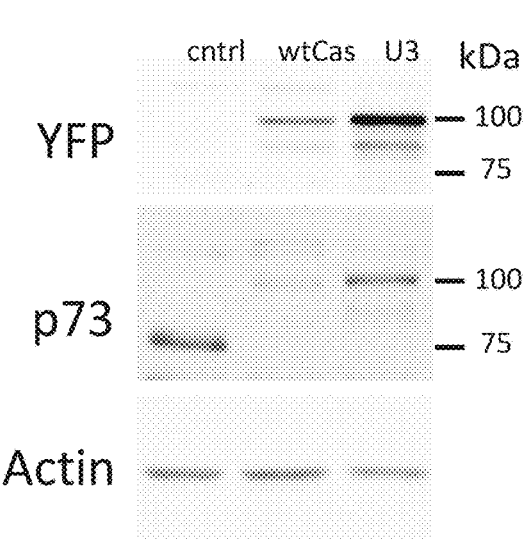

21 Claims, 9 Drawing Sheets
Specification includes a Sequence Listing.

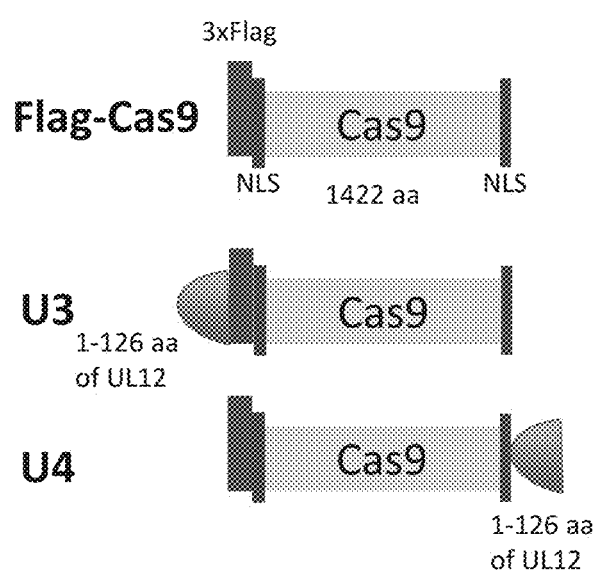
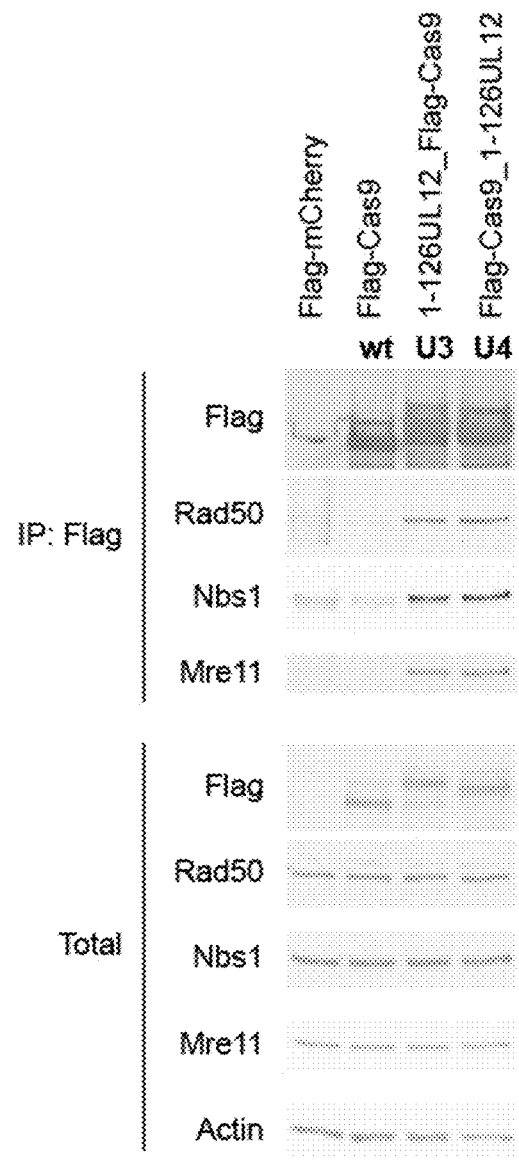
FIG. 1A
FIG. 1B

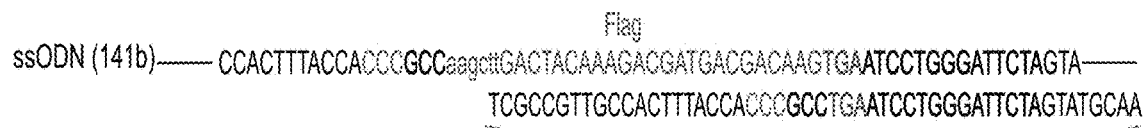
FIG. 2A
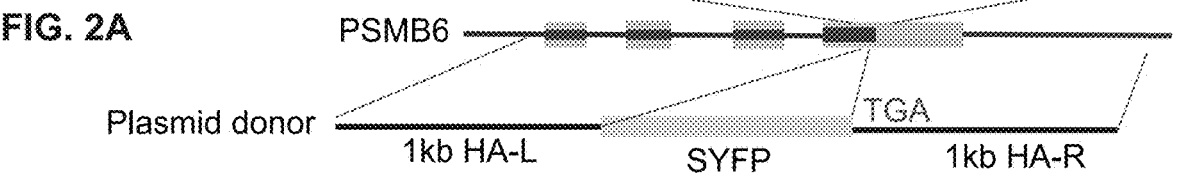
FIG. 2B
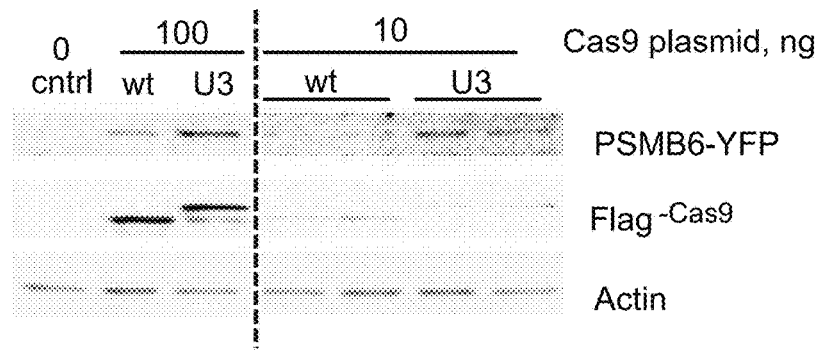
FIG. 2C
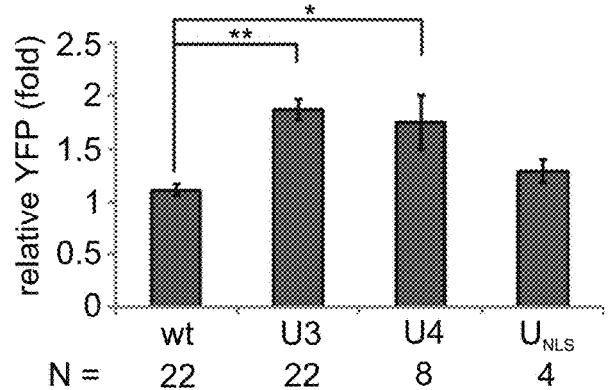
FIG. 2D
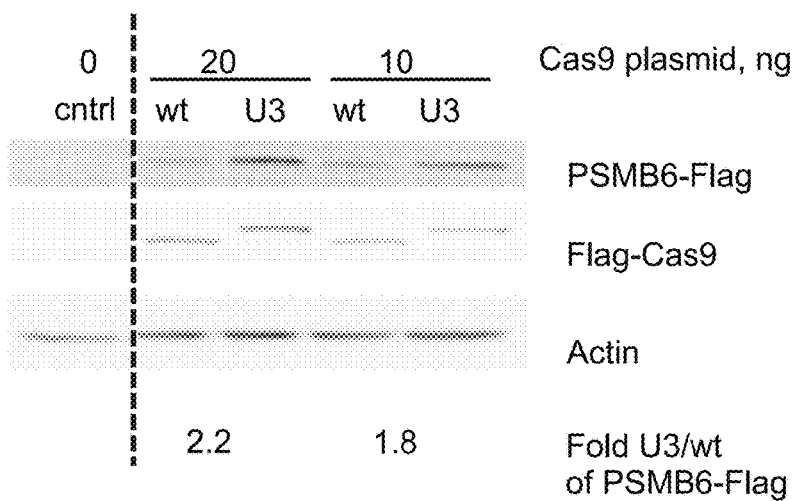

FIG. 3A
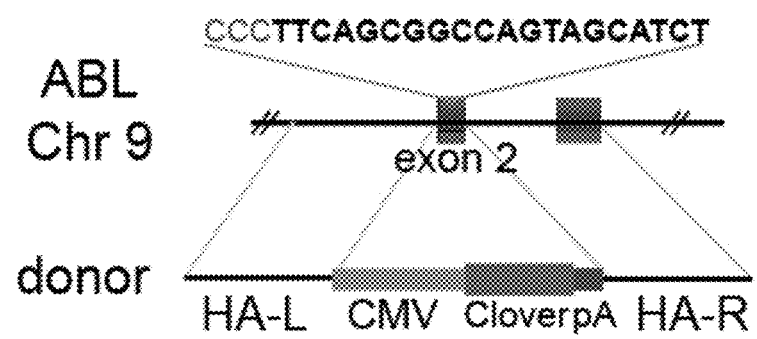
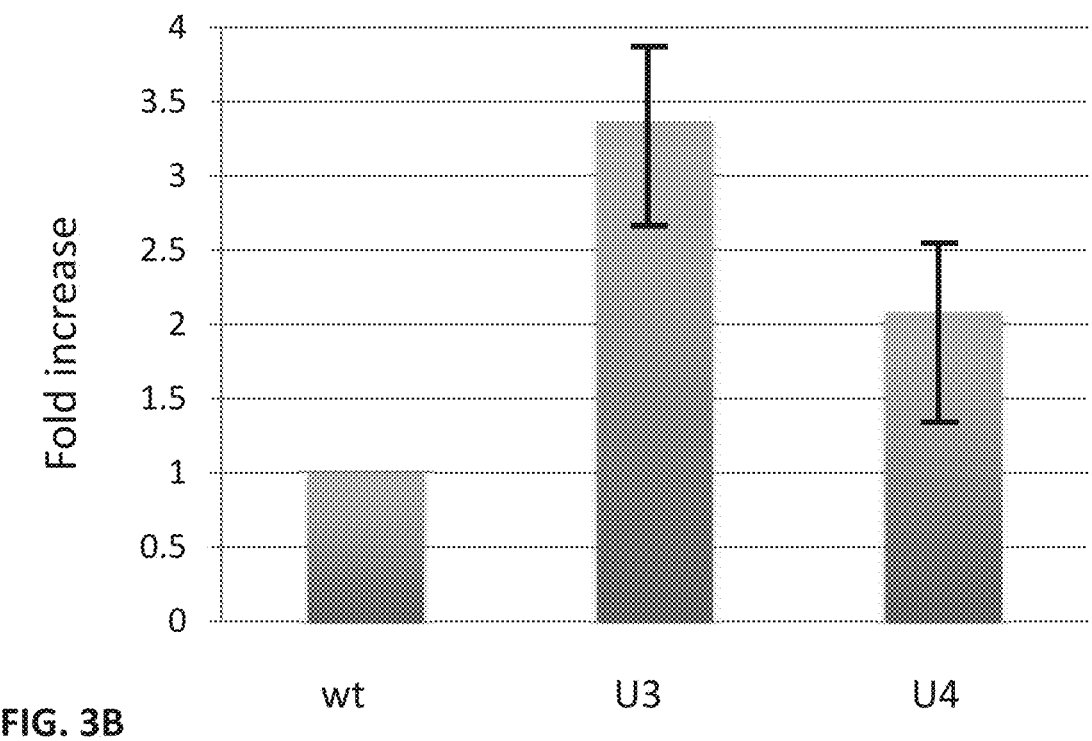
FIG. 3B

Short extension time used

Long extension time used

FIG. 7A
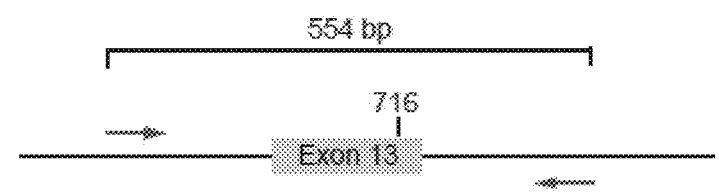
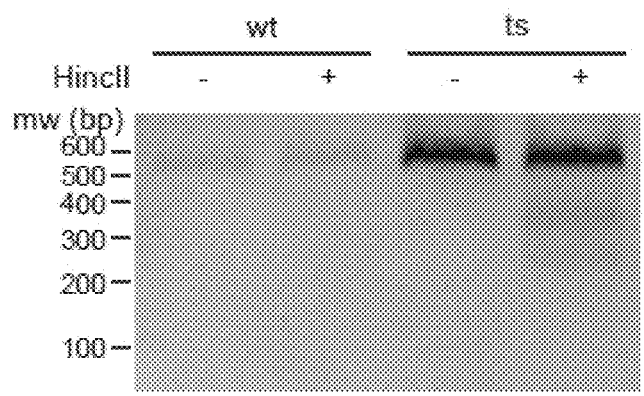
FIG. 7B

SYSTEMS AND METHODS FOR INCREASING EFFICIENCY OF GENOME EDITING

RELATED APPLICATIONS

This application is a National Phase of PCT Patent Application No. PCT/IL2019/050707 having International filing date of Jun. 25, 2019, which claims the benefit of priority under 35 USC §119(e) of U.S. Provisional Patent Application Nos. 62/712,260 filed on Jul. 31, 2018 and 62/689,268 filed on Jun. 25, 2018. The contents of the above applications are all incorporated by reference as if fully set forth herein in their entirety.

SEQUENCE LISTING STATEMENT

The ASCII file, entitled 85247 SequenceListing.txt, created on Dec. 22, 2020, comprising 74,714 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to recombinant systems comprising a DNA editing agent having a double strand DNA cutting activity and a polypeptide capable of increasing homologous recombination and, more particularly, but not exclusively, to the use of same for improving genome editing via homologous recombination.

CRISPR (clustered regularly interspaced short palindromic repeat) and Cas (CRISPR-associated) proteins are part of the RNA-based adaptive immune system in bacteria and archaea. Cas9 is a DNA endonuclease, which is targeted to a specific target site by a short RNA guide sequence (sgRNA) complementary to the target sequence. The resulting double-strand break is usually repaired by the endogenous cell repair machinery, either by non-homologous end joining (NHEJ) or homologous recombination (HR), with NHEJ being the predominant repair pathway. NHEJ is highly efficient, but error prone, and produces small insertions or deletions (indels), generally resulting in frame shift mutations, thus generating a gene knockout. Homology-directed repair (HDR) can occur if a donor template DNA with homology to the sequences flanking the DSB is provided, to produce edited sites with specific, targeted modifications (gene knock-in).

Recently, several groups have reported strategies to increase HDR by reducing NHEJ, stimulating HR, or by restricting the Cas9 cleavage to the portion of the cell cycle with optimal HDR. These approaches have included inhibiting NHEJ by knockdown strategy or by inhibiting ligase IV with a specific inhibitor, (Chu et al., 2015; Maruyama et al., 2015), by pharmacologically enhancing HDR (Song et al., 2016) or by restricting Cas9 expression to the S/G2/M portion of the cell cycle (Gutschner et al., 2016). Altering the global DNA repair environment in the cell has the potential danger of introducing unwanted mutations at random sites. A recent study has used fusion of a 296 aa domain of the repair protein CtIP to Cas9, and have achieved increases in editing of 1.5-2.5 fold over the unmodified Cas9 (Charpentier et al., 2018).

Herpes simplex virus (HSV)-1 (HSV-1) encodes a two subunit recombinase, consisting of a 5'-3' exonuclease, UL12, and a single stranded binding/pairing protein, ICP8. The two proteins together can mediate recombination (strand exchange) in vitro. In vivo, expression of the recombinase and in most cases even expression of UL12 alone, increases recombination by the single-strand annealing pathway, and inhibits NHEJ (Schumacher et al., 2012). Importantly, the N-terminus of UL12 has been shown to efficiently recruit the cellular MRN complex (Mre11/Rad50/Nbs1) (Balasubramanian et al., 2010). The MRN complex coordinates double-strand break (DSB) repair, and resects dsDNA ends and recruits factors needed for HDR (Syed and Tainer, 2018).

U.S. Patent Application no. 20170191078 discloses vectors and vector systems, which encode one or more components of a CRISPR complex, as well as methods for the design and use of such vectors. Also provided are Cas9 proteins comprising one or more mutations or being fused to one or more effector domains (e.g. Cas9-NLS-VP64 fusion protein).

U.S. Patent Application no. 20170268022 discloses compositions, methods, systems, and kits for controlling the activity of RNA-programmable endonucleases, such as Cas9, or for controlling the activity of proteins comprising a Cas9 variant fused to a functional effector domain (e.g. a nuclease, nickase, recombinase, deaminase, transcriptional activator, transcriptional repressor, or epigenetic modifying domain). Also provided are Cas9 protein comprising an intein.

U.S. Pat. No. 7,135,324 discloses a HSV recombinase comprising the purified or isolated alkaline nuclease UL12 and the single stranded DNA binding protein ICP8. U.S. Pat. No. 7,135,324 also discloses methods of using the HSV recombinase for cloning, treating cells and organisms, and producing transgenic animals.

SUMMARY OF THE INVENTION

According to an aspect of some embodiments of the present invention there is provided a recombinant system for improving genome editing via homologous recombination, the system comprising a first nucleic acid sequence encoding a DNA editing agent having a double strand DNA cutting activity and a second nucleic acid sequence encoding a polypeptide capable of increasing homologous recombination in a target cell.

According to an aspect of some embodiments of the present invention there is provided a proteinaceous system encoded by the system of some embodiments of the invention.

According to an aspect of some embodiments of the present invention there is provided a nucleic acid construct or construct system comprising the first nucleic acid sequence encoding the DNA editing agent having the double strand DNA cutting activity and the second nucleic acid sequence encoding the polypeptide capable of increasing homologous recombination according to the system of some embodiments of the invention.

According to an aspect of some embodiments of the present invention there is provided a pharmaceutical composition comprising the system of some embodiments of the invention or nucleic acid construct or construct system of some embodiments of the invention, and a pharmaceutically acceptable carrier or diluent.

According to an aspect of some embodiments of the present invention there is provided a method of increasing genome editing in a targeted manner in a target cell, the method comprising subjecting the target cell to a genome editing reagent comprising the system of some embodiments of the invention, or nucleic acid construct or construct system of some embodiments of the invention, thereby increasing the homologous recombination in the target cell.

According to an aspect of some embodiments of the present invention there is provided a method of treating a disease or disorder amenable to treatment by homologous recombination in a subject in need thereof, the method comprising administering to the subject the system of some embodiments of the invention, or nucleic acid construct or construct system of some embodiments of the invention, thereby treating the disease or disorder.

According to an aspect of some embodiments of the present invention there is provided a system of some embodiments of the invention, or nucleic acid construct or construct system of some embodiments of the invention, for use in treating a disease or disorder amenable to treatment by homologous recombination in a subject in need thereof, wherein the disease or disorder is selected from the group consisting of a cancer, an infection, an inflammation, an autoimmune disease, a genetic disease or disorder, an immune deficiency, and a metabolic disorder.

According to some embodiments of the invention, the first nucleic acid sequence and the second nucleic acid sequence are translationally fused.

According to some embodiments of the invention, the first nucleic acid sequence is fused to the second nucleic acid sequence at an N-termini of the first nucleic acid sequence.

According to some embodiments of the invention, the first nucleic acid sequence is fused to the second nucleic acid sequence at a C-termini of the first nucleic acid sequence.

According to some embodiments of the invention, each of the first nucleic acid sequence and the second nucleic acid sequence is translationally fused to a member of an affinity binding pair such that the DNA editing agent having the double strand DNA cutting activity and the polypeptide capable of increasing homologous recombination form a protein complex in the target cell.

According to some embodiments of the invention, the homologous recombination comprises homology-directed repair (HDR).

According to some embodiments of the invention, the DNA editing agent having the double strand DNA cutting activity is of a DNA editing system selected from the group consisting of meganucleases, Zinc finger nucleases (ZFNs), transcription-activator like effector nucleases (TALENs) and CRISPR-Cas.

According to some embodiments of the invention, the DNA editing agent having the double strand DNA cutting activity comprises Cas9.

According to some embodiments of the invention, the system further comprises a nucleic acid sequence encoding at least one sgRNA.

According to some embodiments of the invention, the polypeptide capable of increasing homologous recombination is capable of increasing homology directed repair.

According to some embodiments of the invention, the polypeptide capable of increasing homologous recombination is capable of recruiting at least one component of the cellular MRN complex (Mre11/Rad50/Nbs1).

According to some embodiments of the invention, the polypeptide capable of increasing homologous recombination is an alkaline nuclease.

According to some embodiments of the invention, the polypeptide capable of increasing homologous recombination is a viral peptide.

According to some embodiments of the invention, the viral peptide is derived from a herpesvirus.

According to some embodiments of the invention, the herpesvirus is selected from the group consisting of Herpes simplex virus 1 (HSV-1), Herpes simplex virus 2 (HSV-2), Varicella zoster virus (VZV), Epstein-Barr virus (EBV), Cytomegalovirus (CMV), Roseolovirus and Kaposi's sarcoma-associated herpesvirus (KSHV).

According to some embodiments of the invention, the viral peptide is derived from HSV-1.

According to some embodiments of the invention, the viral peptide is UL12.

According to some embodiments of the invention, the UL12 comprises amino acids 1-126 of an N-terminal fragment of UL12.

According to some embodiments of the invention, when the first nucleic acid sequence and the second nucleic acid sequence are translationally fused, the encoded polypeptide comprises a Cas9-UL12 fusion protein.

According to some embodiments of the invention, the polypeptide capable of increasing homologous recombination is a eukaryotic polypeptide.

According to some embodiments of the invention, the eukaryotic polypeptide is selected from the group consisting of a Single-stranded DNA-binding protein (mitochondrial), Nuclear cap-binding protein subunit 1, Heat shock protein HSP 90-beta, Putative heat shock protein HSP 90-beta-3, Heat shock protein HSP 90-alpha, Transmembrane protein 263, ATP synthase subunit gamma (mitochondrial), Mitochondrial 2-oxoglutarate/malate carrier protein, Complement component 1 Q subcomponent-binding protein (mitochondrial), Mitochondrial import receptor subunit TOM22 homolog, Serine/threonine-protein phosphatase PGAM5 (mitochondrial), Voltage-dependent anion-selective channel protein 2, Histone H1.3, Protein WWC2, Transmembrane protein 33, HIG1 domain family member 1A (mitochondrial), CDK5 regulatory subunit-associated protein 2, Eukaryotic translation elongation factor 1 epsilon-1, DNA repair protein RAD50, Sideroflexin-4, Importin subunit alpha-4, E3 ubiquitin-protein ligase RBX1;E3 ubiquitin-protein ligase RBX1 (N-terminally processed), DNA-binding protein RFX7, ATP synthase subunit alpha, mitochondrial, Vimentin, Trafficking protein particle complex subunit 8, Pyruvate kinase PKM, GTP-binding nuclear protein Ran, Prohibitin-2, Importin subunit alpha-1, Synapsin-3, Peroxisome biogenesis factor 1, Nibrin, DnaJ homolog subfamily B member 6, DnaJ homolog subfamily B member 3, DnaJ homolog subfamily B member 8, DnaJ homolog subfamily B member 2, Cystatin-A;Cystatin-A, N-terminally processed, T-complex protein 1 subunit alpha, E3 ubiquitin-protein ligase TRIM21, Elongation factor 1-gamma, Double-strand break repair protein MRE11A, Heat shock protein 75 kDa (mitochondrial), Probable C-mannosyltransferase DPY19L1, Biogenesis of lysosome-related organelles complex 1 subunit 2, Nuclear pore complex protein Nup93, Leucine-rich repeat neuronal protein 4, Very-long-chain enoyl-CoA reductase, Peroxisomal sarcosine oxidase, Mitochondrial dicarboxylate carrier, Wings apart-like protein homolog, Cofilin-1, Destrin, Cofilin-2, Tubulin alpha-1B chain, Tubulin alpha-1A chain, Tubulin alpha-1C chain, Tubulin alpha-4A chain, Tubulin alpha-3C/D chain, Tubulin alpha-3E chain, Heat shock 70 kDa protein 1B, Heat shock 70 kDa protein 1A, Puromycin-sensitive aminopeptidase-like protein, Serine/arginine repetitive matrix protein 3, Protein PAT1 homolog 2, Centrosomal protein of 290 kDa, Zinc finger protein 25, ADAMTS-like protein 3, CAP-Gly domain-containing linker protein 4, EH domain-binding protein 1-like protein 1, Synaptotagmin-like protein 5, Guanine nucleotide exchange factor DBS, Nuclear transition protein 2, Protein bicaudal D homolog 1 and Putative helicase Mov10L1.

According to some embodiments of the invention, the polypeptide capable of increasing homologous recombination comprises a plurality of polypeptides.

According to some embodiments of the invention, the nucleic acid sequence(s) is under a transcriptional control of a cis-acting regulatory element.

According to some embodiments of the invention, the homologous recombination is associated with a modification selected from the group consisting of a deletion, an insertion, a point mutation and a combination thereof.

According to some embodiments of the invention, when the modification is an insertion, the method further comprises introducing into the target cell donor oligonucleotides.

According to some embodiments of the invention, the subjecting is effected in vivo.

According to some embodiments of the invention, the subjecting is effected ex vivo.

According to some embodiments of the invention, the target cell is a mammalian cell.

According to some embodiments of the invention, the target cell is associated with a disease or disorder.

According to some embodiments of the invention, the disease or disorder is selected from the group consisting of a cancer, an infection, an inflammation, an autoimmune disease, a genetic disease or disorder, an immune deficiency, and a metabolic disorder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a schematic representation of chimeric *Streptococcus pyogenes* CRISPR-Associated protein 9 (SpCas9) constructs.

FIG. 1B illustrates that chimeric Cas9 constructs interact with endogenous MRN. HEK293 cells were transfected with the Flag-Cas9 constructs indicated, or Flag-mCherry. Cells were harvested and extracts subjected to IP with anti-Flag. IP and total extract samples were analyzed by SDS-PAGE and immunoblot with the indicated antibodies. Of note: the Flag-mCherry protein, due to its small size, was run out of the gel under the conditions used and was therefore not detected.

FIGS. 2A-D illustrate editing of proteasome subunit PSMB6 in human cell lines. FIG. 2A) Schematic representation of a portion of the PSMB6 locus and donor DNA constructs. The stop codon (TGA) of PSMB6 is indicated in red. The guide RNA sequence is in bold, and the PAM sequence is in pink (of note, the complementary strand to the one shown is the targeted strand). The plasmid donor for insertion of SYFP at the C-terminus of PSMB6 is shown schematically, with 1 kb homology arms flanking the YFP insertion; FIG. 2B) HEK293 cells grown in 12-well plates were transfected with 0.5 μg donor plasmid (pBS_PSMB6-YFP) and the amounts indicated of pX330-based plasmids with a guide targeting the region of the stop codon of the proteasomal subunit PSMB6 (guide shown in (a)). pBluescript KS- was added to bring the amount of DNA per well to 2 μg. The pX330 plasmids used here express Flag-Cas9 (wt) or 1-126UL12-Flag-Cas9 (U3). The correct recombination product creates a PSMB6-YFP fusion protein that migrates at 50 kDa when the samples are boiled. The cells were harvested two days post-transfection and boiled samples were analyzed on a 12.5% SDS-PAGE gel. Proteins were transferred to nitrocellulose at 350 mA for 1 h. The membrane was probed overnight at 4° C. with anti-GFP/YFP (living colors). Enhanced chemiluminescence was performed with the EZ-ECL kit (Biological Industries, Kibbutz Beit Haemek, Israel). The membrane was reprobed at RT 1.5 h with anti-FlagM2 and anti-actin; FIG. 2C) Summary of editing of PSMB6-YFP by chimeric constructs. Quantification of multiple experiments using this system with the indicated wildtype (wt) and chimeric Cas9 constructs. The $U_{NLS}$ construct comprised amino acids 1-50 of UL12 fused to the N-terminus of Cas9. Signals were detected by the ImageQuant LAS 4000 (GE Healthcare, Piscataway, N.J.). Intensities of bands were quantified by the ImageQuant TL software. (**$p<10^{-7}$, *$p<0.04$); FIG. 2D) HEK293 cells were transfected with ssODN and pX330-based plasmids as in (FIG. 2B). They were also co-transfected with pEFIRES (has puro-resistance gene). The correct recombination product creates a PSMB6-Flag fusion protein that runs at approx. 23 kDa. The cells were split three days post-transfection into medium with 0.5 μg/ml puromycin to select for transfected cells. Cells were harvested two days later and analyzed on a 12.5% SDS-PAGE gel, and a 10% gel for analysis of Cas9 expression levels. Samples were boiled 5 min in sample buffer before loading. Proteins were transferred to nitrocellulose at 350 mA for 1 h. The membranes were probed overnight at 4° C. with anti-FlagM2. The 12.5% gel's membrane (for PSMB6-Flag detection) was re-probed at RT 1.5 h with anti-actin.

FIGS. 3A-B illustrate insertion of CMV-Clover cassette in ABL locus. HEK293FT cells were transfected with donor plasmid with 1000- and 900 bp homology arms flanking a CMV-Clover cassette (FIG. 3A), alone or together with pX330-based plasmids encoding a guide targeting the ABL locus and unmodified (wt) or U3 or U4 Cas9 constructs. Cells were passaged 5-6 times post-transfection, until the expression of GFP (Clover) in the donor-only transfected cells was at background level. FIG. 3B) Expression of GFP (Clover) was analyzed by FACS analysis of biological triplicates of pools of transfected cells, with 100,000 cells collected per sample. Error bars represent SEM.

Figure 4B:
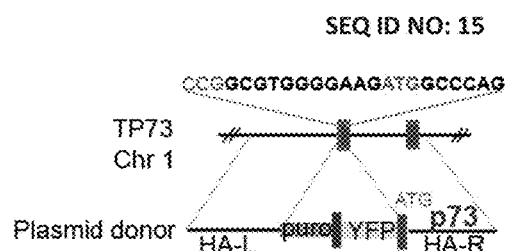
Figure 4C:
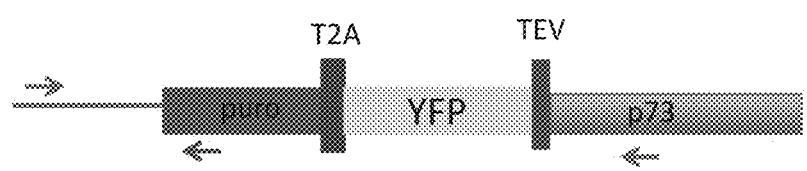
Figure 4D:
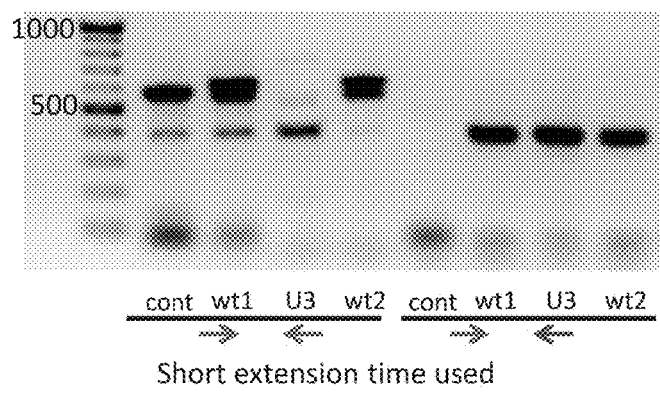
Figure 4E:
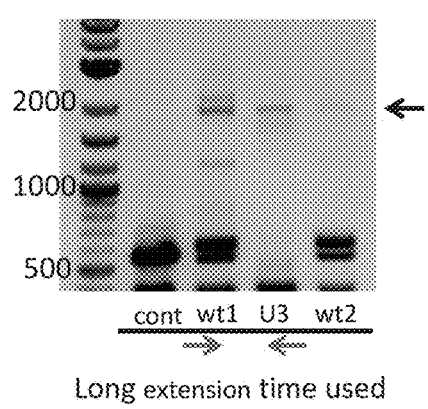
Figure 4F:
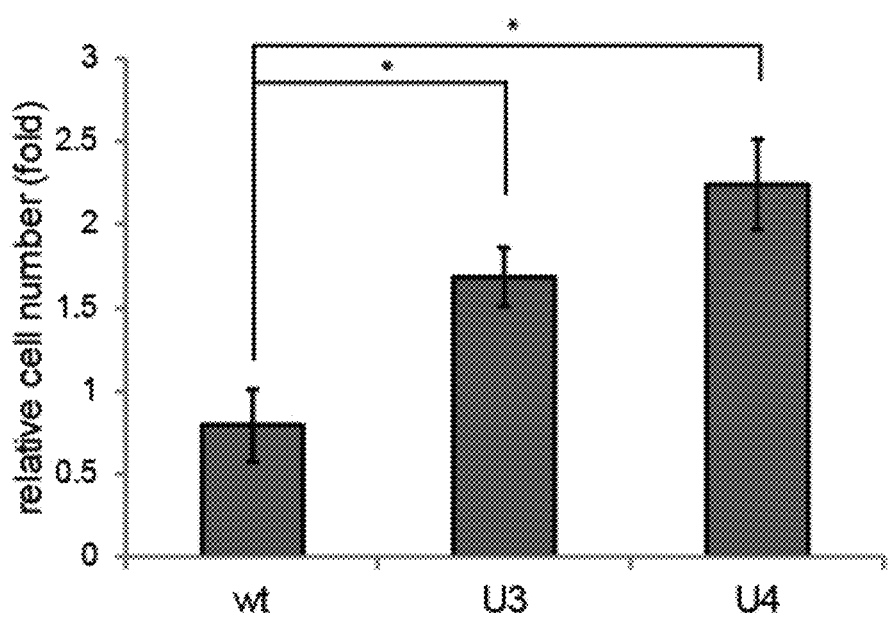

FIGS. 4A-F illustrate insertion of a puro-T2A-YFP-TEV cassette to the p73 locus. FIGS. 4A-C) HEK293 cells were transfected with donor DNA plasmid with 1 kb homology arms flanking puro-2A-YFP-TEV cassette (cassette illustrated in FIGS. 4B and 4C), and pX330-based vectors encoding a guide RNA and unmodified (wt) or U3 Cas9. Selection for puro-resistant cells. Clones were purified and analyzed by western blot and PCR of genomic DNA. Western blot analysis (FIG. 4A) showing that puro-selected cells were all knocked out for unmodified p'73, and express the 100 kDa YFP-p73; FIGS. 4D-E) PCR analysis of genomic DNA of control cells, and clones edited using wtCas9 or U3. The clone arising from U3 editing appears to be homozygous for the insertion of the cassette. The blue primers amplify a 600 bp fragment in the control cells, and a 2 kb fragment with the insertion of the full puro_T2A_YFP_TEV cassette. The black arrow indicates the size of the correct cassette insertion PCR product. The red and blue primer pair amplify a 400 bp band indicating the correct insertion of the cassette. FIG. 4F) Quantification of puromycin-resistant pools of transfected cells using XTT assay. Biological quadruplicates were analyzed. Error bars represent SEM.

Figure 5A:
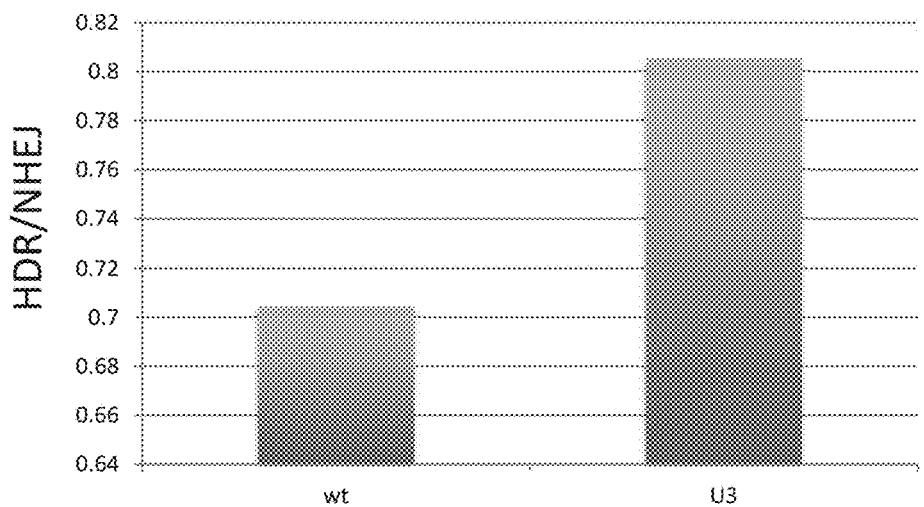
Figure 5B:
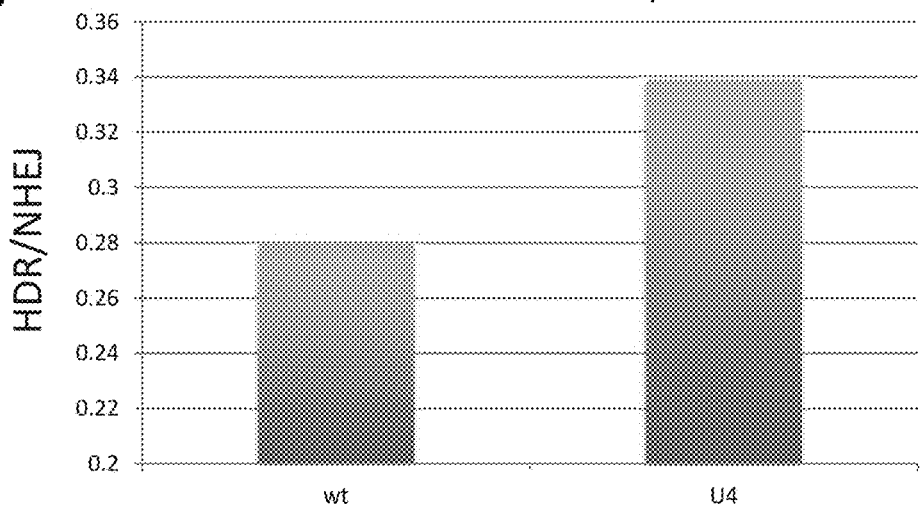
Figure 5C:
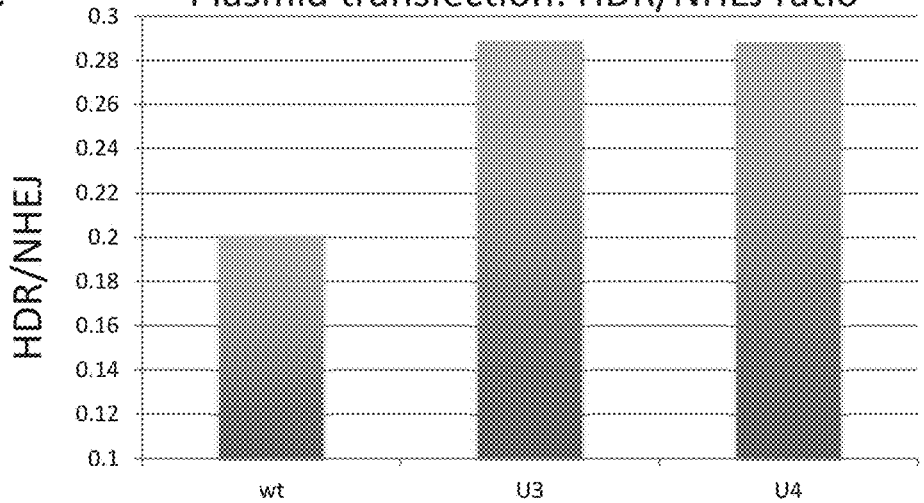

FIGS. 5A-C illustrate that the chimeric Cas9 constructs favor HDR over NHEJ. HEK293FT cells harboring a single copy of a reporter gene cassette were transfected with Cas9/sgRNA using the methods outlined below, together with ssODN donor template that encodes a point mutation changing the fluorescence of the reporter from blue to green, indicating HDR. The Cas9 and sgRNA were delivered using FIG. 5A) RNA transfection of in vitro transcribed RNAs; FIG. 5B) transfection of recombinant Cas9 protein complexed with in vitro transcribed sgRNA; and FIG. 5C) plasmids encoding Cas9 driven by a CBh promoter, and sgRNA by the U6 promoter. Cells were transfected in quadruplicate, and were re-plated 2 days post-transfection. Cells were passaged 1-2 more times, and harvested for FACS analysis, with 100,000 cells analyzed per point. Cells edited by HDR express GFP, cells edited by NHEJ resulting in indels express neither BFP (Blue Fluorescent Protein) nor GFP (Green Fluorescent Protein). Bars represent the ratio of HDR:NHEJ when editing with the indicated Cas9 constructs.

Figure 6A:
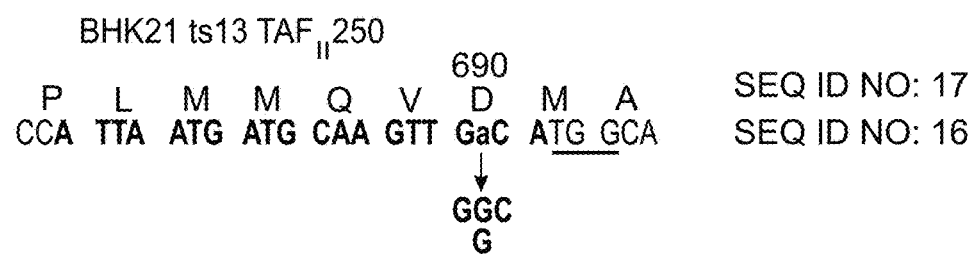
Figure 6B:
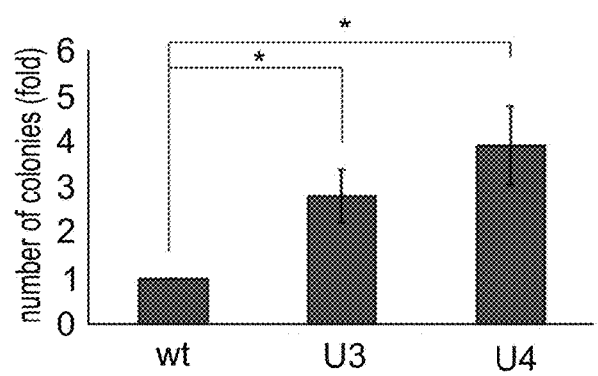

FIGS. 6A-B illustrate that MRN recruitment improved editing of an endogenous point mutation in baby hamster kidney cells. FIG. 6A) Site of the G690D ts mutation in BHK21 ts13 cells. The guide sequence targeting the mutation site is shown in bold, with the PAM site underlined. FIG. 6B) Editing of the ts mutation in BHK21 ts13 was 2-4 fold more efficient with MRN-recruiting constructs. BHK21 ts13 cells were transfected with the indicated Cas9/sgRNA expressing plasmids and the ssODN donor. Two days post-transfection, cells were replated, and transferred the next day to 39.5° C. Two weeks later, colonies were stained with crystal violet, and counted. Statistical analysis: Student's T-test was performed, two-tailed, two-sample, unequal variance test. N=7, *p<0.02.

Figure 7C:
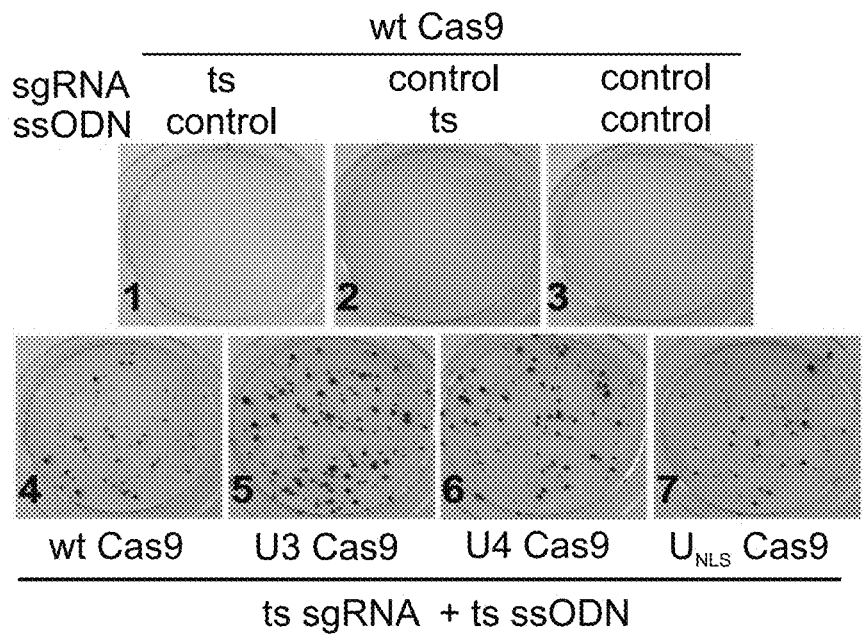
Figure 7D:
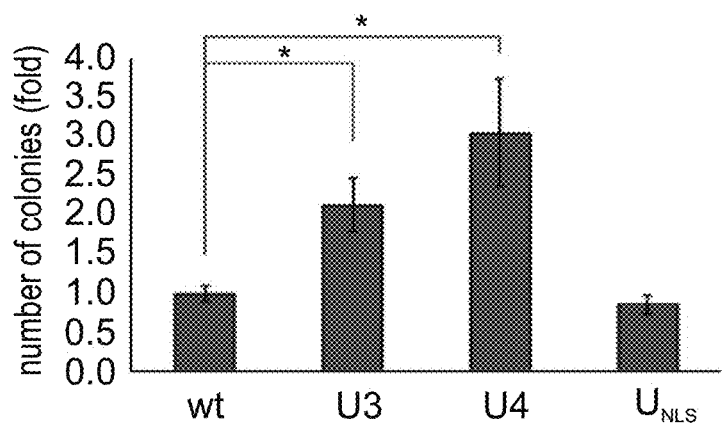
Figure 7E:
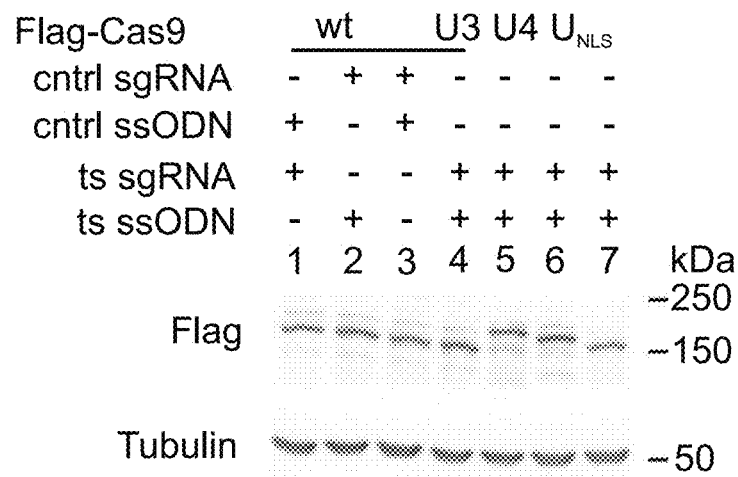

FIGS. 7A-E illustrate that MRN recruitment improved editing of an endogenous point mutation in human cells. Specifically, HEK293 cells were CRISPR edited to carry the same mutation that was identified in the BHK21 ts13. FIG. 7A) Editing of HEK293 to produce TAF1 G716D ts cells. Guide sequences for targeting the wt locus, and subsequently the mutated locus, are indicated in green, and the PAM sequences are indicated in pink. The ts mutation creates a HincII site. FIG. 7B) PCR analysis of representative HEK293 TAF1ts clone. A 554 bp fragment was amplified from the genomic DNA of a wt (control) and ts clone, and cleaved with HincII. HincII cleavage indicates incorporation of the mutant sequence. FIGS. 7C-D) Reversion of TAF1 ts mutation in HEK293 was 2-fold more efficient with MRN-recruiting constructs. HEK293 TAF1 ts cells were transfected with the indicated Cas9/sgRNA-encoding plasmids and ssODN. Control non-targeting sgRNA and ssODN were non-specific to human sequences. Cells were transfected and treated as in (FIG. 6B). FIG. 7C) Crystal violet-stained cells. FIG. 7D) Editing of HEK293 TAF1 is by wt, U3, U4 and $U_{NLS}$ Cas9. Statistical analysis as in (FIG. 6B) *p<0.011. FIG. 7E) Equivalent expression of Flag-Cas9 constructs in cells from (FIGS. 7C-D). Samples of cells transfected in (FIGS. 7C-D) were analyzed by SDS-PAGE and immunoblotting with anti-Flag to detect the Flag-Cas9 constructs.

DESCRIPTION OF SPECIFIC EMBODIMENTS OF THE INVENTION

The present invention, in some embodiments thereof, relates to recombinant systems comprising a DNA editing agent having a double strand DNA cutting activity and a polypeptide capable of increasing homologous recombination and, more particularly, but not exclusively, to the use of same for improving genome editing via homologous recombination.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

CRISPR/Cas9 is a powerful tool for genome editing in cells and organisms. This technology enables the creation of a double-strand break at a specific chosen location in the genome. With repair of the break by the cellular non-homologous end-joining pathway (NHEJ), the site is often repaired with small insertions or deletions (indels), which can insert frameshift mutations and result in "knockout" of targeted genes. To introduce directed, edited changes at the break site, a template DNA with the desired sequence, flanked by regions of homology, is required. In addition, the cellular homologous repair machinery is also required. Since NHEJ usually predominates over homologous recombination (HR), achieving the desired result can often be inefficient. Many viruses are known to manipulate the host DNA repair pathways to promote their replication, and have evolved efficient means of recruiting host factors to this end. The HSV-1 alkaline nuclease (UL12) is part of a virus-encoded two subunit DNA recombinase, with activity similar to RecE/T and lambda Red α/β. The N-terminal 126 aa of UL12, a region devoid of enzymatic activity, recruits the host MRN complex (Mre11/Rad50/Nbs1), which is among the first complexes recruited to sites of double-strand breaks, and is needed for the recruitment of factors involved in homology-directed repair (HDR).

While reducing the present invention to practice, the present inventors have uncovered that fusing the UL12 N-terminal region to the N- or C-terminus of SpCas9 resulted in proteins that interact with the cellular MRN complex (FIGS. 1A-B). The chimeric Cas9 constructs were compared for efficiency of editing several endogenous loci in human and hamster tissue culture cells, with a 2 to 6-fold improvement in efficiency with use of the chimeric constructs (FIGS. 2A-4F, 6A-B, 7A-E, and data not shown). The systems were used for effective delivery of Cas9 by means of RNA, recombinant proteins or plasmids, all yielding a higher HDR/NHEJ ratio as compared to wildtype Cas9, indicating that the chimeric Cas9 constructs favor HDR over NHEJ (FIGS. 5A-C). The systems used were: addition of SYFP or a Flag tag to the C-terminus of proteasome subunit PSMB6, with plasmid and ss oligonucleotide (ssODN) donor DNA used, respectively (FIGS. 2A-D); insertion of a CMV promoter-driven cassette encoding Clover into the ABL gene locus (FIGS. 3A-B); insertion of a cassette including puromycin resistance-T2A-YFP-TEV-p73 at the p73 locus (FIGS. 4A-F) and introduction of a point mutation which reverts a temperature-sensitive (ts) mutation to the wild type sequence (FIGS. 6A-B and 7A-E). A cell line stably expressing a reporter gene construct was used to analyze HDR/NHEJ ratio when editing with the wt vs. chimeric Cas9. Because the chimeric Cas9 constructs can recruit MRN, this targets the relevant factors directly to the Cas9-mediated break site. Thus, enhancement of HDR is local, at the engineered break site, rather than global, the latter being inferior since it leads to undesired mutations. Furthermore, the domain added to Cas9 is small, e.g. 126 aa, and does not interfere with the expression level of the Cas9, whether it is added to the N- or C-terminus of Cas9. Taken together, these constructs provide a simple means to improved genome editing efficiency and precision without altering global DNA repair in the cells.

Thus, according to one aspect of the present invention there is provided a recombinant system for improving genome editing via homologous recombination, the system comprising a first nucleic acid sequence encoding a DNA editing agent having a double strand DNA cutting activity and a second nucleic acid sequence encoding a polypeptide capable of increasing homologous recombination in a target cell.

The term "recombinant system" as used herein refers to an artificial system for the expression of heterologous nucleic acids in a target cell. Typically, the recombinant system is engineered through the insertion and expression of one or more nucleic acid sequences in a target cell, wherein the nucleic acid sequences are typically devoid of one or more introns or cis acting regulatory elements (e.g., promoter) which are native to the expressed sequence. Such a system is typically designed to comprise a codon usage which is different than the native sequences. A recombinant system may be used for combining nucleic acid sequences that would not normally occur together in the target cell.

The phrase "genome editing" as used herein refers to the process of inserting, deleting, modifying or replacing at least one nucleic acid in a directed manner in the genome of a living organism subsequent to repair of DNA breaks, such as double stranded DNA (dsDNA) breaks. Typically, genome editing can be used to insert a predetermined mutation such as for knock in (e.g. conferring a novel property to the sequence and optionally the expressed product).

As used herein, the term "homologous recombination" or HR refers to the genetic recombination in which at least one nucleotide is exchanged between two homologous segments of DNA. Homologous recombination is mostly used by the cells to repair breaks that occur on both strands of DNA, e.g. dsDNA breaks.

The recombinant system of the invention comprises a first nucleic acid sequence encoding a DNA editing agent having a double strand DNA cutting activity.

According to one embodiment, the DNA editing agent used according to some embodiments of the invention can create site-specific single- or double-stranded breaks (DSBs) in a DNA.

According to a specific embodiment, the DNA editing agent can create site-specific DSBs in a DNA.

Following is a description of various non-limiting examples of DNA editing agents, which may be used in the recombinant system of some embodiments of the invention. These include meganucleases, Zinc finger nucleases (ZFNs), transcription-activator like effector nucleases (TALENs) and CRISPR/Cas9 system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location.

This can be exploited to make site-specific double-stranded breaks (DSBs) in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence.

Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (DSBs) (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically, a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break (DSB).

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break (DSB). Repair of these double-stranded breaks (DSBs) through the non-homologous end-joining (NHEJ) pathway often results in small deletions or small sequence insertions (Indels). Since each repair made by NHEJ is unique, the use of a single nuclease pair can produce an allelic series with a range of different insertions or deletions at the target site.

In general NHEJ is relatively accurate (about 85% of DSBs in human cells are repaired by NHEJ within about 30 min from detection) in gene editing erroneous NHEJ is relied upon as when the repair is accurate the nuclease will keep cutting until the repair product is mutagenic and the recognition/cut site/PAM motif is gone/mutated or that the transiently introduced nuclease is no longer present.

The deletions typically range anywhere from a few base pairs to a few hundred base pairs in length, but larger deletions have been successfully generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break (DSB) can be repaired via homologous recombination (HR) to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers are typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, Calif.).

T-GEE system (TargetGene's Genome Editing Engine)—A programmable nucleoprotein molecular complex containing a polypeptide moiety and a specificity conferring nucleic acid (SCNA) which assembles in-vivo, in a target cell, and is capable of interacting with the predetermined target nucleic acid sequence is provided. The programmable nucleoprotein molecular complex is capable of specifically modifying and/or editing a target site within the target nucleic acid sequence and/or modifying the function of the target nucleic acid sequence. Nucleoprotein composition comprises (a) polynucleotide molecule encoding a chimeric polypeptide and comprising (i) a functional domain capable of modifying the target site, and (ii) a linking domain that is capable of interacting with a specificity conferring nucleic acid, and (b) specificity conferring nucleic acid (SCNA) comprising (i) a nucleotide sequence complementary to a region of the target nucleic acid flanking the target site, and (ii) a recognition region capable of specifically attaching to the linking domain of the polypeptide. The composition enables modifying a predetermined nucleic acid sequence target precisely, reliably and cost-effectively with high specificity and binding capabilities of molecular complex to the target nucleic acid through base-pairing of specificity-conferring nucleic acid and a target nucleic acid. The composition is less genotoxic, modular in their assembly, utilize single platform without customization, practical for independent use outside of specialized core-facilities, and has shorter development time frame and reduced costs.

CRISPR-Cas system (also referred to herein as "CRISPR")—Many bacteria and archea contain endogenous RNA-based adaptive immune systems that can degrade nucleic acids of invading phages and plasmids. These systems consist of clustered regularly interspaced short palindromic repeat (CRISPR) nucleotide sequences that produce RNA components and CRISPR associated (Cas) genes that encode protein components. The CRISPR RNAs (crRNAs) contain short stretches of homology to the DNA of specific viruses and plasmids and act as guides to direct Cas nucleases to degrade the complementary nucleic acids of the corresponding pathogen. Studies of the type II CRISPR/Cas system of *Streptococcus pyogenes* have shown that three components form a RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012) 337: 816-821).

It was further demonstrated that a synthetic chimeric guide RNA (sgRNA) composed of a fusion between crRNA and tracrRNA could direct Cas9 to cleave DNA targets that are complementary to the crRNA in vitro. It was also demonstrated that transient expression of Cas9 in conjunction with synthetic sgRNAs can be used to produce targeted double-stranded brakes (DSBs) in a variety of different species (Cho et al., 2013; Cong et al., 2013; DiCarlo et al., 2013; Hwang et al., 2013a,b; Jinek et al., 2013; Mali et al., 2013).

The CRISPR/Cas system for genome editing contains two distinct components: a sgRNA and an endonuclease e.g. Cas9. In order to effect genome editing both components should be present. In general, when the genome editing agent comprises subunits e.g., nuclease and targeting both subunits should be present in a method of genome editing.

The sgRNA is typically a 20-nucleotide sequence encoding a combination of the target homologous sequence (crRNA) and the endogenous bacterial RNA that links the crRNA to the Cas9 nuclease (tracrRNA) in a single chimeric transcript. The sgRNA/Cas9 complex is recruited to the target sequence by the base-pairing between the sgRNA sequence and the complement genomic DNA. For successful binding of Cas9, the genomic target sequence must also contain the correct Protospacer Adjacent Motif (PAM) sequence immediately following the target sequence. The binding of the sgRNA/Cas9 complex localizes the Cas9 to the genomic target sequence so that the Cas9 can cut both strands of the DNA causing a double-strand break (DSB). Just as with ZFNs and TALENs, the double-stranded breaks (DSBs) produced by CRISPR/Cas can undergo homologous recombination or NHEJ and are susceptible to specific sequence modification during DNA repair.

The Cas9 nuclease has two functional domains: RuvC and HNH, each cutting a different DNA strand. When both of these domains are active, the Cas9 causes double strand breaks (DSBs) in the genomic DNA.

A significant advantage of CRISPR/Cas is that the high efficiency of this system is coupled with the ability to easily create synthetic sgRNAs. This creates a system that can be readily modified to target modifications at different genomic sites and/or to target different modifications at the same site. Additionally, protocols have been established which enable simultaneous targeting of multiple genes. The majority of cells carrying the mutation present biallelic mutations in the targeted genes.

However, apparent flexibility in the base-pairing interactions between the sgRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is mostly repaired by single strand break repair mechanism involving proteins such as but not only, PARP (sensor) and XRCC1/LIG III complex (ligation). If a single strand break (SSB) is generated by topoisomerase I poisons or by drugs that trap PARP1 on naturally occurring SSBs then these could persist and when the cell enters into S-phase and the replication fork encounter such SSBs they will become single ended DSBs which can only be repaired by HR. However, two proximal, opposite strand nicks introduced by a Cas9 nickase are treated as a double-strand break, in what is often referred to as a 'double nick' CRISPR system. A double-nick, which is basically non-parallel DSB, can be repaired like other DSBs by HR or NHEJ depending on the desired effect on the gene target and the presence of a donor sequence and the cell cycle stage (HR is of much lower abundance and can only occur in S and G2 stages of the cell cycle). Thus, if specificity and reduced off-target effects are crucial, using the Cas9 nickase to create a double-nick by designing two sgRNAs with target sequences in close proximity and on opposite strands of the genomic DNA would decrease off-target effect as either sgRNA alone will result in nicks that are not likely to change the genomic DNA, even though these events are not impossible.

Modified versions of the Cas9 enzyme containing two inactive catalytic domains (dead Cas9, or dCas9) have no nuclease activity while still able to bind to DNA based on sgRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique sgRNAs for different genes in different species, such as but not limited to, the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both sgRNA and a Cas endonuclease (e.g. Cas9) should be expressed or present (e.g., as a ribonucleoprotein complex) in a target cell. The insertion vector can contain both cassettes on a single plasmid or the cassettes are expressed from two separate plasmids. CRISPR plasmids are commercially available such as the px330 plasmid from Addgene (75 Sidney St, Suite 550A•Cambridge, Mass. 02139). Use of clustered regularly interspaced short palindromic repeats (CRISPR)-associated (Cas)-guide RNA technology and a Cas endonuclease for modifying mammalian genomes are also at least disclosed by Bauer et al. [J Vis Exp. (2015) (95):e52118. doi: 10.3791/52118], which is specifically incorporated herein by reference in its entirety. Cas endonucleases that can be used to effect DNA editing with sgRNA include, but are not limited to, Cas9, Cpf1 (Zetsche et al., 2015, Cell. 163(3):759-71), C2c1 and C2c3 (Shmakov et al., Mol Cell. 2015 Nov. 5; 60(3):385-97). Additionally or alternatively, Cas proteins which may be used for genome editing according to some embodiments of the invention include, but are not limited to, Cas1, Cas1B, Cas2, Cas3, Cas4, Cas5, Cas6, Cas7, Cas8, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. Such Cas proteins may be derived from an organism of a genus, which includes, but is not limited to, *Corynebacter, Sutterella, Legionella, Treponema, Filifactor, Eubacterium, Streptococcus, Lactobacillus, Mycoplasma, Bacteroides, Flavobacterium, Sphaerochaeta, Azospirillum, Gluconacetobacter, Neisseria, Roseburia, Parvibaculum, Staphylococcus, Nitratifractor, Mycoplasma* and *Campylobacter*.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, introduced into the cells, and positive selection is performed to isolate homologous recombination mediated events. The DNA carrying the homologous sequence can be provided as a plasmid, single or double stranded oligo. These homologous recombinants contain a local duplication that is separated by intervening vector sequence, including the selection cassette. In the second step, targeted clones are subjected to negative selection to identify cells that have lost the selection cassette via intra-chromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After the system components have been introduced to the cell and positive selection applied, HR mediated events could be identified. Next, a second targeting vector that contains a region of homology with the desired mutation is introduced into targeted clones, and negative selection is applied to remove the selection cassette and introduce the mutation. The final allele contains the desired mutation while eliminating unwanted exogenous sequences.

According to a specific embodiment, the DNA editing agent comprises a nuclease (e.g. an endonuclease) and a DNA targeting module (e.g., sgRNA also referred to herein as sgRNA).

According to a specific embodiment, the DNA editing agent is CRISPR/Cas, e.g. sgRNA and Cas9.

According to a specific embodiment, the DNA editing agent comprises Cas9 or a variant or homolog thereof.

According to a specific embodiment, the Cas9 homolog comprises *Streptococcus pyogenes* CRISPR-Associated protein 9 (SpCas9), SaCas9 (*Staphylococcus aureus* Cas9), BlatCas9 (*Brevibacillus laterosporus* Cas9), FnCas9 (*Francisella novicida* Cas9), NmCas9 (*N. meningitidis* Cas9), St1Cas9 (*Streptococcus thermophilus* Cas9).

According to a specific embodiment, the Cas9 homolog comprises Cpf1 e.g. AsCpf1 (*Acidaminococcus* sp. BV3L6 Cpf1) and LbCpf1 (*Lachnospiraceae bacterium* Cpf1).

The recombinant system of the invention comprises a second nucleic acid sequence encoding a polypeptide capable of increasing homologous recombination.

According to one embodiment, the polypeptide capable of increasing homologous recombination is capable of increasing homology-directed repair.

According to one embodiment, the polypeptide capable of increasing homologous recombination is capable of recruiting at least one cellular factor associated with homologous recombination.

According to one embodiment, the polypeptide capable of increasing homologous recombination is capable of recruiting at least one of MRN/ATM-dependent DNA damage response factors (e.g. γH2AX, Chk2, 53BP1, Rad17, MRN complex [Mre11, Rad50, Nbs1], MDC1, CtIP, ATR, ATRIP, TopBP1, 9-1-1 complex (Rad9, HUS1, Rad1)), homologous recombination proteins (e.g. Rad51, Rad52, Rad53, Rad54, Rad55/57, Shu complex i.e. Shu1, Psy3, Shu2 and Csm2 proteins, BRCA2, BARD1, and BRCA1) or DNA-dependent ATPases associated with homologous recombination (e.g. Snf2/Swi2).

According to one embodiment, the polypeptide capable of increasing homologous recombination is capable of recruiting at least one component of the cellular MRN complex (Mre11/Rad50/Nbs1).

According to one embodiment, the polypeptide capable of increasing homologous recombination is an alkaline nuclease.

According to one embodiment, the polypeptide capable of increasing homologous recombination comprises the YqaJ conserved protein domain (also known as the YqaJ-like viral recombinase domain).

According to one embodiment, the polypeptide capable of increasing homologous recombination is a viral polypeptide (e.g. a viral alkaline nuclease, a viral DNase, or a viral alkaline exonuclease) or fragment thereof capable of recruiting at least one component of the cellular MRN complex (Mre11/Rad50/Nbs1).

According to one embodiment, the viral peptide is derived from a herpesvirus.

Exemplary herpesviruses from which the viral peptide may be derived include, but are not limited to, Herpes simplex virus 1 (HSV-1), Herpes simplex virus 2 (HSV-2), Varicella zoster virus (VZV), Epstein-Barr virus (EBV), Cytomegalovirus (CMV), Roseolovirus, Kaposi's sarcoma-associated herpesvirus (KSHV), Pseudorabies virus (PRV), and Bovine herpesvirus.

According to a specific embodiment, the viral peptide is derived from HSV-1.

According to a specific embodiment, the viral peptide is UL12, a homolog or a fragment thereof. An exemplary UL12 is set forth in SEQ ID NO: 4.

According to a specific embodiment, the UL12 comprises amino acids 1-126 of an N-terminal fragment of UL12, e.g. as set forth in SEQ ID NO: 6, a homolog or a fragment thereof.

According to one embodiment, the UL12 comprises an amino acid sequence at least 90% identical to SEQ ID NO: 6.

According to one embodiment, the UL12 comprises an amino acid sequence at least 95% identical to SEQ ID NO: 6.

According to one embodiment, the UL12 comprises an amino acid sequence at least 99% identical to SEQ ID NO: 6.

According to one embodiment, the UL12 comprises the amino acid sequence as set forth in SEQ ID NO: 6.

According to one embodiment, the UL12 comprises a fragment of 50-126, 60-126, 70-126, 80-126, 90-126, 100-126, 110-126 or 120-126 amino acids of the amino acid sequence set forth in SEQ ID NO: 6.

According to one embodiment, the UL12 comprises a fragment of 50, 60, 70, 80, 90, 100, 110, 120, 121, 122, 123, 124 or 125 consecutive amino acids of the amino acid sequence set forth in SEQ ID NO: 6.

According to a specific embodiment, the UL12 comprises amino acids 50-126 of an N-terminal fragment of UL12.

According to a specific embodiment, the viral peptide is derived from HSV-2, e.g. UL12, a homolog or a fragment thereof.

According to a specific embodiment, the viral peptide is derived from Bovine herpesvirus, e.g. UL12, a homolog or a fragment thereof.

According to one embodiment, the viral peptide is derived from CMV, e.g. UL98, a homolog or a fragment thereof.

According to one embodiment, the viral peptide is derived from EBV, e.g. P03217 (AN_EBVB9), a homolog or a fragment thereof.

According to one embodiment, the viral peptide is derived from VZV, e.g. ORF48, a homolog or a fragment thereof.

According to one embodiment, the viral peptide is derived from a baculovirus, e.g. alkaline nuclease, a homolog or a fragment thereof.

According to a specific embodiment, the viral peptide is derived from baculovirus *Autographa californica* multinucleocapsid nucleopolyhedrovirus (AcMNPV) open reading frame 133.

According to one embodiment, the viral peptide is the plant virus protein At3g48810, a homolog or a fragment thereof.

According to one embodiment, the UL12 homolog is the protein of unknown function DUF3292 (IPR021709).

Homology (e.g., percent homology, sequence identity+ sequence similarity) can be determined using any homology comparison software computing a pairwise sequence alignment.

As used herein, "sequence identity" or "identity" in the context of two nucleic acid or polypeptide sequences includes reference to the residues in the two sequences, which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89(22): 10915-9].

Identity (e.g., percent homology) can be determined using any homology comparison software, including for example, the BlastN software of the National Center of Biotechnology Information (NCBI) such as by using default parameters.

According to some embodiments of the invention, the identity is a global identity, i.e., an identity over the entire amino acid or nucleic acid sequences of the invention and not over portions thereof.

According to some embodiments of the invention, the term "homology" or "homologous" refers to identity of two or more nucleic acid sequences; or identity of two or more amino acid sequences; or the identity of an amino acid sequence to one or more nucleic acid sequence.

According to some embodiments of the invention, the homology is a global homology, i.e., a homology over the entire amino acid or nucleic acid sequences of the invention and not over portions thereof.

The degree of homology or identity between two or more sequences can be determined using various known sequence comparison tools. Following is a non-limiting description of such tools, which can be used along with some embodiments of the invention.

When starting with a polynucleotide sequence and comparing to other polynucleotide sequences the EMBOSS-6.0.1 Needleman-Wunsch algorithm (available from emboss (dot)sourceforge(dot)net/apps/cvs/emboss/apps/needle(dot) html) can be used with the following default parameters: (EMBOSS-6.0.1) gapopen=10; gapextend=0.5; datafile=EDNAFULL; brief=YES.

According to some embodiments of the invention, the threshold used to determine homology using the EMBOSS-6.0.1 Needleman-Wunsch algorithm for comparison of polynucleotides with polynucleotides is 80%, 81%, 82%, 83%, 84%, 85%, 86%, 87%, 88%, 89%, 90%, 91%, 92%, 93%, 94%, 95%, 96%, 97%, 98%, 99%, or 100%.

According to some embodiment, determination of the degree of homology further requires employing the Smith-Waterman algorithm (for protein-protein comparison or nucleotide-nucleotide comparison). Default parameters for GenCore 6.0 Smith-Waterman algorithm include: model=sw.model.

According to some embodiments of the invention, the threshold used to determine homology using the Smith-Waterman algorithm is 80%, 81%, 82%, 83%, 84%, 85%, 86%, 87%, 88%, 89%, 90%, 91%, 92%, 93%, 94%, 95%, 96%, 97%, 98%, 99%, or 100%.

According to some embodiments of the invention, the global homology is performed on sequences which are pre-selected by local homology to the polypeptide or polynucleotide of interest (e.g., 60% identity over 60% of the sequence length), prior to performing the global homology to the polypeptide or polynucleotide of interest (e.g., 80% global homology on the entire sequence). For example, homologous sequences are selected using the BLAST software with the Blastp and tBlastn algorithms as filters for the first stage, and the needle (EMBOSS package) or Frame+ algorithm alignment for the second stage. Local identity (Blast alignments) is defined with a very permissive cut-off—60% Identity on a span of 60% of the sequences lengths because it is used only as a filter for the global alignment stage. In this specific embodiment (when the local identity is used), the default filtering of the Blast package is not utilized (by setting the parameter "-F F").

In the second stage, homologs are defined based on a global identity of at least 80% to the core gene polypeptide sequence. According to some embodiments the homology is a local homology or a local identity.

Local alignments tools include, but are not limited to the BlastP, BlastN, BlastX or TBLASTN software of the National Center of Biotechnology Information (NCBI), FASTA, and the Smith-Waterman algorithm.

According to one embodiment, the polypeptide capable of increasing homologous recombination is a eukaryotic polypeptide or fragment thereof capable of recruiting at least one component of the cellular MRN complex (Mre11/Rad50/Nbs1).

According to one embodiment, the polypeptide capable of increasing homologous recombination is a eukaryotic polypeptide or fragment thereof comprising at least one component of the cellular MRN complex (i.e. Mre11, Rad50, Nbs1).

Exemplary eukaryotic polypeptides include, but are not limited to, Single-stranded DNA-binding protein (mitochondrial), Nuclear cap-binding protein subunit 1, Heat shock protein HSP 90-beta, Putative heat shock protein HSP 90-beta-3, Heat shock protein HSP 90-alpha, Transmembrane protein 263, ATP synthase subunit gamma (mitochondrial), Mitochondrial 2-oxoglutarate/malate carrier protein, Complement component 1 Q subcomponent-binding protein (mitochondrial), Mitochondrial import receptor subunit TOM22 homolog, Serine/threonine-protein phosphatase PGAM5 (mitochondrial), Voltage-dependent anion-selective channel protein 2, Histone H1.3, Protein WWC2, Transmembrane protein 33, HIG1 domain family member 1A (mitochondrial), CDK5 regulatory subunit-associated protein 2, Eukaryotic translation elongation factor 1 epsilon-1, DNA repair protein RAD50, Sideroflexin-4, Importin subunit alpha-4, E3 ubiquitin-protein ligase RBX1;E3 ubiquitin-protein ligase RBX1 (N-terminally processed), DNA-binding protein RFX7, ATP synthase subunit alpha, mitochondrial, Vimentin, Trafficking protein particle complex subunit 8, Pyruvate kinase PKM, GTP-binding nuclear protein Ran, Prohibitin-2, Importin subunit alpha-1, Synapsin-3, Peroxisome biogenesis factor 1, Nibrin, DnaJ homolog subfamily B member 6, DnaJ homolog subfamily B member 3, DnaJ homolog subfamily B member 8, DnaJ homolog subfamily B member 2, Cystatin-A; Cystatin-A, N-terminally processed, T-complex protein 1 subunit alpha, E3 ubiquitin-protein ligase TRIM21, Elongation factor 1-gamma, Double-strand break repair protein MRE11A, Heat shock protein 75 kDa (mitochondrial), Probable C-mannosyltransferase DPY19L1, Biogenesis of lysosome-related organelles complex 1 subunit 2, Nuclear pore complex protein Nup93, Leucine-rich repeat neuronal protein 4, Very-long-chain enoyl-CoA reductase, Peroxisomal sarcosine oxidase, Mitochondrial dicarboxylate carrier, Wings apart-like protein homolog, Cofilin-1, Destrin, Cofilin-2, Tubulin alpha-1B chain, Tubulin alpha-1A chain, Tubulin alpha-1C chain, Tubulin alpha-4A chain, Tubulin alpha-3C/D chain, Tubulin alpha-3E chain, Heat shock 70 kDa protein 1B, Heat shock 70 kDa protein 1A, Puromycin-sensitive aminopeptidase-like protein, Serine/arginine repetitive matrix protein 3, Protein PAT1 homolog 2, Centrosomal protein of 290 kDa, Zinc finger protein 25, ADAMTS-like protein 3, CAP-Gly domain-containing linker protein 4, EH domain-binding protein 1-like protein 1, Synaptotagmin-like protein 5, Guanine nucleotide exchange factor DBS, Nuclear transition protein 2, Protein bicaudal D homolog 1 and Putative helicase Mov10L1.

According to one embodiment, the polypeptide capable of increasing homologous recombination comprises a plurality of polypeptides.

According to one embodiment, the polypeptide capable of increasing homologous recombination comprises all viral peptides.

According to one embodiment, the polypeptide capable of increasing homologous recombination comprises all eukaryotic peptides.

According to one embodiment, the polypeptide capable of increasing homologous recombination comprises at least one viral peptide (e.g. one, two, three, four, five or more viral peptides) and at least one eukaryotic polypeptide (e.g. one, two, three, four, five or more eukaryotic peptides).

According to one embodiment, the first nucleic acid sequence and the second nucleic acid sequence of the recombinant system of some embodiments of the invention are translationally fused.

According to one embodiment, the translation product (e.g. polypeptide) of the first nucleic acid sequence and the translation product (e.g. polypeptide) of the second nucleic acid sequence form a fused molecule, e.g. a fusion protein.

As used herein, the term "fused" means that at least a protein or peptide is physically associated with another protein or peptide, which naturally don't form a complex. In some embodiments, fusion is typically by a covalent linkage, however, other types of linkages are encompassed in the term "fused" include, for example, linkage via an electrostatic interaction, or a hydrophobic interaction and the like. Covalent linkage can encompass linkage as a fusion protein or chemically coupled linkage, for example via a disulfide bound formed between two cysteine residues.

According to a specific embodiment the fused molecule is a "fusion polypeptide" or "fusion protein", a protein created by joining two or more heterologously related polypeptide sequences together. The fusion polypeptides encompassed in this invention include translation products of a chimeric nucleic acid construct that joins the DNA sequence encoding a DNA editing agent with the DNA sequence encoding a polypeptide capable of increasing HR to form a single open-reading frame. In other words, a "fusion polypeptide" or "fusion protein" is a recombinant protein of two or more proteins which are joined by a peptide bond.

The terms "fusion protein", "chimera", "chimeric molecule", or "chimeric protein" are used interchangeably.

According to one embodiment, the first nucleic acid sequence is fused to the second nucleic acid sequence at an N-terminus of the first nucleic acid sequence. An exemplary nucleic acid sequence of such a fusion is set forth in SEQ ID NO: 7.

According to one embodiment, the first nucleic acid sequence is fused to the second nucleic acid sequence at a C-terminus of the first nucleic acid sequence. An exemplary nucleic acid sequence of such a fusion is set forth in SEQ ID NO: 9.

According to a specific embodiment, when the first nucleic acid sequence and the second nucleic acid sequence are translationally fused, the encoded polypeptide comprises a fusion protein comprising a DNA editing agent having a double strand DNA cutting activity and a polypeptide capable of increasing homologous recombination.

According to a specific embodiment, when the first nucleic acid sequence and the second nucleic acid sequence are translationally fused, the encoded polypeptide comprises a Cas9-UL12 fusion protein (e.g. a fusion protein comprising Cas9 and amino acids 1-126 of an N-terminal fragment of UL12). Exemplary amino acid sequences of such fusion proteins are set forth in SEQ ID NOs: 8 and 10.

According to one embodiment, there is provided a proteinaceous system encoded by the recombinant system of some embodiments of the invention.

According to one embodiment, the proteinaceous system comprises at least two proteins (e.g. 2, 3, 4, 5 or more proteins) encoded by the recombinant system of some embodiments of the invention.

According to one embodiment, the proteinaceous system comprises a DNA editing agent having a double strand DNA cutting activity and a polypeptide capable of increasing homologous recombination.

According to one embodiment, the DNA editing agent having double strand DNA cutting activity and the polypeptide capable of increasing homologous recombination are joined or linked or fused, using recombinant techniques, at the amino-terminus or carboxyl-terminus.

According to one embodiment, the binding between the DNA editing agent having double strand DNA cutting activity and the polypeptide capable of increasing homologous recombination is a direct interaction, e.g. joining of the affinity binding pair attached thereto in the target cell.

According to one embodiment, the binding interaction can also be an indirect interaction, such as via a linker or spacer.

A "linker" or "spacer" refers to a molecule or group of molecules that covalently connects two molecules, such as an affinity binding pair first member and a second member, and serves to place the two molecules in a preferred configuration, e.g., so as to form a protein complex in the target cell.

According to one embodiment, a flexible linker is used to connect the DNA editing agent and the polypeptide capable of increasing homologous recombination. Such a flexible linker refers to a peptide linker of any length in which the amino acid composition minimizes the formation of rigid structure by interaction of amino acid side chains with each other or with the polypeptide backbone. Typically a "flexible linker" is rich in glycine.

According to one embodiment, each of the first nucleic acid sequence and the second nucleic acid sequence is translationally fused to a member of an affinity binding pair such that the DNA editing agent having double strand DNA cutting activity and the polypeptide capable of increasing homologous recombination form a protein complex in the target cell.

Any affinity binding pair known in the art may be used in accordance with some embodiments of the invention. Exemplary affinity binding pairs include, but are not limited to, biotin/avidin, biotin/streptavidin, antibody/antigen, and receptor/ligand.

According to a specific embodiment, the affinity binding pair is based on the biotin-streptavidin interaction.

According to a specific embodiment, the first member of the affinity binding pair (e.g. DNA editing agent having double strand DNA cutting activity or the polypeptide capable of increasing homologous recombination) is translationally fused to streptavidin, the second member of the affinity binding pair (e.g. the polypeptide capable of increasing homologous recombination or DNA editing agent, respectively) is translationally fused to biotin or a biotin derivative (e.g. desthiobiotin or iminobiotin).

An example of an affinity binding pair, which may be used according to some embodiments of the invention, is the rapamycin-induced interaction of FKBP and FBP. This system has been used successfully to reconstitute Cas9 activity when expressed as a split protein with halves fused to FKBP and FBP (B. Zetsche, S. E. Volz, F. Zhang, *Nat. Biotechnol.* 2015, 33, 139). A similar approach can be used to bring together the DNA editing agent and the protein capable of increasing homologous recombination.

An additional approach which may be used according to some embodiments of the invention is to use blue light inducible (470 nm) dimerization domains called pMagnets (F. Kawano, H. Suzuki, A. Furuya, M. Sato, *Nat. Commun.* 2015, 6, 6256).

As mentioned, the recombinant systems of some embodiments of the invention are for improving genome editing via homologous recombination in target cells. Methods of assessing genome editing via HR are discussed below.

According to one embodiment, the target cell is a eukaryotic cell.

The term "eukaryotic cell" as used herein refers to any cell of a eukaryotic organism. Eukaryotic organisms include single- and multi-cellular organisms. Single cell eukaryotic organisms include, but are not limited to, yeast, protozoans, slime molds and algae. Multi-cellular eukaryotic organisms include, but are not limited to, animals (e.g. mammals, insects, nematodes, birds, fish), plants, fungi and algae (e.g. brown algae, red algae, green algae).

According to one embodiment, the eukaryotic cell is a cell of a plant.

According to a one embodiment, the eukaryotic cell is an animal cell.

According to a one embodiment, the eukaryotic cell is a cell of a vertebrate.

According to a one embodiment, the eukaryotic cell is a cell of an invertebrate.

According to a one embodiment, the eukaryotic cell is a mammalian cell.

According to a specific embodiment, the mammalian cell is a cell of a non-human organism, such as but not limited to, a rodent, a rabbit, a pig, a goat, a sheep, a ruminant, a dog, a cat, a horse, and non-human primate.

According to a specific embodiment, the eukaryotic cell is a cell of human being.

According to one embodiment, the eukaryotic cell is a primary cell, a cell line, a stem cell, an embryonic stem cell, an adult stem cell, a hematopoietic stem cell, a mesenchymal stem cell or an induced pluripotent stem cell (iPS).

As used herein, the phrase "stem cells" refers to cells which are capable of remaining in an undifferentiated state (e.g., totipotent, pluripotent or multipotent stem cells) for extended periods of time in culture until induced to differentiate into other cell types having a particular, specialized function (e.g., fully differentiated cells). Totipotent cells, such as embryonic cells within the first couple of cell divisions after fertilization are the only cells that can differentiate into embryonic and extra-embryonic cells and are able to develop into a viable human being. Preferably, the phrase "pluripotent stem cells" refers to cells, which can differentiate into all three embryonic germ layers, i.e., ectoderm, endoderm and mesoderm or remaining in an undifferentiated state. The pluripotent stem cells include embryonic stem cells (ESCs) and induced pluripotent stem cells (iPS). The multipotent stem cells include adult stem cells and hematopoietic stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763), embryonic germ (EG) cells which are obtained from the genital tissue of a fetus any time during gestation, preferably before 10 weeks of gestation, and cells originating from an unfertilized ova which are stimulated by parthenogenesis (parthenotes).

The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage.

It will be appreciated that commercially available stem cells can also be used according to some embodiments of the invention. Human ES cells can be purchased from the NIH human embryonic stem cells registry [www(dot)grants(dot)nih(dot)gov/stem_cells/registry/current(dot)htm].

In addition, embryonic stem cells can be obtained from various species, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

"Induced pluripotent stem cells" (iPS; embryonic-like stem cells) refers to cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation, which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [such as described in Park et al. Reprogramming of human somatic cells to pluripotency with defined factors. Nature (2008) 451:141-146].

The phrase "adult stem cells" (also called "tissue stem cells" or a stem cell from a somatic tissue) refers to any stem cell derived from a somatic tissue [of either a postnatal or prenatal animal (especially the human)]. The adult stem cell is generally thought to be a multipotent stem cell, capable of differentiation into multiple cell types. Adult stem cells can be derived from any adult, neonatal or fetal tissue such as adipose tissue, skin, kidney, liver, prostate, pancreas, intestine, bone marrow and placenta.

According to one embodiment, the stem cells utilized by some embodiments of the invention are bone marrow (BM)-derived stem cells including hematopoietic, stromal or mesenchymal stem cells [Dominici, M et al., (2001) J. Biol. Regul. Homeost. Agents. 15: 28-37]. BM-derived stem cells may be obtained from iliac crest, femora, tibiae, spine, rib or other medullar spaces.

Hematopoietic stem cells (HSCs), which may also referred to as adult tissue stem cells, include stem cells obtained from blood or bone marrow tissue of an individual at any age or from cord blood of a newborn individual. Preferred stem cells according to this aspect of some embodiments of the invention are embryonic stem cells, preferably of a human or primate (e.g., monkey) origin.

Placental and cord blood stem cells may also be referred to as "young stem cells".

Mesenchymal stem cells (MSCs), the formative pluripotent blast cells, give rise to one or more mesenchymal tissues (e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Although such cells can be isolated from embryonic yolk sac, placenta, umbilical cord, fetal and adolescent skin, blood and other tissues, their abundance in the BM far exceeds their abundance in other tissues and as such isolation from BM is presently preferred.

Adult tissue stem cells can be isolated using various methods known in the art such as those disclosed by Alison, M. R. [J Pathol. (2003) 200(5): 547-50]. Fetal stem cells can be isolated using various methods known in the art such as those disclosed by Eventov-Friedman S, et al. [PLoS Med. (2006) 3: e215].

Hematopoietic stem cells can be isolated using various methods known in the arts such as those disclosed by "Handbook of Stem Cells" edit by Robert Lanze, Elsevier Academic Press, 2004, Chapter 54, pp 609-614, isolation and characterization of hematopoietic stem cells, by Gerald J Spangrude and William B Stayton.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

According to one embodiment, the eukaryotic cell is isolated from its natural environment (e.g. human body).

According to one embodiment, the eukaryotic cell is a healthy cell.

According to one embodiment, the eukaryotic cell is a diseased cell or a cell prone to a disease.

According to one embodiment, the eukaryotic cell is a cancer cell.

According to one embodiment, the eukaryotic cell is an immune cell, e.g. T cell (e.g. CAR-T cell), B cell, macrophage, NK cell, etc.

According to one embodiment, the eukaryotic cell is a cell infected by a pathogen (e.g. by a bacterial, viral or fungal pathogen).

According to one embodiment, the eukaryotic cell is a cell prone to a metabolic or genetic deficiency, disease or disorder (as discussed below).

The recombinant systems of some embodiments of the invention may be introduced into target cells (e.g. eukaryotic cells) using DNA delivery methods (e.g. by expression vectors) or using DNA-free methods.

According to one embodiment, the recombinant systems can be provided as RNA to the cell.

Thus, it will be appreciated that the present techniques relate to introducing the recombinant systems using DNA-free methods such as RNA transfection (e.g. mRNA transfection), or Ribonucleoprotein (RNP) transfection (e.g. protein-RNA complex transfection, e.g. Cas9-UL12-sgRNA complex).

According to a specific embodiment, the recombinant systems (e.g. comprising, for example, Cas9 and sgRNA) are provided using DNA delivery methods (e.g. via plasmid).

According to a specific embodiment, the recombinant systems (e.g. comprising, for example, Cas9 and sgRNA) are provided using DNA-free delivery methods (e.g. via RNA transfection).

According to a specific embodiment, the recombinant systems (e.g. comprising, for example, Cas9) are provided as polypeptides.

According to a specific embodiment, the recombinant systems (e.g. comprising, for example, Cas9 and sgRNA) are provided as protein-RNA complex transfection.

According to one embodiment, for expression of recombinant systems of the invention in mammalian cells, a nucleic acid sequence encoding the DNA editing agent having double strand DNA cutting activity and a nucleic acid sequence encoding the polypeptide capable of increasing homologous recombination are ligated into at least one nucleic acid construct suitable for mammalian cell expression. Such a nucleic acid construct includes a promoter sequence for directing transcription of the nucleotide sequences in the target cell in a constitutive or inducible manner.

According to one embodiment, the nucleic acid sequence encoding the DNA editing agent having double strand DNA cutting activity and the nucleic acid sequence encoding the polypeptide capable of increasing homologous recombination are ligated into one nucleic acid construct.

According to one embodiment, the nucleic acid sequence encoding the DNA editing agent having double strand DNA cutting activity and the nucleic acid sequence encoding the polypeptide capable of increasing homologous recombination are ligated into two nucleic acid constructs. When two constructs are used, these may be introduced into the cell concomitantly or sequentially.

The nucleic acid construct (also referred to herein as an "expression vector") of some embodiments of the invention includes additional sequences which render this vector suitable for replication and integration in eukaryotes (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding the DNA editing agent and/or the polypeptide capable of increasing homologous recombination in a target cell can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A⁺, pMT010/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such, no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of recombinant systems since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This contrasts with vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into eukaryotic cells (e.g. stem cells). Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

According to one embodiment, the nucleic acid sequence encoding the DNA editing agent having double strand DNA cutting activity and the nucleic acid sequence encoding the polypeptide capable of increasing homologous recombination are encoded from the same expression vector. Such a vector may comprise a single cis-acting regulatory element active in eukaryotic cells (e.g., promoter) for expression of both the DNA editing agent (e.g. nuclease and the DNA recognition unit) and the polypeptide capable of increasing homologous recombination. Alternatively, the DNA editing agent (e.g. nuclease and the DNA recognition unit) and the polypeptide capable of increasing homologous recombination may each be operably linked to a cis-acting regulatory element active in eukaryotic cells (e.g., promoter).

According to one embodiment, the DNA editing agent (e.g. nuclease and the DNA recognition unit) and the polypeptide capable of increasing homologous recombination are encoded from different expression vectors whereby each is operably linked to a cis-acting regulatory element active in eukaryotic cells (e.g., promoter).

According to one embodiment, the expression vector comprises a single nucleic acid sequence encoding the DNA editing agent (e.g. nuclease and the DNA recognition unit).

According to one embodiment, the expression vector comprises multiple (e.g. 2, 3, 4, 5, 6, 7, 8, 9, 10 or more) nucleic acid sequences encoding the DNA editing agent (e.g. nuclease and the DNA recognition unit).

According to one embodiment, the expression vector comprises a single nucleic acid sequence encoding the polypeptide capable of increasing homologous recombination (e.g. UL12, homolog or fragment thereof).

According to one embodiment, the expression vector comprises multiple (e.g. 2, 3, 4, 5, 6, 7, 8, 9, 10 or more) nucleic acid sequences encoding the polypeptide capable of increasing homologous recombination (e.g. UL12, homolog or fragment thereof).

According to a specific embodiment, the expression vector comprises a nucleic acid sequence encoding Cas9 and multiple nucleic acid sequences encoding UL12, a homolog or fragment thereof (e.g. a 1-126 aa segment or a 50-126 aa segment as discussed in detail above).

According to a specific embodiment, multiple nucleic acid sequences (e.g. 2 or more) encoding the UL12, homolog or fragment thereof, are placed on both the N- and C-terminus of Cas9. Alternatively, multiple nucleic acid sequences (e.g. 2 or more) encoding the UL12, homolog or fragment thereof, are placed in tandem onto the N- or C-terminus.

One of skill in the art is capable of making such a determination, especially in light of the detailed disclosure provided herein.

One of skill in the art is capable of making such a determination, especially in light of the detailed disclosure provided herein.

According to one embodiment, there is provided a composition (also referred to as reagent) comprising the recombinant system, proteinaceous system or nucleic acid construct or construct system of some embodiments of the invention.

According to one embodiment, there is provided a method of increasing genome editing in a targeted manner in a target cell, the method comprising subjecting the target cell to a genome editing reagent comprising the system or nucleic acid construct or construct system of some embodiments of the invention.

According to one embodiment, the method of the invention increases genome editing via homologous recombination by at least about 10%, 20%, 30%, 40%, 50%, 60%, 70%, 80%, 90%, 100% or more, as compared to genome editing in the absence of the recombinant system of the invention. Methods of assessing genome editing are discussed below.

According to one embodiment, subjecting is effected in vivo.

According to one embodiment, subjecting is effected ex vivo.

According to one embodiment, subjecting is effected in vitro.

According to one embodiment, the homologous recombination is associated with a modification selected from the group consisting of a deletion, an insertion, a point mutation and a combination thereof (e.g. insertion-deletion (Indel)).

According to one embodiment, the modification comprises a modification of at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 150, 250, 500, 1000, 1500, 2000, 3000, 4000 or at most 5000 nucleotides.

According to one embodiment, the modification comprises a deletion.

According to one embodiment, the deletion comprises a deletion of at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 150, 250, 500, 1000, 1500, 2000, 3000, 4000 or at most 5000 nucleotides.

According to one embodiment, the deletion comprises a deletion of an entire gene.

According to one embodiment, the modification comprises a point mutation.

According to one embodiment, the point mutation comprises a point mutation in at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 150, 250, 500, 1000, 1500, 2000, 3000, 4000 or at most 5000 nucleotides.

According to one embodiment, the modification comprises an insertion.

According to one embodiment, the insertion comprises an insertion of at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 150, 250, 500, 1000, 1500, 2000, 3000, 4000 or at most 5000 nucleotides.

According to one embodiment, the insertion comprises an insertion of an entire gene.

According to a specific embodiment, the modification is a mutation in the coding sequence of a gene, e.g. changing a wild-type sequence to a mutated sequence.

According to a specific embodiment, the modification is a reversion in the coding sequence of a gene, e.g. reverting a mutant sequence to a wild-type sequence.

According to a specific embodiment, the modification is an addition or deletion of a gene segment, e.g. giving rise to a protein with an added domain (natural or artificial), or a deletion.

According to a specific embodiment, the modification is in a non-coding element of a gene, e.g. creating mutations, deletions, or insertions in non-coding elements, including promoter regions, enhancer regions, transcription start sites, translation start sites, splice sites, introns, terminator regions, 5' and 3' UTR regions (of the encoded mRNA). Such edited changes can affect, for example, mRNA expression, stability, splicing, export, translation.

According to a specific embodiment, the modification is an epigenetic modification in the genomic region, with implications for expression of genes at that locus.

According to a specific embodiment, the modification targets non-coding RNAs, including e.g. tRNAs, ribosomal RNAs, other RNAs with non-protein-coding functions.

According to a specific embodiment, the modification targets genes of regulatory non-coding RNAs, such as miRNAs, which can affect for example the target genes of those miRNAs.

According to a specific embodiment, the modification alters miRNA recognition sites of target genes, e.g. changing expression of those genes.

According to a specific embodiment, the modification changes chromatin architecture, for example by targeting CTCF binding sites, with impact on gene expression in the targeted chromatin domain.

According to one embodiment, when the modification is an insertion, the method further comprises introducing into the target cell donor oligonucleotides.

As used herein, the term "donor oligonucleotides" or "donor oligos" refers to exogenous nucleotides, i.e. externally introduced into the target cell to generate a precise change in the genome. According to one embodiment, the donor oligonucleotides are synthetic.

According to one embodiment, the donor oligonucleotides are RNA oligonucleotides.

According to one embodiment, the donor oligonucleotides are DNA oligonucleotides.

According to one embodiment, the donor oligonucleotides comprise single-stranded donor oligonucleotides (ssODN).

According to one embodiment, the donor oligonucleotides comprise double-stranded donor oligonucleotides (dsODN).

According to one embodiment, the donor oligonucleotides comprise double-stranded DNA (dsDNA).

According to one embodiment, the donor oligonucleotides comprise single-stranded DNA (ssDNA).

According to one embodiment, the donor oligonucleotides comprise double-stranded RNA (dsRNA).

According to one embodiment, the donor oligonucleotides comprise single-stranded RNA (ssRNA).

According to one embodiment, the donor oligonucleotides are provided in a non-expressed vector format or oligo.

According to one embodiment, the donor oligonucleotides are provided in a DNA donor plasmid.

According to one embodiment, the donor oligonucleotides are provided in a cosmid.

According to one embodiment, the donor oligonucleotides are provided by a viral vector (e.g. one derived from AAV).

According to one embodiment, the donor oligonucleotides comprise about 1-20, 1-30, 1-40, 1-50, 1-60, 1-70, 1-80, 1-90, 1-100, 1-150, 1-250, 1-500, 2-3, 2-4, 2-5, 2-10, 2-20, 2-40, 5-10, 5-25, 5-50, 5-75, 5-100, 5-250, 5-500, 10-15, 10-20, 10-50, 10-100, 10-250, 10-500, 50-100, 50-250, 50-500, 100-200, 100-500, 100-1000, 250-500, 250-750, 250-1000, 500-750, 500-1000, 750-1000, 1000-2500, 1000-5000, or 1000-10000 nucleotides.

According to one embodiment, introducing into the eukaryotic cell donor oligonucleotides is effected using any of the methods described above (e.g. using the expression vectors or RNP transfection).

According to one embodiment, there is provided a composition comprising at least one DNA editing agent having double strand DNA cutting activity, at least one polypeptide capable of increasing homologous recombination and DNA donor oligonucleotides for genome editing.

Regardless of the transformation/infection method employed, the present teachings further select transformed cells comprising a genome editing event.

According to a specific embodiment, selection is carried out such that only cells comprising a successful accurate modification (e.g. insertion, deletion, point mutation) in the specific locus are selected. Accordingly, cells comprising any event that includes a modification (e.g. an insertion, deletion, point mutation) in an unintended locus are not selected.

According to one embodiment, selection of modified cells can be performed at the phenotypic level, by detection of a molecular event, by detection of a fluorescent reporter, or by growth in the presence of selection (e.g., antibiotic).

According to one embodiment, selection of modified cells is performed by analyzing eukaryotic cells or clones comprising the genome editing event (e.g. genome editing via HR) also referred to herein as "mutation" or "edit", dependent on the type of editing sought e.g., insertion, deletion, insertion-deletion (Indel), inversion, substitution and combinations thereof.

Methods for detecting sequence alteration are well known in the art and include, but not limited to, DNA sequencing (e.g., next generation sequencing), electrophoresis, an enzyme-based mismatch detection assay and a hybridization assay such as PCR, RT-PCR, RNase protection, in-situ hybridization, primer extension, Southern blot, Northern Blot and dot blot analysis. Various methods used for detection of single nucleotide polymorphisms (SNPs) can also be used, such as PCR based T7 endonuclease, Hetroduplex and Sanger sequencing, or PCR followed by restriction digest to detect appearance or disappearance of unique restriction site/s.

According to one embodiment, selection of modified cells is effected by flow cytometry (FACS) selecting modified cells exhibiting fluorescence emitted by a fluorescent reporter. Following FACS sorting, positively selected pools of transformed cells, displaying the fluorescent marker are collected and an aliquot can be used for testing the genome editing event as discussed above.

In cases where antibiotic selection marker was used, following modification, cells are cultivated in the presence of selection (e.g., antibiotic), e.g. in a cell culture. A portion of the cells of the cell culture are then analyzed (validated) for the genome editing event, as discussed above.

It will be appreciated that positively selected cells can be homozygous or heterozygous for the genome editing event. The skilled artisan will select the cells for further culturing/regeneration according to the intended use.

Positive cell clones (e.g. eukaryotic cells) may be stored (e.g., cryopreserved).

Alternatively, eukaryotic cells may be further cultured and maintained, for example, in an undifferentiated state for extended periods of time or may be induced to differentiate into other cell types, tissues, organs or organisms as required.

The recombinant system or nucleic acid construct or construct system of some embodiments of the invention (and optionally the donor oligos of some embodiments of the invention) can be administered to a single cell, to a group of cells (e.g. primary cells or cell lines as discussed above) or to an organism (e.g. mammal, as discussed above).

Accordingly, the recombinant system, proteinaceous system or nucleic acid construct or construct system of some embodiments of the invention can be administered to an organism per se, or in a pharmaceutical composition where it is mixed with suitable carriers or excipients.

As used, herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the recombinant system accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations, which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (recombinant system) effective to prevent, alleviate or ameliorate symptoms of a disorder (e.g., cancer, genetic disease or disorder, immune deficiency, metabolic disorder) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Animal models for cancerous diseases are described e.g. in Yee et al., *Cancer Growth Metastasis*. (2015) 8(Suppl 1): 115-118. Animal models for infectious diseases are described e.g. in Shevach, *Current Protocols in Immunology*, Published Online: 1 Apr. 2011, DOI: 10.1002/0471142735.im1900s93.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to one aspect of the invention there is provided a method of treating a disease or disorder amenable to treatment by homologous recombination in a subject in need thereof, the method comprising administering to the subject the recombinant system, proteinaceous system or nucleic acid construct or construct system of some embodiments of the invention.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" or "subject in need thereof" includes animals, including mammals, preferably human beings, at any age or gender which suffer from the pathology. Preferably, this term encompasses individuals who are at risk to develop the pathology.

According to one embodiment, the disease or disorder is a cancer, an infection, an inflammation, an autoimmune disease, a genetic disease or disorder, an immune deficiency, and a metabolic disorder.

According to one aspect of the invention the system, the nucleic acid construct or the construct system of some embodiments of the invention can be used in treating a disease or disorder amenable to treatment by homologous recombination in a subject in need thereof, wherein the disease or disorder is selected from the group consisting of a cancer, an infection, an inflammation, an autoimmune disease, a genetic disease or disorder, an immune deficiency, and a metabolic disorder.

Cancerous Diseases

Non-limiting examples of cancers which can be treated by the method of some embodiments of the invention can be any solid or non-solid cancer and/or cancer metastasis or precancer, including, but is not limiting to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibro sarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to one embodiment, the cancer, which can be treated by the method of some embodiments of the invention, comprises a hematologic malignancy.

According to one embodiment, in order to treat or prevent a cancerous disease in a subject, the genome editing event is designed to target a gene of interest associated with onset or progression of the cancerous disease.

Exemplary genes to be targeted in cancer include, but are not limited to, p53 family, PTEN, BCR-ABL, HRAS, KRAS, BRAF, RUNX1/ETO, CTNNB1 (beta-catenin), APC, YAP, ErbB-1, ErbB-2, ErbB-3, ErbB-4, PIK3CA, and IDH1.

Assessing the efficacy of treatment may be carried out using any method known in the art, such as by assessing the tumor growth or the number of neoplasms or metastases, e.g. by MRI, CT, PET-CT, by blood tests, ultrasound, x-ray, etc.

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

According to one embodiment, in order to treat or prevent an infectious disease in a subject, the genome-editing event is designed to target a gene of interest associated with onset or progression of the infectious disease.

Exemplary genes to be targeted in infectious diseases include, but are not limited to, HBV polymerase, HBV core, the pol genes and capsid genes of viruses such as CMV, HSV, VZV EBV, HIV, and toxin genes (e.g. cholera toxin).

Assessing the efficacy of treatment may be carried out using any method known in the art, such as by assessing the subject's physical well-being, by blood tests, by assessing viral/bacterial load, etc.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

According to one embodiment, in order to treat or prevent an inflammatory disease in a subject, the genome editing event is designed to target a gene of interest associated with onset or progression of the inflammatory disease.

Exemplary genes to be targeted for inflammatory diseases include, but are not limited to, GATA-3, FoxP3, and T-bet.

Assessing the efficacy of treatment may be carried out using any method known in the art, such as by assessing the subject's physical well-being, by blood tests, etc.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost.2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189). Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl:S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus *foliaceus*.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to one embodiment, in order to treat or prevent an autoimmune disease in a subject, the genome editing event is designed to target a gene of interest associated with onset or progression of the autoimmune disease.

Exemplary genes to be targeted for autoimmune diseases include, but are not limited to, antibody loci in B-cell clones producing auto-antibodies, genes associated with T-cell receptors in auto-reactive T-helper cells, genes associated with induction of Foxp3, CD28 in Treg cells.

Assessing the efficacy of treatment may be carried out using any method known in the art, such as by assessing the subject's physical well-being, by blood tests, bone marrow aspirate, etc.

Genetic Diseases or Disorders

Include, but are not limited to, monogenic recessive disorder i.e. disease or condition caused as a result of a single defective gene on the autosomes.

According to one embodiment, the monogenic recessive disorder is a result of a spontaneous or hereditary mutation.

According to one embodiment, the monogenic recessive disorder is autosomal dominant, autosomal recessive or X-linked recessive.

Exemplary monogenic recessive disorders include, but are not limited to, severe combined immunodeficiency (SCID), hemophilia, enzyme deficiencies, Parkinson's Disease, Wiskott-Aldrich syndrome, Cystic Fibrosis, Phenylketonuria, Friedrich's Ataxia, Duchenne Muscular Dystrophy, Hunter disease, Aicardi Syndrome, Klinefelter's Syndrome, Leber's hereditary optic neuropathy (LHON).

Exemplary genes to be targeted in genetic diseases and disorders include, but are not limited to, the human beta-globin gene (e.g. for sickle cell disease and beta-thalassemia), ADA (e.g. for SCID), DMD (e.g. for Duchenne Muscular Dystrophy), WAS, WASL (e.g. for Wiskott-Aldrich syndrome), and CFTR (e.g. for Cystic Fibrosis).

Assessing the efficacy of treatment may be carried out using any method known in the art, such as by assessing the subject's physical well-being, by blood tests, bone marrow aspirate, etc.

Immune Deficiencies

Include, but are not limited to, primary immunodeficiency disorders, e.g. X-linked agammaglobulinemia (XLA), common variable immunodeficiency (CVID), severe combined immunodeficiency (SCID); secondary immunodeficiency disorders e.g. Acquired Immunodeficiency Syndrome (AIDS), cancers of the immune system (e.g. leukemia), immune-complex diseases (e.g. viral hepatitis) and multiple myeloma, and aplastic anemia.

Exemplary genes to be targeted in immune deficiencies include, but are not limited to, ADA (e.g. for SCID), WAS, WASL (e.g. for Wiskott-Aldrich syndrome), and HIV pol (e.g. for AIDS).

Assessing the efficacy of treatment may be carried out using any method known in the art, such as by assessing the subject's physical well-being, by blood tests, bone marrow aspirate, etc.

Metabolic Diseases and Disorders

Include, but are not limited to, obesity, type II diabetes, X syndrome (Metabolic Syndrome), metabolic osteopathy, inherited metabolic diseases e.g. Lysosomal storage disorders (e.g. Hurler syndrome, Niemann-Pick disease, Tay-Sachs disease, Gaucher disease, Fabry disease, Krabbe disease), Galactosemia, Maple syrup urine disease, Phenylketonuria (PKU), Glycogen storage disease, Mitochondrial disorders, Friedreich ataxia, Peroxisomal disorders (e.g. Zellweger syndrome, Adrenoleukodystrophy), Metal metabolism disorders (e.g. Wilson disease, Hemochromatosis), Organic acidemias (e.g. methylmalonic acidemia and propionic acidemia), and Urea cycle disorders (e.g. ornithine transcarbamylase deficiency and citrullinemia).

Exemplary genes to be targeted in metabolic diseases and disorders include, but are not limited to, HEXA (e.g. for Tay-Sachs); SMPD1, NPC1, NPC2 (e.g. for Niemann-Pick disease); PAH (e.g. for Phenylketonuria).

Assessing the efficacy of treatment may be carried out using any method known in the art, such as by assessing the subject's physical well-being, by blood tests, bone marrow aspirate, etc.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 1 is expressed in a DNA sequence format (e.g., reciting T for thymine), but it can refer to either a DNA sequence that corresponds to an Cas9 nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Cells and Cell Culture

Human embryonic kidney cells HEK 293 and HEK 293FT, HCT116, and BHK cells were grown in Dulbecco's modified Eagle's medium (DMEM; GIBCO, Life Technologies, Thermo Scientific, Waltham, Mass.) supplemented with 8% fetal bovine serum (GIBCO), 100 units/ml penicillin, 100 µg/ml streptomycin and cultured at 37° C. in a humidified incubator with 5.6% $CO_2$. MCF10A were grown in DMEM/F12 (Biological Industries) supplemented with 5% donor horse serum (GIBCO), 2 mM glutamine (Biological Industries), 20 ng/ml epidermal growth factor (EGF), 10 µg/ml insulin, 0.5 µg/ml hydrocortisone, 100 ng/ml cholera toxin (all from Sigma), and antibiotics, as above. Light microscopy photographs of cells were performed using an Olympus (Tokyo, Japan) IX70 microscope connected to a DVC camera. The XTT assay (Biological Industries) was used to quantify cell proliferation and viability. For counting of cell colonies, cells were fixed in cold methanol, and stained with 0.1% crystal violet in 25% methanol, followed by extensive washing with water.

A temperature sensitive baby hamster kidney cell line, BHK21 ts13, was used with a well-defined point mutation, G690D, in the $TAF_{II}$-250 (TAF1) gene on the X chromosome, as previously described (Hayashida et al., 1994, below).

HEK293 cells were edited to produce temperature sensitive (TAF1 G716D ts) cells. Specifically, CRISPR editing was carried out in HEK293 cells to make the same mutation that was identified in the BHK21 ts13. Of note, in human cells, this is TAF1 G716D in exon 13 of the TAF1 gene on the X chromosome.

Recombinant Cas9 Production & Purification pET-28b-Cas9-His (Addgene_47327) [Gagnon, J. A. et al, *PloS one* (2014) 9: e98186] was modified to contain N-terminal SV40 NLS and C-terminal Nucleoplasmin NLS. Two tags were fused in frame with Cas9; 3×FLAG tag at the N-terminus and His6 at the C-terminus of the protein. The resulting construct was used as a control and served as the template in which the UL12 sequences (126 AA) were introduced upstream or downstream to Cas9. Engineering of all constructs were performed either by RF cloning [as discussed in Unger, T. et al., *Journal of structural biology* (2010) 172: 34-44] or by Inverse PCR [as discussed in Hemsley, A. et al., *Nucleic acids research* (1989) 17: 6545-6551]. The resulting vectors were transformed into *E. coli* Rosetta 2 pLys-S competent cells. Cultures were grown at 37° C. Protein expression was induced by the addition of isopropyl-β-d-thiogalactopyranoside (IPTG; 200 µM), and the culture was kept at 15° C. overnight. Cells were harvested by centrifugation, and the pellet was resuspended in 100 ml lysis buffer. After lysis by protein disrupter (Constant Systems), the soluble fraction was obtained by centrifugation and purified by immobilized metal ion affinity chromatography (IMAC) using a HiTrap FF_5 ml cartridge (GE Healthcare) using an FPLC system (ÄKTA GE Healthcare Life Sciences). Cas9 variants were eluted in one step with the binding buffer supplemented with 0.5 M Imidazole and injected directly into a size exclusion column (HiLoad_16/60 Superdex 200) equilibrated with 20 mM Tris 8, 200 mM KCl and 10 mM MgCl2. All peak fractions were analyzed for the presence of Cas9 using SDS-PAGE, and the purity was estimated to be more than 90%. To obtain higher purity, the pooled fractions were diluted with 20 mM HEPES pH=7.5, 100 mM KCl and applied to a cation exchange column (Tricorn MonoS 10/30 GL, GE Healthcare) equilibrated with the dilution buffer. The protein was eluted with the same buffer using a gradient to 1 M KCl. The final pure enzyme was concentrated and supplemented with 50% glycerol and stored at −20° C.

RNA Preparation

MegaScript T7 transcription kit (Invitrogen) was used to prepare RNA from PCR-amplified amplicons or plasmid templates, followed by purification using TriReagent (Bio-Tri, BioLabs).

Plasmids, Transfection, Transduction and mRNA Analysis

The spCas9/sgRNA expression plasmids were based on Addgene plasmid #64324 (pU6-(BbsI) CBh-Cas9-T2A-mCherry (Addgene plasmid #64324) (Chu et al., 2015). The site for insertion of the guide RNA sequences was modified, using BsaI sites for cleavage, but resulting in the same sticky ends as the original plasmid. The sequence encoding the first 126 aa of HSV-1 UL12 was amplified from pSAKUL12/12.5 (Reuven et al., 2004) using PCR, and cloned into the pU6-(BbsI)_CBh-Cas9-T2A-mCherry backbone fused to the N-terminus of Cas9 (U3 construct), or fused to the C-terminus of Cas9 (U4 construct), upstream of the T2A peptide sequence. Plasmid donor DNA constructs used pBlueScript KS- as a backbone. The homology arm DNA was amplified by PCR from the cell lines' genomic DNA and cloned into the pBluescript backbone with restriction sites flanking the homology arms to aid in cloning and for insertion of the fragment encoding the fluorescent protein or other cassettes. The sequence for YFP (yellow fluorescent protein) was amplified from pSYFP2-C1 (pSYFP2-C1 (Addgene plasmid #22878) (Kremers et al., 2006). The sequence for the puromycin resistance gene was amplified from pEFIRES (Hobbs et al., 1998). Transfections were done by the calcium phosphate method as described (Levy et al., 2007) or JetPEI® (Polyplus-transfection SA, Illkirch, France). RNA transfections were done with Lipofectamine MessengerMAX, and protein/RNA transfections with Lipofectamine 2000 (ThermoFisher), as discussed below.

Transfection Conditions

A) RNA transfection was carried out using Lipofectamine MessengerMAX. Cells were plated in 96 well dishes. Per well: 75 ng Cas9 mRNA, 30 ng sgRNA, 0.36 pmol ssODN.

B) Ribonucleoprotein (RNP) transfection was carried out using Lipofectamine 200. Cells in 48 well plates were transfected. Per well: Cas9 (250 ng) and gRNA (62.5 ng) were mixed with Opti-MEM and incubated for 5 min. Then SSODN (250 ng) was added (final volume 12.5 µl of Opti-MEM). Lipofectamine (0.75 µl in 12.5 µl Opti-MEM) was added to protein/RNA/DNA mix, followed by pipetation, and the mixture was incubated for 25 min at RT, then added to the cells.

C) Cells in a 24 well plate were transfected using jet PEI with 200 pg of Cas9/sgRNA-encoding plasmids, 5 pmol ssODN, and pBluescript to bring the final amount to 0.75 µg total DNA.

HDR/NHEJ Assay

HEK293FT cells harboring a single copy of a reporter gene cassette were transfected with Cas9/sgRNA using the methods outlined above, together with ssODN donor template that encodes a point mutation changing the fluorescence of the reporter from blue to green, indicating HDR. The Cas9 and sgRNA were delivered using A) RNA transfection of in vitro transcribed RNAs; B) transfection of recombinant Cas9 protein complexed with in vitro transcribed sgRNA; C) plasmids encoding Cas9 driven by a CBh promoter, and sgRNA by the U6 promoter. Cells were transfected in quadruplicate, and were re-plated 2 days post-transfection. Cells were passaged 1-2 more times, and harvested for FACS analysis, with 100,000 cells analyzed per point. Cells edited by HDR express GFP, cells edited by NHEJ resulting in indels express neither BFP (Blue Fluorescent Protein) nor GFP (Green Fluorescent Protein).

```
List of sgRNA used in the experiments
Guide RNA targeting PSMB6 C-terminus:
                                        (SEQ ID NO: 18)
TAGAATCCCAGGATTCAGGC GGG Guide RNA targeting ABL:
                                        (SEQ ID NO: 19)
AGATGCTACTGGCCGCTGAA GGG Guide RNA targeting p73 (FIG. 4b):
                                        (SEQ ID NO: 20)
CTGGGCCATCTTCCCCACGC CGG Guide RNA targeting the mutant TAFII250 in BHK21
ts13 cells:
                                        (SEQ ID NO: 21)
ATTAATGATGCAAGTTGaCA TGG Guide for targeting human TAF1, amino acid 716:
TAF1_g1_fw:
                                        (SEQ ID NO: 23)
caccGGACCCTTAATGATGCAGGT TAF1_g1_re:
                                        (SEQ ID NO: 24)
aaacACCTGCATCATTAAGGGTCC Guide targeting the mutant human TAF1:
humTAF1_tsmut_g2_fw:
                                        (SEQ ID NO: 25)
caccgCTTAATGATGCAGGTTGaCA humTAF1_tsmut_g2_re:
                                        (SEQ ID NO: 26)
aaacTGtCAACCTGCATCATTAAGc Control guide non-targeting in human:
BFP_g2_fw:
                                        (SEQ ID NO: 27)
caccgCTGCACGCCGTGGGTCAGGG BFP_g2_re:
                                        (SEQ ID NO: 28)
aaacCCCTGACCCACGGCGTGCAGc List of ssODN used in the experiments
ssODN template for correcting the mutation in the
BHK21 ts13 cells:
                                        (SEQ ID NO: 22)
TTAAGCCCAGACTCACCCGCTTATAGTAGTTTTTTATCTTGGTTGCCATG

CCAACTTGCATCATTAATGGTCCATTTTCCTCACTGTATTCTGCAAGAAT ssODN for creating ts mutation (G716D) in human
TAF1:
                                        (SEQ ID NO: 29)
TCTGAGCAGAGACTCACCCGTTTATAATAGTTCTTTATCTTGGTTGCCAT GtCAACCTGCATCATTAAGGGTCCATTTTCCTCACTATATTCTGCAAGAA

TAA
```

-continued ssODN for correcting ts mutation to make wt human TAF1:

(SEQ ID NO: 30)
CTGAGCAGAGACTCACCCGTTTATAATAGTTCTTTATCTTGGTTGCCATG

CCAACCTGCATCATTAAGGGTCCATTTTCCTCACTATATTCTGCAAGAAT

Control ssODN:

(SEQ ID NO: 31)
ACCGGCAAGCTGCCCGTGCCCTGGCCCACCCTCGTGACCACCCTGACAT

ACGGCGTGCAGTGCTTCAGCCGCTACCCCGACCACATGAAGCAGCACG

AC

List of Primers Used in the Experiments
Primers flanking the TAF1 guide site, to amplify 554 bp fragment:

```
TAF1_hum_gen554_fw:
gcagaacccatacatggatatggagg    (SEQ ID NO: 32)

TAF1_hum_gen554_re:
tatggtatatgttcacagattaccag    (SEQ ID NO: 33)
```

Immunoblot and Co-Immunoprecipitation Studies

Immunoblots and immunoprecipitations (IPs) were done as previously described (Levy et al., 2007). Antibodies used were: anti-β-actin and anti-FLAG M2 (Sigma, St. Louis, Mo.); anti-Mre11, anti-Rad50, anti-Nbs1 (Santa Cruz Biotechnology, Santa Cruz, Calif.), anti-GFP (Living Colors) (Clontech). For immunoprecipitation (IP) of Flag-tagged proteins, anti-Flag M2 agarose (Sigma) was used. Horseradish peroxidase-conjugated secondary antibodies were from Jackson ImmunoResearch Laboratories, West Grove, Pa. Enhanced chemiluminescence was performed with the EZ-ECL kit (Biological Industries, Kibbutz Beit Haemek, Israel) and signals were detected by the ImageQuant LAS 4000 (GE Healthcare, Piscataway, N.J.). Intensities of bands were quantified by the ImageQuant TL software. For comparison of multiple experiments, values within one experiment were normalized to a standard set at 1. "SEM" refers to standard error of the mean.

Immunoprecipitation—Mass Spectrometry

HEK293 cells were transfected with constructs expressing Flag-mCherry (control), Flag-Cas9, and the Flag-tagged U3 and U4 constructs. Cells were harvested two days post-transfection, and the immunoprecipitation was performed with anti-Flag M2 agarose (Sigma). Duplicate samples were analyzed by SDS-PAGE, or prepared for analysis by the Mass Spectrometry Unit at the INCPM. Mass Spectrometry sample preparation: The samples were lysed and digested with trypsin using the S-trap method. Liquid chromatography mass spectrometry: The resulting peptides were analyzed using nanoflow liquid chromatography (nanoAcquity) coupled to high resolution, high mass accuracy mass spectrometry (Q Exactive HF). Each sample was analyzed on the instrument separately in a random order in discovery mode. Data processing: Raw data was processed with MaxQuant v1.6.0.16. The data was searched with the *Andromeda* search engine against the human proteome database appended with common lab protein contaminants and the following modifications: carbamidomethylation of cysteine, oxidation of methionine and acetylation of protein N terminal. Quantification was based on the LFQ method, based on unique/all peptides.

Flow Cytometry

Live cells were harvested and washed with PBS. For each measurement, 100,000 cells were collected by the BD LSRII flow cytometer (Becton Dickinson, Mountain View, Calif., USA) and analyzed with the BD FACSDiva software (BD Biosciences).

Example 1

Generation of Chimeric Cas9 Capable of Recruiting Cellular Repair Machinery

A CRISPR/Cas9 system was used based on the pX330 vector previously described (Cong et al., 2013) comprising further refinement (i.e. the addition of T2A-mCherry at the C-terminus of Cas9) as previously described (Chu et al., 2015). This vector expresses both the active Cas9 (Flag-tagged, and with NLS sequences at the N- and C-termini of Cas9) and the sgRNAs. The site for cloning the sgRNA was changed, so that BsaI was used for cloning, but the sticky ends produced by this cleavage and the surrounding sequences were the same as in the parent vectors. The 1-126 aa N-terminal fragment of UL12 was fused to the N- and C-termini of the Cas9 constructs, producing the constructs shown in FIG. 1A. The 126 aa N-terminal region of UL12 was previously shown to recruit the MRN complex (Balasubramanian et al., 2010). The present inventors confirmed that the U3 and U4 chimeric Cas9 constructs co-immunoprecipitated with the endogenous Mre11, Rad50, and Nbs1, while the original Cas9 did not (FIG. 1B). In this experiment, a guide non-specific to the human genome was used, so that the Cas9/sgRNA complexes were not expected to generate a double-strand break.

Mass Spectrometry analysis was performed on duplicates of samples that were analyzed by SDS-PAGE in FIG. 1B. In total, the present inventors identified and quantified 415 proteins (the typical range is 300-700). Table 1 shows a list of proteins that were enriched at least two-fold in the U3 or U4 samples, as compared to wild-type Cas9.

TABLE 1

Proteins interacting with U3 or U4 chimeric Cas9

| | Protein name | Gene name |
|---|---|---|
| 1 | Single-stranded DNA-binding protein, mitochondrial | SSBP1 |
| 2 | Nuclear cap-binding protein subunit 1 | NCBP1 |
| 3 | Heat shock protein HSP 90-beta; Putative heat shock protein HSP 90-beta-3; Heat shock protein HSP 90-alpha | HSP90AB1; HSP90AB3P; HSP90AA1 |
| 4 | Transmembrane protein 263 | TMEM263 |
| 5 | ATP synthase subunit gamma, mitochondrial | ATP5C1 |
| 6 | Mitochondrial 2-oxoglutarate/malate carrier protein | SLC25A11 |
| 7 | Complement component 1 Q subcomponent-binding protein, mitochondrial | C1QBP |
| 8 | Mitochondrial import receptor subunit TOM22 homolog | TOMM22 |
| 9 | Serine/threonine-protein phosphatase PGAM5, mitochondrial | PGAM5 |
| 10 | Voltage-dependent anion-selective channel protein 2 | VDAC2 |
| 11 | Histone H1.3 | HIST1H1D |
| 12 | Protein WWC2 | WWC2 |

TABLE 1-continued

Proteins interacting with U3 or U4 chimeric Cas9

| | Protein name | Gene name |
|---|---|---|
| 13 | Transmembrane protein 33 | TMEM33 |
| 14 | HIG1 domain family member 1A, mitochondrial | HIGD1A |
| 15 | CDK5 regulatory subunit-associated protein 2 | CDK5RAP2 |
| 16 | Eukaryotic translation elongation factor 1 epsilon-1 | EEF1E1 |
| 17 | DNA repair protein RAD50 | RAD50 |
| 18 | Sideroflexin-4 | SFXN4 |
| 19 | Importin subunit alpha-4 | KPNA3 |
| 20 | E3 ubiquitin-protein ligase RBX1; E3 ubiquitin-protein ligase RBX1, N-terminally processed | RBX1 |
| 21 | DNA-binding protein RFX7 | RFX7 |
| 22 | ATP synthase subunit alpha, mitochondrial | ATP5A1 |
| 23 | Vimentin | VIM |
| 24 | Trafficking protein particle complex subunit 8 | TRAPPC8 |
| 25 | Pyruvate kinase PKM | PKM |
| 26 | GTP-binding nuclear protein Ran | RAN |
| 27 | Prohibitin-2 | PHB2 |
| 28 | Importin subunit alpha-1 | KPNA2 |
| 29 | Synapsin-3 | SYN3 |
| 30 | Peroxisome biogenesis factor 1 | PEX1 |
| 31 | Nibrin | NBN |
| 32 | DnaJ homolog subfamily B member 6; DnaJ homolog subfamily B member 3; DnaJ homolog subfamily B member 8; DnaJ homolog subfamily B member 2 | DNAJB6; DNAJB3; DNAJB8; DNAJB2 |
| 33 | Cystatin-A; Cystatin-A, N-terminally processed | CSTA |
| 34 | T-complex protein 1 subunit alpha | TCP1 |
| 35 | E3 ubiquitin-protein ligase TRIM21 | TRIM21 |
| 36 | Elongation factor 1-gamma | EEF1G |
| 37 | Double-strand break repair protein MRE11A | MRE11A |
| 38 | Heat shock protein 75 kDa, mitochondrial | TRAP1 |
| 39 | Probable C-mannosyltransferase DPY19L1 | DPY19L1 |
| 40 | Biogenesis of lysosome-related organelles complex 1 subunit 2 | BLOC1S2 |
| 41 | Nuclear pore complex protein Nup93 | NUP93 |
| 42 | Leucine-rich repeat neuronal protein 4 | LRRN4 |
| 43 | Very-long-chain enoyl-CoA reductase | TECR |
| 44 | Peroxisomal sarcosine oxidase | PIPOX |
| 45 | Mitochondrial dicarboxylate carrier | SLC25A10 |
| 46 | Wings apart-like protein homolog | WAPAL |
| 47 | Cofilin-1; Destrin; Cofilin-2 | CFL1; DSTN; CFL2 |
| 48 | Tubulin alpha-1B chain; Tubulin alpha-1A chain; Tubulin alpha-1C chain; Tubulin alpha-4A chain; Tubulin alpha-3C/D chain; Tubulin alpha-3E chain | TUBA1B; TUBA1A; TUBA1C; TUBA4A; TUBA3C; TUBA3E |
| 49 | Heat shock 70 kDa protein 1B; Heat shock 70 kDa protein 1A | HSPA1B; HSPA1A |

In another Mass Spectrometry analysis, proteins that interacted with and were preferentially phosphorylated in the U3 or U4 sample were identified (Table 2, below). This Mass Spectrometry analysis only looked at the increase in protein phosphorylation, comparing the U3 and U4 versus wildtype Cas9, and did not take into account absolute amounts of the proteins.

TABLE 2

Proteins preferentially phosphorylated by interaction with U3 or U4

| | Protein name | Gene name | Number of preferentially phosphorylated positions |
|---|---|---|---|
| 1 | Puromycin-sensitive aminopeptidase-like protein | NPEPPSL1 | 1 |
| 2 | Serine/arginine repetitive matrix protein 3 | SRRM3 | 2 |
| 3 | Protein PAT1 homolog 2 | PATL2 | 1 |
| 4 | Centrosomal protein of 290 kDa | CEP290 | 2 |
| 5 | Zinc finger protein 25 | ZNF25 | 2 |
| 6 | ADAMTS-like protein 3 | ADAMTSL3 | 2 |
| 7 | CAP-Gly domain-containing linker protein 4 | CLIP4 | 3 |
| 8 | EH domain-binding protein 1-like protein 1 | EHBP1L1 | 2 |
| 9 | Synaptotagmin-like protein 5 | SYTL5 | 2 |
| 10 | Guanine nucleotide exchange factor DBS | MCF2L | 1 |
| 11 | Nuclear transition protein 2 | TNP2 | 2 |
| 12 | Protein bicaudal D homolog 1 | BICD1 | 3 |
| 13 | Putative helicase Mov10L1 | MOV10L1 | 1 |

Example 2

Improved Targeted Insertion of Polypeptides

To test the efficiency of editing by chimeric Cas9 in human cell lines, a system of YFP or Flag-tagging of a highly expressed cellular gene was used, namely, the proteasome subunit PSMB6 (FIG. 2A). For fusion of YFP to the C-terminus of PSMB6, a donor DNA with 1 kb homology arms was used. For addition of the Flag tag, a 141b ssODN was used, with 58b and 53b homology arms flanking the insertion. The same guide RNA was used in both systems. The U3 construct consistently produced more PSMB6-YFP than the wild-type Cas9, and this was more pronounced when lower amounts of the Cas9-encoding plasmids were used (FIG. 2B). The difference with 100 ng of transfected plasmid was 1.7-fold (U3 compared to wildtype (wt)). Since the PSMB6-YFP was barely detectable with the wt Cas9 when 10 ng of plasmid was used, the difference here could not be quantified, although it is above 2-fold. The ability to achieve success with low amounts of Cas9 is both scientifically and commercially relevant. Using less Cas9 means a lower likelihood of unwanted off-target effects of excess Cas9 expression. In addition, with protocols using electroporation of costly recombinant Cas9 protein, the ability to minimize the amount needed has obvious advantages. A similar two-fold improvement in efficiency was observed with U3 over wt when adding a Flag tag to the PSMB6 C-terminus (FIG. 2D). To determine whether the UL12 fragment would perform better when fused to the C-terminus of Cas9, the U4 construct was made and tested using the PSMB6-YFP system. FACS analysis was performed on the pools of transfected cells, with 100,000 cells analyzed per sample. FACS analysis showed that control (donor plasmid-only) cells had 0.1% YFP-expressing cells, while the wt Cas9 produced 1% YFP-expressing cells, U3 gave 2%, and U4 1.8% (data not shown). Quantification of multiple experiments using this system with both U3 and U4 was provided in FIG. 2C, showing 1.7-2-fold improvement of the chimeric constructs over wt (**$p<10^{-7}$, *$p<0.04$).

To further validate the improved efficiency of the U3 and U4 constructs, editing were compared using other systems in use in the laboratory. The first was insertion of a cassette encoding Clover (GFP) driven by the CMV promoter. This cassette was inserted into exon 2 of the ABL gene, and insertion of this cassette should result in knockout of ABL expression (FIG. 3A). Editing was quantified by measuring GFP expression in the pools of cells by FACS. The cells were passaged five times following the transfection to eliminate cells expressing GFP directly from the donor plasmid. The FACS was performed when the background from the donor-only control was low. The U3 construct gave 3.3-fold more, and the U4 construct 2-fold more GFP-positive cells than the unmodified Cas9 (FIG. 3B).

The present inventors also made a construct that introduces a puromycin resistance gene, followed by T2A peptide, and YFP fused to the N-terminus of p73, with 1 kb homology arms flanking the insertion (FIGS. 4A-C). This cassette was successfully used to create endogenous YFP-p73 clones in 293 (FIGS. 4A-E) and HCT116 cells (data not shown). To compare the efficiency of editing between the wt and U3 Cas9 constructs, the yield of puromycin resistant cells in pools of cells transfected with the Cas9/sgRNA and donor plasmid was quantified by XTT assay following treatment with puromycin (FIG. 4F). The results showed a 1.7-2.2-fold increase in puromycin-resistant cells when using U3/U4 compared to wt Cas9 (FIG. 4F) (p<0.025).

Example 3

Chimeric Cas9

The fusion of the UL12 N-terminal domain to Cas9 improved the CRISPR/Cas9 genome editing that is dependent on homologous recombination. This can be applied for correction of a point mutation using single stranded oligonucleotide donor DNA (ssODN), for insertion of a small tag using a ssODN donor, or for insertion of larger cassettes using plasmid DNA donor templates. The invention is tested in several human cell lines (HEK293, HEK293T, HEK293FT, MCF10A, HeLa, HCT116, U2Os, HFF), mouse ES cells, and BHK cells (hamster), and is tested in mouse embryos. The chimeric Cas9 constructs are encoded by plasmids for expression following transfection, yet they can also be expressed via transduction with viral vectors, or as mRNAs or recombinant proteins for RNA or protein/RNA transfection/electroporation.

Example 4

Delivery of Chimeric Cas9 by mRNA Transfection, Protein Transfection, and Plasmid Transfection Improved HDR/NHEJ Ratio A single copy of a reporter gene was stably transduced into HEK293FT cells. Editing of this gene using Cas9, sgRNA, and ssODN provided reporter output that could be used to distinguish unedited cells from HDR-edited and NHEJ-edited, by using FACS analysis.

A system was used to test delivery of Cas9 constructs encoded by:
(A) in vitro transcribed RNA encoding the Cas9 and sgRNA, with Lipofectamine MessengerMax reagent used for transfection;
(B) purified recombinant Cas9 proteins, with in vitro transcribed sgRNA, with Lipofectamine 2000 used for transfection;
(C) Cas9 and sgRNA encoded by plasmid, jetPEI used for transfection.

All transfections also included the ssODN donor DNA.

As evident in FIGS. 5A-C, all three delivery systems yielded edited cells (HDR and NHEJ outputs), indicating active Cas9. With all three systems, the chimeric Cas9 constructs U3 and U4 had a higher HDR/NHEJ ratio when compared to wt Cas9, indicating that these constructs favor HDR over NHEJ.

Example 5

Editing of an Endogenous Point Mutation in Baby Hamster (BHK) and Human Cells

To test whether the fusion constructs were more efficient at mediating genome editing, the ability to introduce a point mutation which would revert a temperature-sensitive (ts) mutation to the wild type sequence was tested. A temperature sensitive cell line, BHK21 ts13, was used with a well-defined point mutation, G690D, in the $TAF_{II}$-250 (TAF1) gene on the X chromosome, the largest component of the basal transcription complex TFIID (Hayashida et al., 1994). These cells, a mutant isolate of BHK (baby hamster kidney) cells, grow at permissive temperature (32° C.), but die when incubated for several days at the restrictive temperature of 39.5° C. CRISPR editing of this locus (FIG. 6A) using an ssODN as donor DNA, and incubation of the transfected cells at 39.5° C., produced colonies of the edited cells that are no longer temperature-sensitive. Editing efficiency was quantified by counting the surviving cell colonies after staining with crystal violet. The chimeric constructs showed an advantage in editing efficiency over the wt, with 3-4 fold more editing seen with U3 and U4 (FIG. 6B).

The human and hamster TAF1 genes are highly homologous, accordingly, CRISPR editing was carried out in HEK293 cells to make the same mutation that was identified in the BHK21 ts13 (FIGS. 7A-B). In human cells, this is TAF1 G716D in exon 13 of the TAF1 gene on the X chromosome Like the BHK ts13 cells, the HEK293 TAF1ts cells grew at the permissive temperature (which in this case was 37° C.), but did not survive at the restrictive temperature (39.5° C.). Following transfection of the cells with Cas9/sgRNA and ssODN, cells were transferred to 39.5° C., and colonies of surviving cells were stained and quantified. When non-specific sgRNA or ssODN were used, no HEK293 TAF1ts cell growth was observed, suggesting spontaneous reversion is a very rare event if any (FIG. 7C #1-3). Similarly to what was observed with the BHK21 ts13 cells, the U3 and U4 constructs were, on average, 2-fold more efficient in editing of the HEK293 TAF1ts site (FIGS. 7C,D). The larger size of the colonies produced by editing with the U3 and U4 constructs may indicate faster editing, and thus an earlier start in colony formation in these plates. The reversion of the mutation was specific to the CRISPR/Cas9 mediated HDR, and occurred only with expression of the ts-specific sgRNA and the TAF1 ts-correcting template ssODN together (FIG. 7C).

The 1-126 aa domain of UL12 has nuclear localization signal (NLS) activity (Corcoran et al., 2009; Reuven et al., 2004), with a strong consensus NLS at aa 35-39. To test the possibility that the increased efficiency of the chimeric constructs was due to the added UL12 NLS, a fusion of the 1-50 UL12 fragment to the N-terminus of Cas9 ($U_{NLS}$ construct) was prepared. The editing of the ts mutation by the $U_{NLS}$ construct was the same as wt Cas9, indicating that the improved editing seen with U3 and U4 could not be attributable to the added NLS (FIG. 7C-D). The levels of expression of the Cas9 constructs were the same, as shown by immunoblotting of samples of the transfected cells (FIG. 7E). These data suggest that MRN recruitment by the chimeric Cas9 constructs improved HDR-dependent CRISPR editing of a template-directed point mutation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

REFERENCES

Balasubramanian, N., Bai, P., Buchek, G., Korza, G., and Weller, S. K. (2010). Physical interaction between the herpes simplex virus type 1 exonuclease, UL12, and the DNA double-strand break-sensing MRN complex. Journal of virology 84, 12504-12514.

Charpentier, M., Khedher, A. H. Y., Menoret, S., Brion, A., Lamribet, K., Dardillac, E., Boix, C., Perrouault, L., Tesson, L., Geny, S., De Cian, A., Itier, J. M., Anegon, I., Lopez, B., Giovannangeli, C., and Concordet, J. P. (2018). CtIP fusion to Cas9 enhances transgene integration by homology-dependent repair. Nature communications 9, 1133.

Chu, V. T., Weber, T., Wefers, B., Wurst, W., Sander, S., Rajewsky, K., and Kuhn, R. (2015). Increasing the efficiency of homology-directed repair for CRISPR-Cas9-induced precise gene editing in mammalian cells. Nature biotechnology 33, 543-548.

Cong, L., Ran, F. A., Cox, D., Lin, S., Barretto, R., Habib, N., Hsu, P. D., Wu, X., Jiang, W., Marraffini, L. A., and Zhang, F. (2013). Multiplex genome engineering using CRISPR/Cas systems. Science 339, 819-823.

Corcoran, J. A., Saffran, H. A., Duguay, B. A., and Smiley, J. R. (2009). Herpes simplex virus UL12.5 targets mitochondria through a mitochondrial localization sequence proximal to the N terminus. Journal of virology 83, 2601-2610.

Gagnon, J. A., Valen, E., Thyme, S. B., Huang, P., Akhmetova, L., Pauli, A., Montague, T. G., Zimmerman, S., Richter, C. and Schier, A. F. (2014) Efficient mutagenesis by Cas9 protein-mediated oligonucleotide insertion and large-scale assessment of single-guide RNAs. PloS one, 9, e98186.

Gutschner, T., Haemmerle, M., Genovese, G., Draetta, G. F., and Chin, L. (2016). Post-translational Regulation of Cas9 during G1 Enhances Homology-Directed Repair. Cell reports 14, 1555-1566.

Hayashida, T., Sekiguchi, T., Noguchi, E., Sunamoto, H., Ohba, T., and Nishimoto, T. (1994). The CCG1/TAFII250 gene is mutated in thermosensitive G1 mutants of the BHK21 cell line derived from golden hamster. Gene 141, 267-270.

Hemsley, A., Arnheim, N., Toney, M. D., Cortopassi, G. and Galas, D. J. (1989) A simple method for site-directed mutagenesis using the polymerase chain reaction. Nucleic acids research, 17, 6545-6551.

Hobbs, S., Jitrapakdee, S., and Wallace, J. C. (1998). Development of a bicistronic vector driven by the human polypeptide chain elongation factor 1alpha promoter for creation of stable mammalian cell lines that express very high levels of recombinant proteins. Biochemical and biophysical research communications 252, 368-372.

Kremers, G. J., Goedhart, J., van Munster, E. B., and Gadella, T. W., Jr. (2006). Cyan and yellow super fluorescent proteins with improved brightness, protein folding, and FRET Forster radius. Biochemistry 45, 6570-6580.

Levy, D., Adamovich, Y., Reuven, N., and Shaul, Y. (2007). The Yes-associated protein 1 stabilizes p73 by preventing Itch-mediated ubiquitination of p73. Cell death and differentiation 14, 743-751.

Maruyama, T., Dougan, S. K., Truttmann, M. C., Bilate, A. M., Ingram, J. R., and Ploegh, H. L. (2015). Increasing the efficiency of precise genome editing with CRISPR-Cas9 by inhibition of nonhomologous end joining. Nature biotechnology 33, 538-542.

Reuven, N. B., Antoku, S., and Weller, S. K. (2004). The UL12.5 gene product of herpes simplex virus type 1 exhibits nuclease and strand exchange activities but does not localize to the nucleus. Journal of virology 78, 4599-4608.

Schumacher, A. J., Mohni, K. N., Kan, Y., Hendrickson, E. A., Stark, J. M., and Weller, S. K. (2012). The HSV-1 exonuclease, UL12, stimulates recombination by a single strand annealing mechanism. PLoS pathogens 8, e1002862.

Song, J., Yang, D., Xu, J., Zhu, T., Chen, Y. E., and Zhang, J. (2016). RS-1 enhances CRISPR/Cas9- and TALEN-mediated knock-in efficiency. Nature communications 7, 10548.

Syed, A., and Tainer, J. A. (2018). The MRE11-RAD50-NBS1 Complex Conducts the Orchestration of Damage Signaling and Outcomes to Stress in DNA Replication and Repair. Annual review of biochemistry.

Unger, T., Jacobovitch, Y., Dantes, A., Bernheim, R. and Peleg, Y. (2010) Applications of the Restriction Free (RF) cloning procedure for molecular manipulations and protein expression. Journal of structural biology, 172, 34-44

What is claimed is:

1. A recombinant system for improving genome editing via homologous recombination, the system comprising a first nucleic acid sequence encoding a Cas9 nuclease and a second nucleic acid sequence encoding a UL12 polypeptide, wherein said UL12 polypeptide is devoid of enzymatic activity, and wherein said recombinant system encodes for a Cas9-UL12 fusion protein.

2. A proteinaceous system encoded by the system of claim 1.

3. The system of claim 1, wherein said first nucleic acid sequence and said second nucleic acid sequence are translationally fused.

4. The system of claim 1, further comprising a nucleic acid sequence encoding at least one sgRNA.

5. The system of claim 1, wherein said UL12 polypeptide is capable of increasing homology-directed repair (HDR).

6. The system of claim 1, wherein said UL12 polypeptide is capable of recruiting at least one component of the cellular MRN complex (Mre11/Rad50/Nbs1).

7. The system of claim 1, wherein said UL12 polypeptide is a viral peptide derived from HSV-1.

8. The system of claim 1, wherein said UL12 polypeptide comprises amino acids 1-126 of an N-terminal fragment of UL12 as set forth in SEQ ID NO: 6.

9. The system of claim 1, wherein said Cas9-UL12 fusion protein comprises a linker or a spacer.

10. A nucleic acid construct or construct system comprising said first nucleic acid sequence encoding said Cas9 nuclease and said second nucleic acid sequence encoding said UL12 polypeptide according to the system of claim 1.

11. The nucleic acid construct or construct system of claim 10, wherein said nucleic acid sequence(s) is under a transcriptional control of a cis-acting regulatory element.

12. A pharmaceutical composition comprising the system of claim 1, and a pharmaceutically acceptable carrier or diluent.

13. A method of increasing genome editing in a targeted manner in a target cell, the method comprising subjecting the target cell to a genome editing reagent comprising the system of claim 1 thereby increasing the genome editing in the targeted manner in the target cell.

14. The method of claim 13, wherein said genome editing is associated with a modification selected from the group consisting of a deletion, an insertion, a point mutation and a combination thereof.

15. The method of claim 14, wherein when said modification is an insertion or an insertion-deletion, the method further comprises introducing into the target cell donor oligonucleotides.

16. The method of claim 13, wherein said subjecting is effected in vivo.

17. The method of claim 13, wherein said subjecting is effected ex vivo.

18. The method of claim 13, wherein said target cell is a mammalian cell.

19. The method of claim 13, wherein said target cell is associated with a disease or disorder.

20. A method of treating a disease or disorder amenable to treatment by homologous recombination in a subject in need thereof, the method comprising administering to the subject the system of claim 1, thereby treating the disease or disorder.

21. The method of claim 20, wherein said disease or disorder is selected from the group consisting of a cancer, an infection, an inflammation, an autoimmune disease, a genetic disease or disorder, an immune deficiency, and a metabolic disorder.

* * * * *

SEQUENCE LISTING

<160> NUMBER OF SEQ ID NOS: 37

<210> SEQ ID NO 1

```
<211> LENGTH: 4272
<212> TYPE: DNA
<213> ORGANISM: Artificial Sequence
<220> FEATURE:
<223> OTHER INFORMATION: NUCLEIC ACID SEQ OF CAS9

<400> SEQUENCE: 1
atggactata aggaccacga cggagactac aaggatcatg atattgatta caaagacgat      60
gacgataaga tggccccaaa gaagaagcgg aaggtcggta tccacggagt cccagcagcc     120
gacaagaagt acagcatcgg cctggacatc ggcaccaact ctgtgggctg ggccgtgatc     180
accgacgagt acaaggtgcc cagcaagaaa ttcaaggtgc tgggcaacac cgaccggcac     240
agcatcaaga gaacctgat cggagccctg ctgttcgaca cggcgaaac agccgaggcc     300
acccggctga gagaaccgc cagaagaaga taccagac ggaagaaccg gatctgctat     360
ctgcaagaga tcttcagcaa cgagatggcc aaggtggacg acagcttctt ccacagactg     420
gaagagtcct tcctggtgga agaggataag aagcacgagc ggcaccccat cttcggcaac     480
atcgtggaca aggtggccta ccacgagaag taccccacca tctaccacct gagaaagaaa     540
ctggtggaca gcaccgacaa ggccgacctg cggctgatct atctggccct ggcccacatg     600
atcaagttcc ggggccactt cctgatcgag ggcgacctga accccgacaa cagcgacgtg     660
gacaagctgt tcatccagct ggtgcagacc tacaaccagc tgttcgagga aaaccccatc     720
aacgccagcg gcgtggacgc caaggccatc ctgtctgcca gactgagcaa gagcagacgg     780
ctggaaaatc tgatcgccca gctgcccggc gagaagaaga tggcctgtt cggaaacctg     840
attgccctga gctgggcct gacccccaac ttcaagagca cttcgacct ggccgaggat     900
gccaaactgc agctgagcaa ggacacctac gacgacgacc tggacaacct gctggcccag     960
atcggcgacc agtacgccga cctgtttctg gccgccaaga acctgtccga cgccatcctg    1020
ctgagcgaca tcctgagagt gaacaccgag atcaccaagg ccccctgag cgcctctatg    1080
atcaagagat acgacgagca ccaccaggac ctgaccctgc tgaaagctct cgtgcggcag    1140
cagctgcctg agaagtacaa agagatttc ttcgaccaga gcaagaacgg ctacgccggc    1200
tacattgacg gcggagccag ccaggaagag ttctacaagt tcatcaagcc catcctggaa    1260
aagatggacg gcaccgagga actgctcgtg aagctgaaca gagaggacct gctgcggaag    1320
cagcggacct tcgacaacgg cagcatcccc caccagatcc acctgggaga gctgcacgcc    1380
attctgcggc ggcaggaaga tttttaccca ttcctgaagg acaaccggga aaagatcgag    1440
aagatcctga ccttccgcat cccctactac gtgggccctc tggccagggg aaacagcaga    1500
ttcgcctgga tgaccagaaa gagcgaggaa accatcaccc cctggaactt cgaggaagtg    1560
gtggacaagg gcgcttccgc ccagagcttc atcgagcgga tgaccaactt cgataagaac    1620
ctgcccaacg agaaggtgct gcccaagcac agcctgctgt acgagtactt caccgtgtat    1680
aacgagctga ccaaagtgaa atacgtgacc gagggaatga gaaagcccgc cttcctgagc    1740
ggcgagcaga aaaaggccat cgtggacctg ctgttcaaga ccaaccggaa agtgaccgtg    1800
aagcagctga aggagactca cttcaagaaa atcgagtgct cgactccgt ggaaatctcc    1860
ggcgtggaag atcggttcaa cgcctcccctg ggcacatacc acgatctgct gaaaattatc    1920
aaggacaagg acttcctgga caatgaggaa acgaggaca ttctggaaga tatcgtgctg    1980
accctgacac tgtttgagga cagagagatg atcgaggaac ggctgaaaac ctatgcccac    2040
ctgttcgacg acaaagtgat gaagcagctg aagcggcgcg atacaccgg ctggggcagg    2100
ctgagccgga agctgatcaa cggcatccgg gacaagcagt ccggcaagac aatcctggat    2160
```

```
ttcctgaagt ccgacggctt cgccaacaga aacttcatgc agctgatcca cgacgacagc    2220
ctgaccttta agaggacat ccagaaagcc caggtgtccg gccagggcga tagcctgcac     2280
gagcacattg ccaatctggc cggcagcccc gccattaaga agggcatcct gcagacagtg    2340
aaggtggtgg acgagctcgt gaaagtgatg ggccggcaca gcccgagaa catcgtgatc    2400 gaaatggcca gagagaacca gaccacccag aagggacaga gaacagccg cgagagaatg     2460 aagcggatcg aagagggcat caaagagctg gcagccaga tcctgaaaga acaccccgtg    2520
gaaaacaccc agctgcagaa cgagaagctg tacctgtact acctgcagaa tgggcgggat    2580
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca gtacttctt ctacagcaac    3240 atcatgaact tttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480 agaaagaagg actgggaccc taagaagtac ggcggcttcg acagcccac cgtggcctat    3540 tctgtgctgg tggtggccaa agtggaaaag ggcaagtcca gaaactgaa gagtgtgaaa    3600 gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtggaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag    4140
gtgctggacg ccacccctgat ccaccagagc atcaccggcc tgtacgagac acggatcgac    4200
ctgtctcagc tgggaggcga caaaaggccg cgggccacga aaaaggccgg ccaggcaaaa    4260
aagaaaaagc tt                                                        4272
```

<210> SEQ ID NO 2
<211> LENGTH: 1424
<212> TYPE: PRT
<213> ORGANISM: Artificial Sequence
<220> FEATURE:

-continued

<223> OTHER INFORMATION: AMINO ACID SEQUENCE OF CAS9

<400> SEQUENCE: 2

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
        355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400
```

```
Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
        515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
        595                 600                 605

Lys Lys Ile Glu Cys Phe Asp Ser Val Glu Ile Ser Gly Val Glu Asp
    610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
        675                 680                 685

Gln Leu Lys Arg Arg Arg Tyr Thr Gly Trp Gly Arg Leu Ser Arg Lys
    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
        755                 760                 765

Ser Pro Ala Ile Lys Lys Gly Ile Leu Gln Thr Val Lys Val Val Asp
    770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
```

```
                820              825              830
Gln Ile Leu Lys Glu His Pro Val Glu Asn Thr Gln Leu Gln Asn Glu
            835              840              845
Lys Leu Tyr Leu Tyr Tyr Leu Gln Asn Gly Arg Asp Met Tyr Val Asp
        850              855              860
Gln Glu Leu Asp Ile Asn Arg Leu Ser Asp Tyr Asp Val Asp His Ile
865              870              875              880
Val Pro Gln Ser Phe Leu Lys Asp Asp Ser Ile Asp Asn Lys Val Leu
                885              890              895
Thr Arg Ser Asp Lys Asn Arg Gly Lys Ser Asp Asn Val Pro Ser Glu
            900              905              910
Glu Val Val Lys Lys Met Lys Asn Tyr Trp Arg Gln Leu Leu Asn Ala
        915              920              925
Lys Leu Ile Thr Gln Arg Lys Phe Asp Asn Leu Thr Lys Ala Glu Arg
    930              935              940
Gly Gly Leu Ser Glu Leu Asp Lys Ala Gly Phe Ile Lys Arg Gln Leu
945              950              955              960
Val Glu Thr Arg Gln Ile Thr Lys His Val Ala Gln Ile Leu Asp Ser
                965              970              975
Arg Met Asn Thr Lys Tyr Asp Glu Asn Asp Lys Leu Ile Arg Glu Val
            980              985              990
Lys Val Ile Thr Leu Lys Ser Lys Leu Val Ser Asp Phe Arg Lys Asp
        995              1000             1005
Phe Gln Phe Tyr Lys Val Arg Glu Ile Asn Asn Tyr His His Ala
    1010             1015             1020
His Asp Ala Tyr Leu Asn Ala Val Val Gly Thr Ala Leu Ile Lys
    1025             1030             1035
Lys Tyr Pro Lys Leu Glu Ser Glu Phe Val Tyr Gly Asp Tyr Lys
    1040             1045             1050
Val Tyr Asp Val Arg Lys Met Ile Ala Lys Ser Glu Gln Glu Ile
    1055             1060             1065
Gly Lys Ala Thr Ala Lys Tyr Phe Phe Tyr Ser Asn Ile Met Asn
    1070             1075             1080
Phe Phe Lys Thr Glu Ile Thr Leu Ala Asn Gly Glu Ile Arg Lys
    1085             1090             1095
Arg Pro Leu Ile Glu Thr Asn Gly Glu Thr Gly Glu Ile Val Trp
    1100             1105             1110
Asp Lys Gly Arg Asp Phe Ala Thr Val Arg Lys Val Leu Ser Met
    1115             1120             1125
Pro Gln Val Asn Ile Val Lys Lys Thr Glu Val Gln Thr Gly Gly
    1130             1135             1140
Phe Ser Lys Glu Ser Ile Leu Pro Lys Arg Asn Ser Asp Lys Leu
    1145             1150             1155
Ile Ala Arg Lys Lys Asp Trp Asp Pro Lys Lys Tyr Gly Gly Phe
    1160             1165             1170
Asp Ser Pro Thr Val Ala Tyr Ser Val Leu Val Val Ala Lys Val
    1175             1180             1185
Glu Lys Gly Lys Ser Lys Lys Leu Lys Ser Val Lys Glu Leu Leu
    1190             1195             1200
Gly Ile Thr Ile Met Glu Arg Ser Ser Phe Glu Lys Asn Pro Ile
    1205             1210             1215
Asp Phe Leu Glu Ala Lys Gly Tyr Lys Glu Val Lys Lys Asp Leu
    1220             1225             1230
```

```
Ile Ile Lys Leu Pro Lys Tyr Ser Leu Phe Glu Leu Glu Asn Gly
1235                1240                1245

Arg Lys Arg Met Leu Ala Ser Ala Gly Glu Leu Gln Lys Gly Asn
1250                1255                1260

Glu Leu Ala Leu Pro Ser Lys Tyr Val Asn Phe Leu Tyr Leu Ala
1265                1270                1275

Ser His Tyr Glu Lys Leu Lys Gly Ser Pro Glu Asp Asn Glu Gln
1280                1285                1290

Lys Gln Leu Phe Val Glu Gln His Lys His Tyr Leu Asp Glu Ile
1295                1300                1305

Ile Glu Gln Ile Ser Glu Phe Ser Lys Arg Val Ile Leu Ala Asp
1310                1315                1320

Ala Asn Leu Asp Lys Val Leu Ser Ala Tyr Asn Lys His Arg Asp
1325                1330                1335

Lys Pro Ile Arg Glu Gln Ala Glu Asn Ile Ile His Leu Phe Thr
1340                1345                1350

Leu Thr Asn Leu Gly Ala Pro Ala Ala Phe Lys Tyr Phe Asp Thr
1355                1360                1365

Thr Ile Asp Arg Lys Arg Tyr Thr Ser Thr Lys Glu Val Leu Asp
1370                1375                1380

Ala Thr Leu Ile His Gln Ser Ile Thr Gly Leu Tyr Glu Thr Arg
1385                1390                1395

Ile Asp Leu Ser Gln Leu Gly Gly Asp Lys Arg Pro Ala Ala Thr
1400                1405                1410

Lys Lys Ala Gly Gln Ala Lys Lys Lys Lys Leu
1415                1420

<210> SEQ ID NO 3
<211> LENGTH: 1881
<212> TYPE: DNA
<213> ORGANISM: Artificial Sequence
<220> FEATURE:
<223> OTHER INFORMATION: NUCLEIC ACID SEQ OF UL12

<400> SEQUENCE: 3
atggagtcca cgggaggccc agcatgtccg ccgggacgca ccgtgactaa gcgttcctgg      60
gccctggccg aggacacccc tcgtggcccc gacagccccc ccaagcgccc ccgccctaac     120
agtcttccgc taacaaccac cttccgtccc ctgccccccc accccagac gacgtcagct     180 gtggacccga ctcccattc gcccgttaac ccccccacgtg atcagcacgc caccgacacc     240
gcagacgaaa agccccgggc cgcgtcgccg gcactttctg acgcctcagg gcctccgacc     300
ccagacattc cgctatctcc tgggggcacc cacgcccgcg accgacgc cgatcccgac     360 tccccggacc ttgactctat gtggtcggcg tcggtgatcc ccaacgcgct gccctccat     420 atactagccg agacgttcga gcgccacctg cgcgggttgc tgcgcggcgt ccgcgcccct     480
ctggccatcg tcccctctg ggcccgcctg gattatctgt gttccctggc cgtggtcctc     540
gaggaggcgg gtatggtgga ccgcggactc ggccggcacc tatggcgcct gacgcgccgc     600
gggcccccgg ccgccgcgga cgccgtggcg ccccggcccc tcatgggtt ttacgaggcg     660 gccacgcaaa accaggccga ctgccagcta tgggccctgc tccggcgggg cctcacgacc     720
gcatccaccc tccgctgggg cccccagggt ccgtgtttct cgcccagtg gctgaagcac     780 aacgccagcc tgcggccgga tgtacagtct tcggcggtga tgttcgggcg ggtgaacgag     840
ccgacggccc gaagcctgct gtttcgctac tgcgtgggcc gcgcggacga cggcggcgag     900
```

```
gccggcgccg acacgcggcg ctttatcttc cacgaacccg gcgacctcgc cgaagagaac     960
gtgcatacgt gtggggtcct catggacggt cacacgggga tggtcggggc gtccctggat    1020
attctcgtct gtcctcggga cattcacggc tacttggccc cagtccccaa gaccccctg     1080
gccttttacg aggtcaaatg ccgggccaag tacgctttcg accccatgga ccccagcgac    1140
cccacggcct ccgcgtacga ggacttgatg cacaccggt ccccggaggc gttccgggca     1200
tttatccggt cgatcccgaa gcccagcgtg cgatacttcg cgcccgggcg cgtccccggc    1260
ccggaggagg ctctcgtcac gcaagaccag gcctggtcag aggcccacgc tcgggcgaa    1320
aaaaggcggt gctccgccgc ggatcgggcc ttggtggagt taaatagcgg cgttgtctcg    1380
gaggtgcttc tgtttggcgc ccccgacctc ggacgccaca ccatctcccc cgtgtcctgg    1440
agctccgggg atctggtacg ccgcgagccc gtcttcgcga accccgtca cccgaacttt     1500
aagcagatct tggtgcaggg ctacgtgctc gacagccact ccccgactg ccccccccac     1560
ccgcatctgg tgacgtttat cggcaggcac cgcactagcg cggaggaggg cgtaacgttc    1620
cgcctggagg acggcgccgg ggctctcggg ccgcaggac ccagcaaggc gtccattctc     1680
ccgaaccagg ccgttccgat cgccctgatc attaccccg tccgcatcga tccggagatc     1740
tataaggcca tacagcgaag cagccgcctg gcgttcgacg acacgctcgc cgagctatgg    1800
gcctctcgtt ctccgggacc cggccctgct gctgccgaaa caacgtcctc atcaccgacg    1860
acggggaggt cgtctcgctg a                                              1881
```

<210> SEQ ID NO 4
<211> LENGTH: 626
<212> TYPE: PRT
<213> ORGANISM: Artificial Sequence
<220> FEATURE:
<223> OTHER INFORMATION: AMINO ACID SEQ OF UL12

<400> SEQUENCE: 4

```
Met Glu Ser Thr Gly Gly Pro Ala Cys Pro Pro Gly Arg Thr Val Thr
1               5                   10                  15

Lys Arg Ser Trp Ala Leu Ala Glu Asp Thr Pro Arg Gly Pro Asp Ser
            20                  25                  30

Pro Pro Lys Arg Pro Arg Pro Asn Ser Leu Pro Leu Thr Thr Thr Phe
        35                  40                  45

Arg Pro Leu Pro Pro Pro Gln Thr Thr Ser Ala Val Asp Pro Ser
    50                  55                  60

Ser His Ser Pro Val Asn Pro Arg Asp Gln His Ala Thr Asp Thr
65              70                  75                  80

Ala Asp Glu Lys Pro Arg Ala Ala Ser Pro Ala Leu Ser Asp Ala Ser
            85                  90                  95

Gly Pro Pro Thr Pro Asp Ile Pro Leu Ser Pro Gly Gly Thr His Ala
        100                 105                 110

Arg Asp Pro Asp Ala Asp Pro Asp Ser Pro Asp Leu Asp Ser Met Trp
    115                 120                 125

Ser Ala Ser Val Ile Pro Asn Ala Leu Pro Ser His Ile Leu Ala Glu
    130                 135                 140

Thr Phe Glu Arg His Leu Arg Gly Leu Leu Gly Val Arg Ala Pro
145                 150                 155                 160

Leu Ala Ile Gly Pro Leu Trp Ala Arg Leu Asp Tyr Leu Cys Ser Leu
                165                 170                 175

Ala Val Val Leu Glu Glu Ala Gly Met Val Asp Arg Gly Leu Gly Arg
```

-continued

His Leu Trp Arg Leu Thr Arg Arg Gly Pro Pro Ala Ala Ala Asp Ala
                180              185                 190

Val Ala Pro Arg Pro Leu Met Gly Phe Tyr Glu Ala Ala Thr Gln Asn
195                 200                 205

Gln Ala Asp Cys Gln Leu Trp Ala Leu Leu Arg Arg Gly Leu Thr Thr
210                 215                 220

Ala Ser Thr Leu Arg Trp Gly Pro Gln Gly Pro Cys Phe Ser Pro Gln
225             230                  235                 240

Trp Leu Lys His Asn Ala Ser Leu Arg Pro Asp Val Gln Ser Ser Ala
            245                 250                 255

Val Met Phe Gly Arg Val Asn Glu Pro Thr Ala Arg Ser Leu Leu Phe
        260                 265                 270

Arg Tyr Cys Val Gly Arg Ala Asp Asp Gly Gly Glu Ala Gly Ala Asp
    275                 280                 285

Thr Arg Arg Phe Ile Phe His Glu Pro Gly Asp Leu Ala Glu Glu Asn
290                 295                 300

Val His Thr Cys Gly Val Leu Met Asp Gly His Thr Gly Met Val Gly
305                 310                 315                 320

Ala Ser Leu Asp Ile Leu Val Cys Pro Arg Asp Ile His Gly Tyr Leu
            325                 330                 335

Ala Pro Val Pro Lys Thr Pro Leu Ala Phe Tyr Glu Val Lys Cys Arg
        340                 345                 350

Ala Lys Tyr Ala Phe Asp Pro Met Asp Pro Ser Asp Pro Thr Ala Ser
    355                 360                 365

Ala Tyr Glu Asp Leu Met Ala His Arg Ser Pro Glu Ala Phe Arg Ala
370                 375                 380

Phe Ile Arg Ser Ile Pro Lys Pro Ser Val Arg Tyr Phe Ala Pro Gly
385                 390                 395                 400

Arg Val Pro Gly Pro Glu Glu Ala Leu Val Thr Gln Asp Gln Ala Trp
            405                 410                 415

Ser Glu Ala His Ala Ser Gly Glu Lys Arg Arg Cys Ser Ala Ala Asp
        420                 425                 430

Arg Ala Leu Val Glu Leu Asn Ser Gly Val Val Ser Glu Val Leu Leu
    435                 440                 445

Phe Gly Ala Pro Asp Leu Gly Arg His Thr Ile Ser Pro Val Ser Trp
450                 455                 460

Ser Ser Gly Asp Leu Val Arg Arg Glu Pro Val Phe Ala Asn Pro Arg
465                 470                 475                 480

His Pro Asn Phe Lys Gln Ile Leu Val Gln Gly Tyr Val Leu Asp Ser
            485                 490                 495

His Phe Pro Asp Cys Pro Pro His Pro His Leu Val Thr Phe Ile Gly
        500                 505                 510

Arg His Arg Thr Ser Ala Glu Glu Gly Val Thr Phe Arg Leu Glu Asp
    515                 520                 525

Gly Ala Gly Ala Leu Gly Ala Gly Pro Ser Lys Ala Ser Ile Leu
530                 535                 540

Pro Asn Gln Ala Val Pro Ile Ala Leu Ile Ile Thr Pro Val Arg Ile
545                 550                 555                 560

Asp Pro Glu Ile Tyr Lys Ala Ile Gln Arg Ser Ser Arg Leu Ala Phe
            565                 570                 575

Asp Asp Thr Leu Ala Glu Leu Trp Ala Ser Arg Ser Pro Gly Pro Gly
        580                 585                 590
    595                 600                 605

Pro Ala Ala Ala Glu Thr Thr Ser Ser Ser Pro Thr Thr Gly Arg Ser
    610                 615                 620

Ser Arg
625

<210> SEQ ID NO 5
<211> LENGTH: 378
<212> TYPE: DNA
<213> ORGANISM: Artificial Sequence
<220> FEATURE:
<223> OTHER INFORMATION: NUCLEIC ACIDS SEQUENCE OF THE FIRST 126 AA OF
      UL12 -

<400> SEQUENCE: 5
atggagtcca cgggaggccc agcatgtccg ccgggacgca ccgtgactaa gcgttcctgg      60
gccctggccg aggacacccc tcgtggcccc gacagccccc ccaagcgccc ccgccctaac     120
agtcttccgc taacaaccac cttccgtccc ctgcccccc cacccagac gacgtcagct       180 gtggacccga gctcccattc gcccgttaac ccccacgtg atcagcacgc caccgacacc      240
gcagacgaaa agccccgggc cgcgtcgccg gcactttctg acgcctcagg gcctccgacc     300
ccagacattc cgctatctcc tggggggcacc cacgcccgcg accggacgc cgatcccgac    360 tccccggacc ttgactct                                                  378

<210> SEQ ID NO 6
<211> LENGTH: 126
<212> TYPE: PRT
<213> ORGANISM: Artificial Sequence
<220> FEATURE:
<223> OTHER INFORMATION: THE FIRST 126 AA OF UL12 - AMINO ACIDS SEQUENCE

<400> SEQUENCE: 6

Met Glu Ser Thr Gly Gly Pro Ala Cys Pro Pro Gly Arg Thr Val Thr
1               5                   10                  15

Lys Arg Ser Trp Ala Leu Ala Glu Asp Thr Pro Arg Gly Pro Asp Ser
            20                  25                  30

Pro Pro Lys Arg Pro Arg Pro Asn Ser Leu Pro Leu Thr Thr Thr Phe
        35                  40                  45

Arg Pro Leu Pro Pro Pro Gln Thr Thr Ser Ala Val Asp Pro Ser
    50                  55                  60

Ser His Ser Pro Val Asn Pro Pro Arg Asp Gln His Ala Thr Asp Thr
65                  70                  75                  80

Ala Asp Glu Lys Pro Arg Ala Ala Ser Pro Ala Leu Ser Asp Ala Ser
                85                  90                  95

Gly Pro Pro Thr Pro Asp Ile Pro Leu Ser Pro Gly Gly Thr His Ala
            100                 105                 110

Arg Asp Pro Asp Ala Asp Pro Asp Ser Pro Asp Leu Asp Ser
        115                 120                 125

<210> SEQ ID NO 7
<211> LENGTH: 4659
<212> TYPE: DNA
<213> ORGANISM: Artificial Sequence
<220> FEATURE:
<223> OTHER INFORMATION: THE COMPLETE CAS9-UL12 FUSION PROTEIN U3 -
      NUCLEIC ACIDS

<400> SEQUENCE: 7
atggagtcca cgggaggccc agcatgtccg ccgggacgca ccgtgactaa gcgttcctgg      60

```
gccctggccg aggacacccc tcgtggcccc gacagccccc ccaagcgccc ccgccctaac    120
agtcttccgc taacaaccac cttccgtccc ctgccccccc cacccagac gacgtcagct    180
gtggaccga gctcccattc gcccgttaac cccccacgtg atcagcacgc caccgacacc    240
gcagacgaaa agcccggc cgcgtcgccg gcactttctg acgcctcagg gcctccgacc    300
ccagacattc cgctatctcc tgggggcacc cacgcccgcg acccggacgc cgatcccgac    360
tccccggacc ttgactctgg atccgtcatg gactataagg accacgacgg agactacaag    420
gatcatgata ttgattacaa agacgatgac gataagatgg ccccaaagaa gaagcggaag    480
gtcggtatcc acgagtccc agcagccgac aagaagtaca gcatcggcct ggacatcggc    540
accaactctg tgggctgggc cgtgatcacc gacgagtaca aggtgcccag caagaaattc    600
aaggtgctgg gcaacaccga ccggcacagc atcaagaaga acctgatcgg agccctgctg    660
ttcgacagcg gcgaaacagc cgaggccacc cggctgaaga gaaccgccag aagaagatac    720
accagacgga agaaccggat ctgctatctg caagagatct tcagcaacga gatggccaag    780
gtggacgaca gcttcttcca cagactggaa gagtccttcc tggtggaaga ggataagaag    840
cacgagcggc accccatctt cggcaacatc gtggacgagg tggcctacca cgagaagtac    900
cccaccatct accctgag aaagaaactg gtggacagca ccgacaaggc cgacctgcgg    960
ctgatctatc tggccctggc ccacatgatc aagttccggg gccacttcct gatcgagggc   1020
gacctgaacc ccgacaacag cgacgtggac aagctgttca tccagctggt gcagacctac   1080
aaccagctgt tcgaggaaaa ccccatcaac gccagcggcg tggacgccaa ggccatcctg   1140
tctgccagac tgagcaagag cagacggctg gaaaatctga tcgcccagct gcccggcgag   1200
aagaagaatg gcctgttcgg aaacctgatt gccctgagcc tgggcctgac ccccaacttc   1260
aagagcaact tcgacctggc cgaggatgcc aaactgcagc tgagcaagga cacctacgac   1320
gacgacctgg acaacctgct ggcccagatc ggcgaccagt acgccgacct gtttctggcc   1380
gccaagaacc tgtccgacgc catcctgctg agcgacatcc tgagagtgaa caccgagatc   1440
accaaggccc ccctgagcgc ctctatgatc aagagatacg acgagcacca ccaggacctg   1500
accctgctga agctctcgt gcggcagcag ctgcctgaga agtacaaaga gattttcttc   1560
gaccagagca agaacggcta cgccggctac attgacggcg gagccagcca ggaagagttc   1620
tacaagttca tcaagcccat cctggaaaag atggacggca ccgaggaact gctcgtgaag   1680
ctgaacagag aggacctgct gcggaagcag cggaccttcg acaacggcag catccccac    1740
cagatccacc tgggagagct gcacgccatt ctgcggcggc aggaagattt ttacccattc   1800
ctgaaggaca accgggaaaa gatcgagaag atcctgacct tccgcatccc ctactacgtg   1860
ggccctctgg ccaggggaaa cagcagattc gcctggatga ccagaaagag cgaggaaacc   1920
atcaccccct ggaacttcga ggaagtggtg acaagggcg cttccgccca gagcttcatc   1980
gagcggatga ccaacttcga taagaacctg cccaacgaga ggtgctgcc aagcacagc    2040
ctgctgtacg agtacttcac cgtgtataac gagctgacca aagtgaaata cgtgaccgag   2100
ggaatgagaa agcccgcctt cctgagcggc gagcagaaaa aggccatcgt ggacctgctg   2160
ttcaagacca accggaaagt gaccgtgaag cagctgaaag aggactactt caagaaaatc   2220
gagtgcttcg actccgtgga aatctccggc gtggaagatc ggttcaacgc ctccctgggc   2280
acataccacg atctgctgaa aattatcaag gacaaggact cctggacaa tgaggaaaac   2340
gaggacattc tggaagatat cgtgctgacc ctgacactgt tgaggacag agagatgatc   2400
gaggaacggc tgaaaaccta tgcccacctg ttcgacgaca aagtgatgaa gcagctgaag   2460
```

-continued

```
cggcggagat acaccggctg gggcaggctg agccggaagc tgatcaacgg catccgggac    2520
aagcagtccg gcaagacaat cctggatttc ctgaagtccg acggcttcgc aacagaaac    2580 ttcatgcagc tgatccacga cgacagcctg acctttaaag aggacatcca gaaagcccag    2640
gtgtccggcc agggcgatag cctgcacgag cacattgcca atctggccgg cagccccgcc    2700
attaagaagg gcatcctgca gacagtgaag gtggtggacg agctcgtgaa agtgatgggc    2760
cggcacaagc ccgagaacat cgtgatcgaa atggccagag agaaccagac cacccagaag    2820
ggacagaaga acagccgcga gagaatgaag cggatcgaag agggcatcaa agagctgggc    2880
agccagatcc tgaaagaaca ccccgtggaa acacccagc tgcagaacga gaagctgtac    2940
ctgtactacc tgcagaatgg gcgggatatg tacgtggacc aggaactgga catcaaccgg    3000
ctgtccgact acgatgtgga ccatatcgtg cctcagagct ttctgaagga cgactccatc    3060
gacaacaagg tgctgaccag aagcgacaag aaccggggca gagcgacaa cgtgccctcc    3120 gaagaggtcg tgaagaagat gaagaactac tggcggcagc tgctgaacgc caagctgatt    3180
acccagagaa agttcgacaa tctgaccaag gccgagagag cggcctgag cgaactggat    3240 aaggccggct tcatcaagag acagctggtg gaaacccggc agatcacaaa gcacgtggca    3300
cagatcctgg actcccggat gaacactaag tacgacgaga atgacaagct gatccgggaa    3360
gtgaaagtga tcaccctgaa gtccaagctg gtgtccgatt ccggaagga tttccagttt    3420 tacaaagtgc gcgagatcaa caactaccac cacgcccacg acgcctacct gaacgccgtc    3480
gtgggaaccg ccctgatcaa aaagtaccct aagctggaaa gcgagttcgt gtacggcgac    3540
tacaaggtgt acgacgtgcg gaagatgatc gccaagagcg agcaggaaat cggcaaggct    3600
accgccaagt acttcttcta cagcaacatc atgaactttt tcaagaccga gattaccctg    3660
gccaacggcg agatccggaa gcggcctctg atcgagacaa acggcgaaac cggggagatc    3720
gtgtgggata agggccggga ttttgccacc gtgcggaaag tgctgagcat gccccaagtg    3780
aatatcgtga aaagaccga ggtgcagaca ggcggcttca gcaaagagtc tatcctgccc    3840
aagaggaaca gcgataagct gatcgccaga aagaaggact gggaccctaa gaagtacggc    3900
ggcttcgaca gccccaccgt ggcctattct gtgctggtgg tggccaaagt ggaaaagggc    3960
aagtccaaga aactgaagag tgtgaaagag ctgctgggga tcaccatcat ggaaagaagc    4020
agcttcgaga gaatcccat cgactttctg gaagccaagg gctacaaaga agtgaaaaag    4080
gacctgatca tcaagctgcc taagtactcc ctgttcgagc tggaaaacgg ccggaagaga    4140
atgctggcct ctgccggcga actgcagaag ggaaacgaac tggccctgcc ctccaaatat    4200
gtgaacttcc tgtacctggc cagccactat gagaagctga agggctcccc cgaggataat    4260
gagcagaaac agctgtttgt ggaacagcac aagcactacc tggacgagat catcgagcag    4320
atcagcgagt tctccaagag agtgatcctg gccgacgcta tctggacaa agtgctgtcc    4380 gcctacaaca gcaccgggga taagcccatc agagagcagg ccgagaatat catccacctg    4440
tttaccctga ccaatctggg agcccctgcc gccttcaagt actttgacac caccatcgac    4500
cggaagaggt acaccagcac caaagaggtg ctggacgcca ccctgatcca ccagagcatc    4560
accggcctgt acgagacacg gatcgacctg tctcagctgg aggcgacaa aaggccggcg    4620 gccacgaaaa aggccggcca ggcaaaaaag aaaaagctt                          4659
```

<210> SEQ ID NO 8
<211> LENGTH: 1553
<212> TYPE: PRT

<213> ORGANISM: Artificial Sequence
<220> FEATURE:
<223> OTHER INFORMATION: THE COMPLETE CAS9-UL12 FUSION PROTEIN U3 - AMINO ACIDS SEQUENCE

<400> SEQUENCE: 8

```
Met Glu Ser Thr Gly Gly Pro Ala Cys Pro Pro Gly Arg Thr Val Thr
1               5                   10                  15

Lys Arg Ser Trp Ala Leu Ala Glu Asp Thr Pro Arg Gly Pro Asp Ser
            20                  25                  30

Pro Pro Lys Arg Pro Arg Pro Asn Ser Leu Pro Leu Thr Thr Thr Phe
        35                  40                  45

Arg Pro Leu Pro Pro Pro Gln Thr Thr Ser Ala Val Asp Pro Ser
    50                  55                  60

Ser His Ser Pro Val Asn Pro Pro Arg Asp Gln His Ala Thr Asp Thr
65                  70                  75                  80

Ala Asp Glu Lys Pro Arg Ala Ala Ser Pro Ala Leu Ser Asp Ala Ser
                85                  90                  95

Gly Pro Pro Thr Pro Asp Ile Pro Leu Ser Pro Gly Gly Thr His Ala
            100                 105                 110

Arg Asp Pro Asp Ala Asp Pro Asp Ser Pro Asp Leu Asp Ser Gly Ser
        115                 120                 125

Val Met Asp Tyr Lys Asp His Asp Gly Asp Tyr Lys Asp His Asp Ile
130                 135                 140

Asp Tyr Lys Asp Asp Asp Asp Lys Met Ala Pro Lys Lys Lys Arg Lys
145                 150                 155                 160

Val Gly Ile His Gly Val Pro Ala Ala Asp Lys Lys Tyr Ser Ile Gly
                165                 170                 175

Leu Asp Ile Gly Thr Asn Ser Val Gly Trp Ala Val Ile Thr Asp Glu
            180                 185                 190

Tyr Lys Val Pro Ser Lys Lys Phe Lys Val Leu Gly Asn Thr Asp Arg
        195                 200                 205

His Ser Ile Lys Lys Asn Leu Ile Gly Ala Leu Leu Phe Asp Ser Gly
    210                 215                 220

Glu Thr Ala Glu Ala Thr Arg Leu Lys Arg Thr Ala Arg Arg Arg Tyr
225                 230                 235                 240

Thr Arg Arg Lys Asn Arg Ile Cys Tyr Leu Gln Glu Ile Phe Ser Asn
                245                 250                 255

Glu Met Ala Lys Val Asp Asp Ser Phe Phe His Arg Leu Glu Glu Ser
            260                 265                 270

Phe Leu Val Glu Glu Asp Lys Lys His Glu Arg His Pro Ile Phe Gly
        275                 280                 285

Asn Ile Val Asp Glu Val Ala Tyr His Glu Lys Tyr Pro Thr Ile Tyr
    290                 295                 300

His Leu Arg Lys Lys Leu Val Asp Ser Thr Asp Lys Ala Asp Leu Arg
305                 310                 315                 320

Leu Ile Tyr Leu Ala Leu Ala His Met Ile Lys Phe Arg Gly His Phe
                325                 330                 335

Leu Ile Glu Gly Asp Leu Asn Pro Asp Asn Ser Asp Val Asp Lys Leu
            340                 345                 350

Phe Ile Gln Leu Val Gln Thr Tyr Asn Gln Leu Phe Glu Glu Asn Pro
        355                 360                 365

Ile Asn Ala Ser Gly Val Asp Ala Lys Ala Ile Leu Ser Ala Arg Leu
    370                 375                 380
```

-continued

```
Ser Lys Ser Arg Arg Leu Glu Asn Leu Ile Ala Gln Leu Pro Gly Glu
385                 390                 395                 400

Lys Lys Asn Gly Leu Phe Gly Asn Leu Ile Ala Leu Ser Leu Gly Leu
            405                 410                 415

Thr Pro Asn Phe Lys Ser Asn Phe Asp Leu Ala Glu Asp Ala Lys Leu
        420                 425                 430

Gln Leu Ser Lys Asp Thr Tyr Asp Asp Leu Asp Asn Leu Leu Ala
    435                 440                 445

Gln Ile Gly Asp Gln Tyr Ala Asp Leu Phe Leu Ala Ala Lys Asn Leu
450                 455                 460

Ser Asp Ala Ile Leu Leu Ser Asp Ile Leu Arg Val Asn Thr Glu Ile
465                 470                 475                 480

Thr Lys Ala Pro Leu Ser Ala Ser Met Ile Lys Arg Tyr Asp Glu His
            485                 490                 495

His Gln Asp Leu Thr Leu Leu Lys Ala Leu Val Arg Gln Gln Leu Pro
            500                 505                 510

Glu Lys Tyr Lys Glu Ile Phe Phe Asp Gln Ser Lys Asn Gly Tyr Ala
            515                 520                 525

Gly Tyr Ile Asp Gly Gly Ala Ser Gln Glu Glu Phe Tyr Lys Phe Ile
    530                 535                 540

Lys Pro Ile Leu Glu Lys Met Asp Gly Thr Glu Glu Leu Leu Val Lys
545                 550                 555                 560

Leu Asn Arg Glu Asp Leu Leu Arg Lys Gln Arg Thr Phe Asp Asn Gly
                565                 570                 575

Ser Ile Pro His Gln Ile His Leu Gly Glu Leu His Ala Ile Leu Arg
            580                 585                 590

Arg Gln Glu Asp Phe Tyr Pro Phe Leu Lys Asp Asn Arg Glu Lys Ile
            595                 600                 605

Glu Lys Ile Leu Thr Phe Arg Ile Pro Tyr Tyr Val Gly Pro Leu Ala
610                 615                 620

Arg Gly Asn Ser Arg Phe Ala Trp Met Thr Arg Lys Ser Glu Glu Thr
625                 630                 635                 640

Ile Thr Pro Trp Asn Phe Glu Glu Val Val Asp Lys Gly Ala Ser Ala
            645                 650                 655

Gln Ser Phe Ile Glu Arg Met Thr Asn Phe Asp Lys Asn Leu Pro Asn
            660                 665                 670

Glu Lys Val Leu Pro Lys His Ser Leu Leu Tyr Glu Tyr Phe Thr Val
            675                 680                 685

Tyr Asn Glu Leu Thr Lys Val Lys Tyr Val Thr Glu Gly Met Arg Lys
690                 695                 700

Pro Ala Phe Leu Ser Gly Glu Gln Lys Lys Ala Ile Val Asp Leu Leu
705                 710                 715                 720

Phe Lys Thr Asn Arg Lys Val Thr Val Lys Gln Leu Lys Glu Asp Tyr
            725                 730                 735

Phe Lys Lys Ile Glu Cys Phe Asp Ser Val Glu Ile Ser Gly Val Glu
            740                 745                 750

Asp Arg Phe Asn Ala Ser Leu Gly Thr Tyr His Asp Leu Leu Lys Ile
            755                 760                 765

Ile Lys Asp Lys Asp Phe Leu Asp Asn Glu Glu Asn Glu Asp Ile Leu
            770                 775                 780

Glu Asp Ile Val Leu Thr Leu Thr Leu Phe Glu Asp Arg Glu Met Ile
785                 790                 795                 800

Glu Glu Arg Leu Lys Thr Tyr Ala His Leu Phe Asp Asp Lys Val Met
```

-continued

```
                805                 810                 815
Lys Gln Leu Lys Arg Arg Tyr Thr Gly Trp Gly Arg Leu Ser Arg
            820                 825                 830
Lys Leu Ile Asn Gly Ile Arg Asp Lys Gln Ser Gly Lys Thr Ile Leu
            835                 840                 845
Asp Phe Leu Lys Ser Asp Gly Phe Ala Asn Arg Asn Phe Met Gln Leu
        850                 855                 860
Ile His Asp Asp Ser Leu Thr Phe Lys Glu Asp Ile Gln Lys Ala Gln
865                 870                 875                 880
Val Ser Gly Gln Gly Asp Ser Leu His Glu His Ile Ala Asn Leu Ala
                885                 890                 895
Gly Ser Pro Ala Ile Lys Lys Gly Ile Leu Gln Thr Val Lys Val Val
                900                 905                 910
Asp Glu Leu Val Lys Val Met Gly Arg His Lys Pro Glu Asn Ile Val
                915                 920                 925
Ile Glu Met Ala Arg Glu Asn Gln Thr Thr Gln Lys Gly Gln Lys Asn
            930                 935                 940
Ser Arg Glu Arg Met Lys Arg Ile Glu Glu Gly Ile Lys Glu Leu Gly
945                 950                 955                 960
Ser Gln Ile Leu Lys Glu His Pro Val Glu Asn Thr Gln Leu Gln Asn
                965                 970                 975
Glu Lys Leu Tyr Leu Tyr Tyr Leu Gln Asn Gly Arg Asp Met Tyr Val
            980                 985                 990
Asp Gln Glu Leu Asp Ile Asn Arg Leu Ser Asp Tyr Asp Val Asp His
            995                 1000                1005
Ile Val Pro Gln Ser Phe Leu Lys Asp Asp Ser Ile Asp Asn Lys
    1010                1015                1020
Val Leu Thr Arg Ser Asp Lys Asn Arg Gly Lys Ser Asp Asn Val
    1025                1030                1035
Pro Ser Glu Glu Val Val Lys Lys Met Lys Asn Tyr Trp Arg Gln
    1040                1045                1050
Leu Leu Asn Ala Lys Leu Ile Thr Gln Arg Lys Phe Asp Asn Leu
    1055                1060                1065
Thr Lys Ala Glu Arg Gly Gly Leu Ser Glu Leu Asp Lys Ala Gly
    1070                1075                1080
Phe Ile Lys Arg Gln Leu Val Glu Thr Arg Gln Ile Thr Lys His
    1085                1090                1095
Val Ala Gln Ile Leu Asp Ser Arg Met Asn Thr Lys Tyr Asp Glu
    1100                1105                1110
Asn Asp Lys Leu Ile Arg Glu Val Lys Val Ile Thr Leu Lys Ser
    1115                1120                1125
Lys Leu Val Ser Asp Phe Arg Lys Asp Phe Gln Phe Tyr Lys Val
    1130                1135                1140
Arg Glu Ile Asn Asn Tyr His His Ala His Asp Ala Tyr Leu Asn
    1145                1150                1155
Ala Val Val Gly Thr Ala Leu Ile Lys Lys Tyr Pro Lys Leu Glu
    1160                1165                1170
Ser Glu Phe Val Tyr Gly Asp Tyr Lys Val Tyr Asp Val Arg Lys
    1175                1180                1185
Met Ile Ala Lys Ser Glu Gln Glu Ile Gly Lys Ala Thr Ala Lys
    1190                1195                1200
Tyr Phe Phe Tyr Ser Asn Ile Met Asn Phe Phe Lys Thr Glu Ile
    1205                1210                1215
```

```
Thr Leu Ala Asn Gly Glu Ile Arg Lys Arg Pro Leu Ile Glu Thr
    1220             1225                 1230

Asn Gly Glu Thr Gly Glu Ile Val Trp Asp Lys Gly Arg Asp Phe
    1235             1240                 1245

Ala Thr Val Arg Lys Val Leu Ser Met Pro Gln Val Asn Ile Val
    1250             1255                 1260

Lys Lys Thr Glu Val Gln Thr Gly Gly Phe Ser Lys Glu Ser Ile
    1265             1270                 1275

Leu Pro Lys Arg Asn Ser Asp Lys Leu Ile Ala Arg Lys Lys Asp
    1280             1285                 1290

Trp Asp Pro Lys Lys Tyr Gly Gly Phe Asp Ser Pro Thr Val Ala
    1295             1300                 1305

Tyr Ser Val Leu Val Val Ala Lys Val Glu Lys Gly Lys Ser Lys
    1310             1315                 1320

Lys Leu Lys Ser Val Lys Glu Leu Leu Gly Ile Thr Ile Met Glu
    1325             1330                 1335

Arg Ser Ser Phe Glu Lys Asn Pro Ile Asp Phe Leu Glu Ala Lys
    1340             1345                 1350

Gly Tyr Lys Glu Val Lys Lys Asp Leu Ile Ile Lys Leu Pro Lys
    1355             1360                 1365

Tyr Ser Leu Phe Glu Leu Glu Asn Gly Arg Lys Arg Met Leu Ala
    1370             1375                 1380

Ser Ala Gly Glu Leu Gln Lys Gly Asn Glu Leu Ala Leu Pro Ser
    1385             1390                 1395

Lys Tyr Val Asn Phe Leu Tyr Leu Ala Ser His Tyr Glu Lys Leu
    1400             1405                 1410

Lys Gly Ser Pro Glu Asp Asn Glu Gln Lys Gln Leu Phe Val Glu
    1415             1420                 1425

Gln His Lys His Tyr Leu Asp Glu Ile Ile Glu Gln Ile Ser Glu
    1430             1435                 1440

Phe Ser Lys Arg Val Ile Leu Ala Asp Ala Asn Leu Asp Lys Val
    1445             1450                 1455

Leu Ser Ala Tyr Asn Lys His Arg Asp Lys Pro Ile Arg Glu Gln
    1460             1465                 1470

Ala Glu Asn Ile Ile His Leu Phe Thr Leu Thr Asn Leu Gly Ala
    1475             1480                 1485

Pro Ala Ala Phe Lys Tyr Phe Asp Thr Thr Ile Asp Arg Lys Arg
    1490             1495                 1500

Tyr Thr Ser Thr Lys Glu Val Leu Asp Ala Thr Leu Ile His Gln
    1505             1510                 1515

Ser Ile Thr Gly Leu Tyr Glu Thr Arg Ile Asp Leu Ser Gln Leu
    1520             1525                 1530

Gly Gly Asp Lys Arg Pro Ala Ala Thr Lys Lys Ala Gly Gln Ala
    1535             1540                 1545

Lys Lys Lys Lys Leu
    1550

<210> SEQ ID NO 9
<211> LENGTH: 4644
<212> TYPE: DNA
<213> ORGANISM: Artificial Sequence
<220> FEATURE:
<223> OTHER INFORMATION: the complete cas9-ul12 fusion protein u4 -
      nucleic acids sequence
```

<400> SEQUENCE: 9

```
atggactata aggaccacga cggagactac aaggatcatg atattgatta caaagacgat    60
gacgataaga tggccccaaa gaagaagcgg aaggtcggta tccacggagt cccagcagcc   120
gacaagaagt acagcatcgg cctggacatc ggcaccaact ctgtgggctg gccgtgatc    180
accgacgagt acaaggtgcc cagcaagaaa ttcaaggtgc tgggcaacac cgaccggcac   240
agcatcaaga gaaccctgat cggagccctg ctgttcgaca cggcgaaac agccgaggcc    300
acccggctga agagaaccgc cagaagaaga tacaccagac ggaagaaccg gatctgctat   360
ctgcaagaga tcttcagcaa cgagatggcc aaggtggacg acagcttctt ccacagactg   420
gaagagtcct tcctggtgga agaggataag aagcacgagc ggcaccccat cttcggcaac   480
atcgtggacg aggtggccta ccacgagaag taccccacca tctaccacct gagaaagaaa   540
ctggtggaca gcaccgacaa ggccgacctg cggctgatct atctggccct ggcccacatg   600
atcaagttcc ggggccactt cctgatcgag ggcgacctga accccgacaa cagcgacgtg   660
gacaagctgt tcatccagct ggtgcagacc tacaaccagc tgttcgagga aaaccccatc   720
aacgccagcg gcgtggacgc caaggccatc ctgtctgcca gactgagcaa gagcagacgg   780
ctggaaaatc tgatcgccca gctgcccggc gagaagaaga tggcctgtt cggaaacctg    840
attgccctga gcctgggcct gacccccaac ttcaagagca acttcgacct ggccgaggat   900
gccaaactgc agctgagcaa ggacacctac gacgacgacc tggacaacct gctggcccag   960
atcggcgacc agtacgccga cctgtttctg gccgccaaga acctgtccga cgccatcctg  1020
ctgagcgaca tcctgagagt gaacaccgag atcaccaagg ccccctgag cgcctctatg   1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcgcaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat ccctactac gtgggccctc tggccagggg aaacagcaga   1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa acgaggaca ttctggaaga tatcgtgctg   1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
```

```
aaggtggtgg acgagctcgt gaaagtgatg ggccggcaca agcccgagaa catcgtgatc    2400
gaaatggcca gagagaacca gaccacccag aagggacaga agaacagccg cgagagaatg    2460
aagcggatcg aagagggcat caaagagctg ggcagccaga tcctgaaaga cacccccgtg    2520
gaaaacaccc agctgcagaa cgagaagctg tacctgtact acctgcagaa tgggcgggat    2580
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact tttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480 agaaagaagg actgggaccc taagaagtac ggcggcttcg acagccccac cgtggcctat    3540
tctgtgctgg tggtggccaa agtggaaaag gcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctgaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc cccccgaggat aatgagcaga acagctgtt tgtggaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagccct    4080 gccgccttca gtactttga caccaccatc gaccggaaga ggtacaccag caccaaagag    4140
gtgctggacg ccacccctgat ccaccagagc atcaccggcc tgtacgagac acggatcgac    4200
ctgtctcagc tgggaggcga caaaaggccg gcggccacga aaaggccgg ccagcaaaa    4260 aagaaaatgg agtccacggg aggcccagca tgtccgccgg gacgcaccgt gactaagcgt    4320
tcctgggccc tggccgagga caccctcgt ggccccgaca gcccccccaa gcgccccgc    4380 cctaacagtc ttccgctaac aaccaccttc cgtcccctgc ccccccaccc cagacgacg    4440 tcagctgtga cccgagctc ccattcgccc gttaaccccc cacgtgatca gcacgccacc    4500
gacaccgcag acgaaaagcc ccgggccgcg tcgccggcac tttctgacgc ctcagggcct    4560
ccgaccccag acattccgct atctcctggg ggcacccacg cccgcgaccc ggacgccgat    4620
cccgactccc cggaccttga ctct                                          4644
```

<210> SEQ ID NO 10
<211> LENGTH: 1548
<212> TYPE: PRT
<213> ORGANISM: Artificial Sequence
<220> FEATURE:
<223> OTHER INFORMATION: THE COMPLETE CAS9-UL12 FUSION PROTEIN U4 - AMINO ACIDS SEQUENCE

<400> SEQUENCE: 10

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
        50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
        355                 360                 365
```

```
Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
        515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
        595                 600                 605

Lys Lys Ile Glu Cys Phe Asp Ser Val Glu Ile Ser Gly Val Glu Asp
    610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
        675                 680                 685

Gln Leu Lys Arg Arg Arg Tyr Thr Gly Trp Gly Arg Leu Ser Arg Lys
    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
        755                 760                 765

Ser Pro Ala Ile Lys Lys Gly Ile Leu Gln Thr Val Lys Val Val Asp
    770                 775                 780
```

-continued

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
            805                 810                 815

Arg Glu Arg Met Lys Arg Ile Glu Glu Gly Ile Lys Glu Leu Gly Ser
                820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
    850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
            885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
        915                 920                 925

Lys Leu Ile Thr Gln Arg Lys Phe Asp Asn Leu Thr Lys Ala Glu Arg
    930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
        995                 1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu

```
            1190                1195                1200

Gly Ile Thr Ile Met Glu Arg Ser Ser Phe Glu Lys Asn Pro Ile
            1205                1210                1215

Asp Phe Leu Glu Ala Lys Gly Tyr Lys Glu Val Lys Lys Asp Leu
            1220                1225                1230

Ile Ile Lys Leu Pro Lys Tyr Ser Leu Phe Glu Leu Glu Asn Gly
            1235                1240                1245

Arg Lys Arg Met Leu Ala Ser Ala Gly Glu Leu Gln Lys Gly Asn
            1250                1255                1260

Glu Leu Ala Leu Pro Ser Lys Tyr Val Asn Phe Leu Tyr Leu Ala
            1265                1270                1275

Ser His Tyr Glu Lys Leu Lys Gly Ser Pro Glu Asp Asn Glu Gln
            1280                1285                1290

Lys Gln Leu Phe Val Glu Gln His Lys His Tyr Leu Asp Glu Ile
            1295                1300                1305

Ile Glu Gln Ile Ser Glu Phe Ser Lys Arg Val Ile Leu Ala Asp
            1310                1315                1320

Ala Asn Leu Asp Lys Val Leu Ser Ala Tyr Asn Lys His Arg Asp
            1325                1330                1335

Lys Pro Ile Arg Glu Gln Ala Glu Asn Ile Ile His Leu Phe Thr
            1340                1345                1350

Leu Thr Asn Leu Gly Ala Pro Ala Ala Phe Lys Tyr Phe Asp Thr
            1355                1360                1365

Thr Ile Asp Arg Lys Arg Tyr Thr Ser Thr Lys Glu Val Leu Asp
            1370                1375                1380

Ala Thr Leu Ile His Gln Ser Ile Thr Gly Leu Tyr Glu Thr Arg
            1385                1390                1395

Ile Asp Leu Ser Gln Leu Gly Gly Asp Lys Arg Pro Ala Ala Thr
            1400                1405                1410

Lys Lys Ala Gly Gln Ala Lys Lys Lys Met Glu Ser Thr Gly Gly
            1415                1420                1425

Pro Ala Cys Pro Pro Gly Arg Thr Val Thr Lys Arg Ser Trp Ala
            1430                1435                1440

Leu Ala Glu Asp Thr Pro Arg Gly Pro Asp Ser Pro Pro Lys Arg
            1445                1450                1455

Pro Arg Pro Asn Ser Leu Pro Leu Thr Thr Thr Phe Arg Pro Leu
            1460                1465                1470

Pro Pro Pro Pro Gln Thr Thr Ser Ala Val Asp Pro Ser Ser His
            1475                1480                1485

Ser Pro Val Asn Pro Pro Arg Asp Gln His Ala Thr Asp Thr Ala
            1490                1495                1500

Asp Glu Lys Pro Arg Ala Ala Ser Pro Ala Leu Ser Asp Ala Ser
            1505                1510                1515

Gly Pro Pro Thr Pro Asp Ile Pro Leu Ser Pro Gly Gly Thr His
            1520                1525                1530

Ala Arg Asp Pro Asp Ala Asp Pro Asp Ser Pro Asp Leu Asp Ser
            1535                1540                1545

<210> SEQ ID NO 11
<211> LENGTH: 118
<212> TYPE: DNA
<213> ORGANISM: Artificial Sequence
<220> FEATURE:
<223> OTHER INFORMATION: Portion of the PSMB6 locus comprising a flag
      tag nucleic acid sequence
```

<400> SEQUENCE: 11
ccactttacc acccgccaag cttgactaca aagacgatga cgacaagtga atcctgggat          60
tctagtatcg ccgttgccac tttaccaccc gcctgaatcc tgggattcta gtatgcaa           118

<210> SEQ ID NO 12
<211> LENGTH: 60
<212> TYPE: DNA
<213> ORGANISM: Artificial Sequence
<220> FEATURE:
<223> OTHER INFORMATION: T2A peptide and cloning site-nucleic acid
      sequence

<400> SEQUENCE: 12
gagggcagag gaagtctgct aacatgcggt gacgtggagg agaatcccgg ccctgctagc          60

<210> SEQ ID NO 13
<211> LENGTH: 20
<212> TYPE: PRT
<213> ORGANISM: Artificial Sequence
<220> FEATURE:
<223> OTHER INFORMATION: T2A peptide and cloning site- amino acid
      sequence

<400> SEQUENCE: 13

Glu Gly Arg Gly Ser Leu Leu Thr Cys Gly Asp Val Glu Glu Asn Pro
1               5                   10                  15

Gly Pro Ala Ser
            20

<210> SEQ ID NO 14
<211> LENGTH: 23
<212> TYPE: DNA
<213> ORGANISM: Artificial sequence
<220> FEATURE:
<223> OTHER INFORMATION: Portion of ABL locus (Fig 3a)

<400> SEQUENCE: 14
cccttcagcg gccagtagca tct                                                  23

<210> SEQ ID NO 15
<211> LENGTH: 23
<212> TYPE: DNA
<213> ORGANISM: Artificial sequence
<220> FEATURE:
<223> OTHER INFORMATION: Portion of p73 locus (Fig 4b)

<400> SEQUENCE: 15
ccggcgtggg gaagatggcc cag                                                  23

<210> SEQ ID NO 16
<211> LENGTH: 27
<212> TYPE: DNA
<213> ORGANISM: Artificial sequence
<220> FEATURE:
<223> OTHER INFORMATION: TAFII-250 (TAF1) gene in BHK21 ts13 cell line
      (Fig 6a) NA seq

<400> SEQUENCE: 16
ccattaatga tgcaagttga catggca                                              27

<210> SEQ ID NO 17
<211> LENGTH: 9
<212> TYPE: PRT
<213> ORGANISM: Artificial sequence

```
<220> FEATURE:
<223> OTHER INFORMATION: TAFII-250 (TAF1) gene in BHK21 ts13 cell line
      (Fig 6a)  AA seq

<400> SEQUENCE: 17

Pro Leu Met Met Gln Val Asp Met Ala
1               5

<210> SEQ ID NO 18
<211> LENGTH: 23
<212> TYPE: DNA
<213> ORGANISM: Artificial sequence
<220> FEATURE:
<223> OTHER INFORMATION: Guide RNA targeting PSMB6 C-terminus (Figure
      2a)

<400> SEQUENCE: 18
tagaatccca ggattcaggc ggg                                           23

<210> SEQ ID NO 19
<211> LENGTH: 23
<212> TYPE: DNA
<213> ORGANISM: Artificial sequence
<220> FEATURE:
<223> OTHER INFORMATION: Guide RNA targeting ABL (Figure 3a)

<400> SEQUENCE: 19
agatgctact ggccgctgaa ggg                                           23

<210> SEQ ID NO 20
<211> LENGTH: 23
<212> TYPE: DNA
<213> ORGANISM: Artificial sequence
<220> FEATURE:
<223> OTHER INFORMATION: Guide RNA targeting p73 (Figure 4b)

<400> SEQUENCE: 20
ctgggccatc ttccccacgc cgg                                           23

<210> SEQ ID NO 21
<211> LENGTH: 23
<212> TYPE: DNA
<213> ORGANISM: Artificial sequence
<220> FEATURE:
<223> OTHER INFORMATION: Guide RNA targeting the mutant TAFII250 in
      BHK21 ts13 cells

<400> SEQUENCE: 21
attaatgatg caagttgaca tgg                                           23

<210> SEQ ID NO 22
<211> LENGTH: 100
<212> TYPE: DNA
<213> ORGANISM: Artificial sequence
<220> FEATURE:
<223> OTHER INFORMATION: ssODN template for correcting the mutation in
      the BHK21 ts13 cells

<400> SEQUENCE: 22
ttaagcccag actcacccgc ttatagtagt tttttatctt ggttgccatg ccaacttgca   60
tcattaatgg tccattttcc tcactgtatt ctgcaagaat                        100

<210> SEQ ID NO 23
<211> LENGTH: 24
<212> TYPE: DNA
<213> ORGANISM: Artificial sequence
```

```
<220> FEATURE:
<223> OTHER INFORMATION: Guide for targeting human TAF1, amino acid
      716:  TAF1_g1_fw

<400> SEQUENCE: 23
caccggaccc ttaatgatgc aggt                                              24

<210> SEQ ID NO 24
<211> LENGTH: 24
<212> TYPE: DNA
<213> ORGANISM: Artificial sequence
<220> FEATURE:
<223> OTHER INFORMATION: Guide for targeting human TAF1, amino acid
      716:  TAF1_g1_re

<400> SEQUENCE: 24
aaacacctgc atcattaagg gtcc                                              24

<210> SEQ ID NO 25
<211> LENGTH: 25
<212> TYPE: DNA
<213> ORGANISM: Artificial sequence
<220> FEATURE:
<223> OTHER INFORMATION: Guide targeting the mutant human TAF1

<400> SEQUENCE: 25
caccgcttaa tgatgcaggt tgaca                                             25

<210> SEQ ID NO 26
<211> LENGTH: 25
<212> TYPE: DNA
<213> ORGANISM: Artificial sequence
<220> FEATURE:
<223> OTHER INFORMATION: Guide targeting the mutant human TAF1:
      humTAF1_tsmut_g2_re

<400> SEQUENCE: 26
aaactgtcaa cctgcatcat taagc                                             25

<210> SEQ ID NO 27
<211> LENGTH: 25
<212> TYPE: DNA
<213> ORGANISM: Artificial sequence
<220> FEATURE:
<223> OTHER INFORMATION: Control guide non-targeting in human: BFP_g2_fw

<400> SEQUENCE: 27
caccgctgca cgccgtgggt caggg                                             25

<210> SEQ ID NO 28
<211> LENGTH: 25
<212> TYPE: DNA
<213> ORGANISM: Artificial sequence
<220> FEATURE:
<223> OTHER INFORMATION: Control guide non-targeting in human:BFP_g2_re

<400> SEQUENCE: 28
aaacccctga cccacggcgt gcagc                                             25

<210> SEQ ID NO 29
<211> LENGTH: 103
<212> TYPE: DNA
<213> ORGANISM: Artificial sequence
<220> FEATURE:
<223> OTHER INFORMATION: ssODN for creating ts mutation (G716D) in
      human TAF1
```

```
<400> SEQUENCE: 29
tctgagcaga gactcacccg tttataatag ttctttatct tggttgccat gtcaacctgc    60
atcattaagg gtccattttc ctcactatat tctgcaagaa taa                     103

<210> SEQ ID NO 30
<211> LENGTH: 100
<212> TYPE: DNA
<213> ORGANISM: Artificial sequence
<220> FEATURE:
<223> OTHER INFORMATION: ssODN for correcting ts mutation to make wt
      human TAF1:

<400> SEQUENCE: 30
ctgagcagag actcacccgt ttataatagt tctttatctt ggttgccatg ccaacctgca    60
tcattaaggg tccattttcc tcactatatt ctgcaagaat                         100

<210> SEQ ID NO 31
<211> LENGTH: 99
<212> TYPE: DNA
<213> ORGANISM: Artificial sequence
<220> FEATURE:
<223> OTHER INFORMATION: Control ssODN

<400> SEQUENCE: 31
accggcaagc tgcccgtgcc ctggcccacc ctcgtgacca ccctgacata cggcgtgcag    60
tgcttcagcc gctaccccga ccacatgaag cagcacgac                          99

<210> SEQ ID NO 32
<211> LENGTH: 26
<212> TYPE: DNA
<213> ORGANISM: Artificial sequence
<220> FEATURE:
<223> OTHER INFORMATION: Primers flanking the TAF1 guide site, to
      amplify 554 bp fragment:TAF1_hum_gen554_fw:

<400> SEQUENCE: 32
gcagaaccca tacatggata tggagg                                        26

<210> SEQ ID NO 33
<211> LENGTH: 26
<212> TYPE: DNA
<213> ORGANISM: Artificial sequence
<220> FEATURE:
<223> OTHER INFORMATION: Primers flanking the TAF1 guide site, to
      amplify 554 bp fragment:TAF1_hum_gen554_re:

<400> SEQUENCE: 33
tatggtatat gttcacagat taccag                                        26

<210> SEQ ID NO 34
<211> LENGTH: 30
<212> TYPE: DNA
<213> ORGANISM: Artificial sequence
<220> FEATURE:
<223> OTHER INFORMATION: Partial human TAF1 wild type sequence  nucleic
      acid

<400> SEQUENCE: 34
ggacccttaa tgatgcaggt tggcatggca                                    30

<210> SEQ ID NO 35
<211> LENGTH: 30
<212> TYPE: DNA
<213> ORGANISM: Artificial sequence
```

```
<220> FEATURE:
<223> OTHER INFORMATION: Partial human TAF1 mutated sequence  nucleic
      acid

<400> SEQUENCE: 35
ggacccttaa tgatgcaggt tgacatggca                                         30

<210> SEQ ID NO 36
<211> LENGTH: 10
<212> TYPE: PRT
<213> ORGANISM: Artificial sequence
<220> FEATURE:
<223> OTHER INFORMATION: Partial human TAF1 wild type sequence  amino
      acid

<400> SEQUENCE: 36

Gly Pro Leu Met Met Gln Val Gly Met Ala
1               5                   10

<210> SEQ ID NO 37
<211> LENGTH: 10
<212> TYPE: PRT
<213> ORGANISM: Artificial sequence
<220> FEATURE:
<223> OTHER INFORMATION: Partial human TAF1 mutated sequence  amino acid

<400> SEQUENCE: 37

Gly Pro Leu Met Met Gln Val Asp Met Ala
1               5                   10
```